(12) United States Patent
Hartman et al.

(10) Patent No.: US 10,731,139 B2
(45) Date of Patent: *Aug. 4, 2020

(54) VARIANT FORMS OF URATE OXIDASE AND USE THEREOF

(71) Applicant: Horizon Pharma Rheumatology LLC, Lake Forest, IL (US)

(72) Inventors: Jacob Hartman, Holon (IL); Simona Mendelovitz, Ramat Aviv (IL)

(73) Assignee: Horizon Pharma Rheumatology LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/202,743

(22) Filed: Nov. 28, 2018

(65) Prior Publication Data

US 2019/0316097 A1 Oct. 17, 2019

Related U.S. Application Data

(60) Continuation of application No. 15/649,478, filed on Jul. 13, 2017, now Pat. No. 10,160,958, which is a division of application No. 15/490,736, filed on Apr. 18, 2017, now abandoned, which is a continuation of application No. 14/671,246, filed on Mar. 27, 2015, now Pat. No. 9,670,467, which is a continuation of application No. 13/972,167, filed on Aug. 21, 2013, now Pat. No. 9,017,980, which is a continuation of application No. 13/461,170, filed on May 1, 2012, now Pat. No. 8,541,205, which is a division of application No. 11/918,297, filed as application No. PCT/US2006/013660 on Apr. 11, 2006, now Pat. No. 8,188,224.

(60) Provisional application No. 60/670,573, filed on Apr. 11, 2005.

(51) Int. Cl.

| *A61K 38/44* | (2006.01) |
| *A61K 47/60* | (2017.01) |
| *A61K 38/00* | (2006.01) |
| *A61K 9/00* | (2006.01) |
| *C07K 17/08* | (2006.01) |
| *C07K 14/00* | (2006.01) |
| *C12N 9/06* | (2006.01) |

(52) U.S. Cl.
CPC ............ *C12N 9/0048* (2013.01); *A61K 38/44* (2013.01); *A61K 47/60* (2017.08); *C12N 9/0046* (2013.01); *C12Y 107/03003* (2013.01)

(58) Field of Classification Search
CPC ........ A61K 38/44; A61K 47/60; A61K 38/00; A61K 47/48; A61K 9/0019; A61K 9/00; C07K 17/08; C07K 14/00
USPC ......... 435/188.191, 252.33, 320.1; 424/94.3, 424/94.4; 536/23.2
See application file for complete search history.

(56) References Cited

U.S. PATENT DOCUMENTS

| 1,141,973 | A | 6/1915 | Nichols |
| 3,451,996 | A | 6/1969 | Sumyk |
| 3,613,231 | A | 10/1971 | Pugh |
| 3,616,231 | A | 10/1971 | Bergmeyer |
| 3,931,399 | A | 1/1976 | Bohn |
| 4,027,676 | A | 6/1977 | Mattei |
| 4,064,010 | A | 12/1977 | Harris |
| 4,141,973 | A | 2/1979 | Balazs |
| 4,169,764 | A | 10/1979 | Nakanishi |
| 4,179,337 | A | 12/1979 | Davis |
| 4,251,431 | A | 2/1981 | Carswell |
| 4,297,344 | A | 10/1981 | Schwinn |
| 4,301,153 | A | 11/1981 | Rosenberg |
| 4,312,979 | A | 1/1982 | Takemoto |
| 4,315,852 | A | 2/1982 | Leibowitz |
| 4,317,878 | A | 3/1982 | Nakanishi |
| 4,343,735 | A | 8/1982 | Menge |
| 4,343,736 | A | 8/1982 | Uemura |
| 4,376,110 | A | 3/1983 | David |
| 4,421,650 | A | 12/1983 | Nagasawa |
| 4,425,431 | A | 1/1984 | Takemoto |
| 4,445,745 | A | 5/1984 | Cartesse |
| 4,450,103 | A | 5/1984 | Konrad |
| 4,460,575 | A | 7/1984 | D Hinterland |
| 4,460,683 | A | 7/1984 | Gloger |
| 4,485,176 | A | 11/1984 | Bollin, Jr. |
| 4,753,796 | A | 6/1988 | Moreno |
| 4,766,106 | A | 8/1988 | Katre |
| 4,797,474 | A | 1/1989 | Patroni |
| 4,816,567 | A | 3/1989 | Cabilly |
| 4,847,079 | A | 7/1989 | Kwan |
| 4,847,325 | A | 7/1989 | Shadle |
| 4,917,888 | A | 4/1990 | Katre |

(Continued)

FOREIGN PATENT DOCUMENTS

| AU | 5251599 A | 2/2000 |
| BE | 837379 A | 7/1976 |

(Continued)

OTHER PUBLICATIONS

International Application No. PCT/US2017/061126; International Preliminary Report on Patentability, dated May 23, 2019; 7 pages.

(Continued)

*Primary Examiner* — Julie Ha

(74) *Attorney, Agent, or Firm* — Dennis A. Bennett; Chris Marion; Stephanie M. Greer

(57) ABSTRACT

Genetically modified proteins with uricolytic activity are described. Proteins comprising truncated urate oxidases and methods for producing them, including PEGylated proteins comprising truncated urate oxidase are described.

21 Claims, 8 Drawing Sheets

Specification includes a Sequence Listing.

(56) References Cited

U.S. PATENT DOCUMENTS

| | | |
|---|---|---|
| 4,945,086 A | 7/1990 | Benitz |
| 4,946,778 A | 8/1990 | Ladner |
| 4,966,963 A | 10/1990 | Patroni |
| 4,987,076 A | 1/1991 | Takashio |
| 4,992,531 A | 2/1991 | Patroni |
| 5,008,377 A | 4/1991 | Patroni |
| 5,010,183 A | 4/1991 | MacFarlane |
| 5,114,916 A | 5/1992 | Shirahata |
| 5,122,614 A | 6/1992 | Zalipsky |
| 5,225,539 A | 7/1993 | Winter |
| 5,283,317 A | 2/1994 | Saifer |
| 5,286,637 A | 2/1994 | Veronese |
| 5,362,641 A | 11/1994 | Fuks |
| 5,382,518 A | 1/1995 | Caput |
| 5,428,128 A | 6/1995 | Mensi-Fattohi |
| 5,458,135 A | 10/1995 | Patton |
| 5,468,478 A | 11/1995 | Saifer |
| 5,529,915 A | 6/1996 | Phillips |
| 5,541,098 A | 7/1996 | Caput |
| 5,567,422 A | 10/1996 | Greenwald |
| 5,585,089 A | 12/1996 | Queen |
| 5,612,460 A | 3/1997 | Zalipsky |
| 5,624,903 A | 4/1997 | Mueller |
| 5,633,227 A | 5/1997 | Muller |
| 5,637,749 A | 6/1997 | Greenwald |
| 5,643,575 A | 7/1997 | Martinez |
| 5,653,974 A | 8/1997 | Hung |
| 5,711,944 A | 1/1998 | Gilbert |
| 5,762,923 A | 6/1998 | Gross |
| 5,766,897 A | 6/1998 | Braxton |
| 5,811,096 A | 9/1998 | Aleman |
| 5,816,397 A | 10/1998 | Pratt |
| 5,824,784 A | 10/1998 | Kinstler |
| 5,880,255 A | 3/1999 | Delgado |
| 5,919,455 A | 7/1999 | Greenwald |
| 5,929,231 A | 7/1999 | Maelkki |
| 5,932,462 A | 8/1999 | Harris |
| 5,948,668 A | 9/1999 | Hartman |
| 5,955,336 A | 9/1999 | Shigyo |
| 6,006,753 A | 12/1999 | Efendic |
| 6,130,318 A | 10/2000 | Wild |
| 6,201,110 B1 | 3/2001 | Olsen |
| 6,211,341 B1 | 4/2001 | Zeelon |
| 6,245,901 B1 | 6/2001 | Von |
| 6,468,210 B1 | 10/2002 | Iliff |
| 6,475,143 B2 | 11/2002 | Iliff |
| 6,524,241 B2 | 2/2003 | Iliff |
| 6,527,713 B2 | 3/2003 | Iliff |
| 6,569,093 B2 | 5/2003 | Iliff |
| 6,575,235 B2 | 6/2003 | Zupanick |
| 6,576,235 B1 | 6/2003 | Williams |
| 6,608,892 B2 | 8/2003 | Shaffer |
| 6,783,965 B1 | 8/2004 | Sherman |
| 6,913,915 B2 | 7/2005 | Ensor |
| 7,056,713 B1 | 6/2006 | Hershfield |
| 7,723,089 B2 | 5/2010 | Williams |
| 7,811,800 B2 | 10/2010 | Hartman |
| 7,927,589 B2 | 4/2011 | Williams |
| 7,927,852 B2 | 4/2011 | Sherman |
| 7,964,381 B2 | 6/2011 | Hartman |
| 8,034,594 B2 | 10/2011 | Hartman |
| 8,067,553 B2 | 11/2011 | Williams |
| 8,148,123 B2 | 4/2012 | Hartman |
| 8,178,334 B2 | 5/2012 | Hartman |
| 8,188,224 B2 | 5/2012 | Hartman |
| 8,293,228 B2 | 10/2012 | Hartman |
| 8,465,735 B2 | 6/2013 | Hartman |
| 8,541,205 B2 | 9/2013 | Hartman |
| 8,618,267 B2 | 12/2013 | Williams |
| 8,913,915 B2 | 12/2014 | Makino |
| 8,921,064 B2 | 12/2014 | Sherman |
| 9,017,980 B2 | 4/2015 | Hartman |
| 9,377,454 B2 | 6/2016 | Rosario-Jansen |
| 9,534,013 B2 | 1/2017 | Fischer |
| 9,670,467 B2 | 6/2017 | Hartman |
| 9,885,024 B2 | 2/2018 | Williams |
| 9,926,537 B2 | 3/2018 | Hartman |
| 9,926,538 B2 | 3/2018 | Hartman |
| 10,160,958 B2 | 12/2018 | Hartman |
| 2002/0010319 A1 | 1/2002 | Ansaldi |
| 2002/0151703 A1 | 10/2002 | Yokoyama |
| 2003/0082786 A1 | 5/2003 | Ensor |
| 2003/0166249 A1 | 9/2003 | Williams |
| 2005/0014240 A1 | 1/2005 | Sherman |
| 2006/0188971 A1 | 8/2006 | Hershfield |
| 2007/0274977 A1 | 11/2007 | Hartman |
| 2008/0145876 A1 | 6/2008 | Armstrong |
| 2008/0159976 A1 | 7/2008 | Hartman |
| 2009/0023715 A1 | 1/2009 | Brown |
| 2009/0169534 A1 | 7/2009 | Hartman |
| 2009/0209021 A1 | 8/2009 | Hartman |
| 2009/0317889 A1 | 12/2009 | Fischer |
| 2010/0323422 A1 | 12/2010 | Williams |
| 2010/0323423 A1 | 12/2010 | Williams |
| 2011/0104751 A1 | 5/2011 | Hartman |
| 2011/0217755 A1 | 9/2011 | Hartman |
| 2012/0070876 A1 | 3/2012 | Hartman |
| 2012/0149083 A1 | 6/2012 | Williams |
| 2012/0225046 A1 | 9/2012 | Hartman |
| 2012/0301454 A1 | 11/2012 | Rosario-Jansen |
| 2012/0309085 A1 | 12/2012 | Hartman |
| 2013/0084273 A1 | 4/2013 | Hartman |
| 2013/0330803 A1 | 12/2013 | Hartman |
| 2014/0363414 A1 | 12/2014 | Sherman |
| 2015/0197732 A1 | 7/2015 | Hartman |
| 2016/0377604 A1 | 12/2016 | Rosario-Jansen |
| 2017/0166873 A1 | 6/2017 | Fischer |
| 2017/0313993 A1 | 11/2017 | Hartman |
| 2018/0188242 A1 | 7/2018 | Rosario-Jansen |
| 2018/0223263 A1 | 8/2018 | Sherman |
| 2019/0317083 A1 | 10/2019 | Rosario-Jansen |
| 2020/0056160 A1 | 2/2020 | Fischer |

FOREIGN PATENT DOCUMENTS

| | | |
|---|---|---|
| CA | 2193993 A1 | 1/1996 |
| CN | 1322141 A | 11/2001 |
| CN | 1322243 A | 11/2001 |
| CN | 101168052 A | 4/2008 |
| DE | 837379 | 8/1955 |
| DE | 279486 A1 | 6/1990 |
| DE | 279486 C | 6/1990 |
| DE | 279489 A1 | 6/1990 |
| EP | 0028033 A2 | 5/1981 |
| EP | 0034307 A2 | 8/1981 |
| EP | 0043980 A2 | 1/1982 |
| EP | 0055188 A1 | 6/1982 |
| EP | 0204283 A2 | 12/1986 |
| EP | 0226448 A2 | 6/1987 |
| EP | 0279486 A2 | 8/1988 |
| EP | 0321134 A2 | 6/1989 |
| EP | 0408461 | 1/1991 |
| EP | 0727437 A2 | 8/1996 |
| EP | 1100542 A2 | 5/2001 |
| EP | 1100880 | 5/2001 |
| JP | 55135590 A | 10/1980 |
| JP | S57192435 A | 11/1982 |
| JP | S6255079 A | 3/1987 |
| JP | S62223192 A | 10/1987 |
| JP | H01216939 A | 8/1989 |
| JP | H0354581 A | 3/1991 |
| JP | H03148298 A | 6/1991 |
| JP | H06255079 A | 9/1994 |
| JP | H09154581 A | 6/1997 |
| JP | H10500565 A | 1/1998 |
| JP | H10502360 A | 3/1998 |
| JP | 1999075876 | 3/1999 |
| JP | 3148208 B2 | 3/2001 |
| JP | 3148298 B2 | 3/2001 |
| JP | 2002522399 A | 7/2002 |
| JP | 2002524053 A | 8/2002 |
| JP | 2003521937 A | 7/2003 |
| JP | 2005241424 A | 9/2005 |
| JP | 2008505656 A | 2/2008 |

(56) References Cited

FOREIGN PATENT DOCUMENTS

| | | |
|---|---|---|
| JP | 2008535499 A | 9/2008 |
| JP | 2008535500 A | 9/2008 |
| JP | 5599189 A | 11/2009 |
| JP | 2013009960 A | 1/2013 |
| JP | 5599189 | 10/2014 |
| KR | 100333148 B1 | 9/1994 |
| KR | 0159107 B1 | 11/1998 |
| KR | 488848 | 2/2000 |
| KR | 100365606 B1 | 6/2000 |
| KR | 100318706 | 12/2001 |
| KR | 100369838 | 1/2003 |
| KR | 19980069019 | 9/2003 |
| KR | 100488848 B1 | 5/2005 |
| RU | 2001103131 A | 8/1999 |
| WO | 8604145 A1 | 7/1986 |
| WO | 8700056 A1 | 1/1987 |
| WO | 9216221 A1 | 10/1992 |
| WO | 9419007 A1 | 9/1994 |
| WO | 9419470 A1 | 9/1994 |
| WO | 9423735 A1 | 10/1994 |
| WO | 9423740 A1 | 10/1994 |
| WO | 9511987 A1 | 5/1995 |
| WO | 9525785 A1 | 9/1995 |
| WO | 9601274 A1 | 1/1996 |
| WO | 9623064 A1 | 8/1996 |
| WO | 9808873 A1 | 3/1998 |
| WO | 9831383 A1 | 7/1998 |
| WO | 2000007629 A2 | 2/2000 |
| WO | 2000008196 A2 | 2/2000 |
| WO | 0159078 A2 | 8/2001 |
| WO | 03011211 A2 | 2/2003 |
| WO | 03045436 A1 | 6/2003 |
| WO | 2004092393 A1 | 10/2004 |
| WO | 2006110761 A2 | 10/2006 |
| WO | 2006110819 A2 | 10/2006 |
| WO | 2008051178 A2 | 5/2008 |
| WO | 2010151823 A1 | 12/2010 |
| WO | 2018089808 | 5/2018 |

OTHER PUBLICATIONS

"Aggregate", Stedman's Medical Dictionary, 27th Edition, PDR Electronic Library, accessed on Jun. 10, 2009 at http://www.thomsonhe.com/pdrel/librarian/ND.

"Amino Acid Sequence of Amino Truncated Chimeric Pig-Baboon Uricase", Retrieved from EBI Accession No. GSP: AAY69153, XP002404207, May 30, 2000.

"Designing Custom Peptides," from SIGMA Genosys, pp. 1-2. Accessed Dec. 16, 2004.

"Dimer", Stedman's Medical Dictionary, 27th Edition, PDR Electronic Library, accessed Jun. 10, 2009 at http://www.thomsonhe.com/pdrel/librarian/ND.

"How to Control Uric Acid Levels" from http://www.top10homeremedies.com/how-to/control-uric-acid-levels.html, pp. 1-6. Accessed Sep. 22, 2015.

"N- and C-Terminally Truncated Pig-Baboon Chimeric Uricase (PBC-NT-CT)", Retrieved from EBI Accession No. GSP: AAY81255, XP002404208, Jun. 19, 2000.

"Short Protocols in Molecular Biology", John Wiley & Sons, (1997).

A list of GenBank Accession Numbers corresponding to Uricase Family Member Sequences submitted by Applicants to the Examiner in corresponding South Korean Appl. No. 2001-7001569 on Aug. 24, 2004.

Abuchowski, A. et al., "Effect of Covalent Attachment of Polyethylene Glycol on Immunogenicity and Circulating Life of Bovine Liver Catalase," J. Biol. Chem. 252:3582-3586, American Society for Biochemistry and Molecular Biology, United States (1977).

Abuchowski, A. et al., "Reduction of Plasma Urate Levels in the Cockerel with Polyethylene Glycol-Uricase," J. Pharmacol. Exp. Ther. 219:352-354, The American Society for Pharmacology and Experimental Therapeutics, United States (1981).

Al-Shawi et al., "A Novel Immunoradiometric Assay for Human Liver Ferritin", J. Clin. Pathol., 36(4), pp. 440-444, Abstract only, (1983).

Alamillo, J. et al, "Purification and molecular properties of urate oxidase from Chlamydomonas reinhardtii," Biochim. Biophys. Acta 1076 :203-208, Elsevier Science Publishers B.V., Netherlands (1991).

Alvares, K. et al., "Rat urate oxidase produced by recombinant baculovirus expression: formation of peroxisome crystalloid core-like structures", Proc. Natl. Acad. Sci. USA 89:4908-4912, National Academy of Sciences, United States, (1992).

Alvares, K. et al., "The Nucleotide Sequence of a Full Length cDNA Clone Encoding Rat Liver Urate Oxidase," Biochem. Biophys. Res. Commun. 158:991-995, Academic Press, Inc., United States, (1989).

Antonopoulos, C. et al., "The Precipitation of Polyanions by Long-Chain Aliphatic Ammonium Compounds", Blochim. Biophys. Acta 54:213-226, (1961).

Augustsson, J. et al., "Low-Dose Glucocorticoid Therapy Decreases Risk for Treatment-Limiting Infusion Reaction to Infliximab in Patients with Rheumatoid Arthritis", Extended Report, Ann. Rheum. Dis., vol. 66, pp. 1462-1466, (2007).

Baraf H. et al., "Resolution of Tophi With Intravenous Peg-uricase in Refractory Gout", Arthritis & Rheumatism, 2005, Sep. Supplement, vol. 52, No. 9, p. S105.

Baraf H. et al., "Resolution of Tophi With Intravenous Peg-uricase in Treatment-Failure Gout", presented at the EULAR—Annual European Congress of Rheumatology, on Jun. 21-24, 2006 at Amsterdam, Netherlands, Poster 465.

Baraf, H. et al. "Arthritis & Rheumatism", The Official Journal of the American College of Rheumatology Abstract Supplement, vol. 52, No. 9, p. S105 (Abstract 194) previously submitted as Lee et al., (Sep. 2005) as "Arthritis & Rheumatism" in The Official Journal of the American College of Rheumatology Abstract Supplement, vol. 52, No. 9, p. S105.

Baraf, H. et al., "Resolution of Tophi With Intravenous Peg-uricase in Refractory Gout", presented at American College of Rheumatology 2005 Annual Scientific Meeting on Nov. 13-17, 2005 at San Diego, CA, Poster 194.

Becker, M. et al., "Activation of Hydroxylic Polymers—by Reaction with Carbonate or Chloroformate Ester in Presence", English Abstract, Derwent World Patents Index, Accession No. 8448552, (2004).

Becker, M. et al., "Febuxocat Compared with Allopurinol in Patients with Hyperuricemia and Gout", N. Engl. J. Med., 353(23): 2450-2461, (2005).

Becker, M., "Hyperuricemia and Gout", The Metabolic and Molecular Bases of Inherited Disease. Edited by Scriver CR, Beaudet AL, Sly WS, Valle D, 8th edn. New York; McGraw-Hill; 2513-2535, (2001).

Ben-Bassat, A. and Bauer, K., "Amino-Terminal Processing of Proteins," Nature vol. 326, p. 315, (1987).

Ben-Bassat, A. et al., "Processing of the Initiation Methionine from Proteins: Properties of the *Escherichia coli* Methionine Aminopeptidase and its Gene Structure," Journal of Bacteriology, vol. 169, No. 2, p. 751-757, (1987).

Benbacer, L. et al., "Interspecies aminopeptidase-N chimeras reveal species-specific receptor recognition by canine coronavirus, feline infectious peritonitis virus, and transmissible gastroenteritis virus", J Virol., 71(1):734-7, (1997), JPN6014045520.

Berendsen, H., "A Glimpse of the Holy Grail?", Science, 282: 642-643, (1998).

Bird et al., "Single-Chain Antigen-Binding Proteins," Science, vol. 242, p. 423-426, Oct. 21, 1988.

Blumberg, B. and Ogston, A., "Further Evidence on the Protein Complexes of Some Hyauronic Acids", Biochem. J. 68:183-188, (1958).

Bossavy, J. et al., "Comparison of the Antithrombotic Effect of PEG-Hirudin and Heparin in a Human Ex Vivo Model of Arterial Thrombosis," Arterioscler. Thromb. Vasc. Biol. 19 :1348-1353, American Heart Association, United States (May 1999).

(56) References Cited

OTHER PUBLICATIONS

Bradley, C. and Barrick, D., "Limits of Cooperativity in a Structurally Modular Protein: Response of the Notch Ankyrin Domain to Analogous Alanine Substitutions in Each Repeat," J. Mol. Biol., 324: 373-386, (2002).

Braun, A. and Alsenz, J., "Development and Use of Enzyme-Linked Immunosorbent Assays (ELISA) for the Detection of Protein Aggregates in Interferon-Alpha (IFN-.alpha.) Formulations," Pharm. Res. 14:1394-1400, Plenum Publishing Corporation, United States, (1997).

Braun, A. et al., "Protein Aggregates Seem to Play a Key Role Among the Parameters Influencing the Antigenicity of Interferon Alpha(IFN-.alpha.) in Normal and Transgenic Mice," Pharm. Res. 14:1472-1478, Plenum Publishing Corporation, United States (Oct. 1997).

Brenda Enzyme Database: E.C. 1.7.3.3, Urate Oxidase, available via internet www.brenda-enzymes.info, Mar. 27, 2008.

Buch, M. et al., "Shortening Infusion Times for Infliximab Administration", Rheumatology, vol. 45, pp. 485-486, (2006).

Burnham, N., "Polymers for delivering peptides and proteins," Am. J. Hosp. Pharm. 51: 210-218, American Society of Hospital Pharmacists, Inc., United States, (1994).

Caliceti, P. et al., "Biopharmaceutical Properties of Uricase Conjugated to Neutral and Amphiphilic Polymers", Bioconjugate Chem. 10:639-646, American Chemical Society, (1999).

Carter, W., "Interferon: evidence for subunit structure", PNAS. 67(2), pp. 620-628, (1970).

Chen, R. et al., "Properties of Two Urate Oxidases Modified by the Covalent Attachment of Poly(Ethylene Glycol)," Biochim. Biophys. Acta 660 :293-298, Elsevier/North Holland Biomedical Press, Netherlands, (1981).

Chinese Second Office Action for Chinese Appplication No. 01807750.1, dated Mar. 21, 2008, Chinese Patent Office, Beijing, China.

Chua, C. et al., "Use of Polyethylene Glycol-Modified Uricase (PEG-Uricase) to Treat Hyperuricemia in a Patient with Non-Hodgkin Lymphoma," Ann. Intern. Med. 109:114-117, American College of Physicians, United States, (1988).

Clark, R. et al., "Long-acting Growth Hormone Produced by Conjugation with Polyethylene Glycol," J. Biol. Chem., 271(36):21969-21977, (1996).

Coiffier, B. et al., "Efficacy and Safety of Rasburicase (recombinant urate oxidase) for the Prevention and Treatment of Hyperuricemia During Induction Chemotherapy of Aggressive Non-Hodgkin's Lymphoma: Results of the GRAAL1 Study", J. Clin. Oncol., 21(23):4402-4406, (2003).

Cole et al., "The EBV-Hybridoma Technique and its Application to Human Lung Cancer," Monoclonal Antibodies and Cancer Therapy, pp. 77-96, 1985.

Colloc'h, N. et al., "Crystal Structure of the protein drug urate oxidase-inhibitor complex at 2.05 .ANG. resolution," Nature Struct. Biol. 4:947-952, Nature Publishing Group, United Kingdom, (1997).

Conley, T. and Priest, D., "Thermodynamics and Stoicheiometry of the Binding of Substrate Analogues to Uricase," Biochem. J. 187:727-732, The Biochemical Society, United Kingdom, (1980).

Cooper, J., "Resolving LAL Test Interferences", J. Parenter Sci. Technol. 44(1):13-5, (1990).

Cote et al., "Generation of human monoclonal antibodies reactive with cellular antigens," Proc. Natl. Acad.Sci. USA, vol. 80, p. 2026-2030, Apr. 1983.

Crivelli, E. et al., "A Single Step Method for the Solubilization and Refolding of Recombinant Protein from E. coli Inclusion Bodies" Australian Journal of Biotechnology vol. 5, No., 2, 78-80, 86 (1991).

Davis, F. et al., "Enzyme-Polyethylene Glycol Adducts: Modified Enzymes with Unique Properties", in Enzyme Engineering, vol. 4, Braun, G. et al., eds, Plenum Press, New York, pp. 169-173, (1978).

Davis. S. et al., "Hypouricaemic Effect of Polyethyleneglycol Modified Urate Oxidase", Lancet, The Lancet Limited, London, GB, pp. 281-283, XP000577404, (1981).

Delgado, C. et al., "The Uses and Properties of PEG-Linked Proteins," Critical Reviews in Therapeutic Drug Carrier Systems, 9(3,4):249-304, (1992).

Derynck et al., "Expression of human fibroblast interferon gene in Escherichia coli," Nature, vol. 287, p. 193-197, Sep. 18, 1980.

Dialog File 351, Accession No. 11389154, Derwent WPI English language abstract for JP 09154581 (Document AO1), dated 1997.

Dialog file 351, Accession No. 8448552, English language abstract for DD 279486 (Document FP3), (2004).

Donadio et al., "Manifestation de Type Anaphylactique apres Injection Intra-Veineuse D'urate-Oxydase Chez Un Enfant Asthmatique Atteint De Leucemie Aigue," La Nouvelle Presse Medicale 10: 711-712 (1981). (English Translation).

EC Number commentary 1.7.3.3 from the Brenda Enzyme Database at <http://www.brenda-enzymes.info> accessed on Mar. 27, 2008.

Embery, G., "Glycosaminoglycans of Human Dental Pulp", J. Biol. Buccale 4:229-236, (1976).

Emmerson, B., "The Management of Gout", N. Engl. J. Med., 334(7):445-451, (1996).

English Language Translation of Brazilian Examination Report dated Oct. 8, 2012 in Brazilian Application No. PI9917760-9, Rio de Janeiro, Brazil.

EP Supplementary Search Report for Application No. 10792756.8 dated Oct. 10, 2013.

Espacenet database, Unverified English language abstract for JP 03-148298, espacenet.com, European Patent Office (Jun. 2003).

Espacenet database, unverified English language abstract for JP 09-154581, Jun. 17, 1997 (Document FP6).

Espacenet Database, Unverified English language abstract of JP 55-099189 A, espacenet.com, European Patent Office (1980).

European Examination Report for European Application No. 01 923 265.1, dated Dec. 13, 2007, European Patent Office, Munich, DE.

European Search Report with Written Opinion dated Oct. 25, 2010, issued in connection with European Patent Application No. 10007912.8.

Examination Report for Application No. 201002407-3 dated Oct. 22, 2013.

Examination Report for Application No. 2604399 dated Nov. 14, 2013.

Examiner's Answer to Appeal Brief dated Jul. 11, 2006; in related U.S. Appl. No. 09/839,946, Williams et al., filed Apr. 19, 2001.

ExPasy ProtParam Tool. https://web.expasy.org/cgi-bin/protparam/protparam. Retrieved on Dec. 19, 2018. p. 1-2 (Year: 2018).

Extended European Search Report from European Application No. 14192835.8 dated Jun. 5, 2015.

Extended European Search Report from European Application No. 15156612.2 dated Aug. 14, 2015.

Fam, A., "Strategies and Controversies in the Treatment of Gout and Hyperuricaemia," Bailliere's Clinical Rheumatology: International Practice and Research 4:177-192, Elsevier Science Ltd., (1990).

FDA—Drug Safety Brouchure—Published on the web for Krystexxa, ref ID 3116893 at http://www.accessdata.fda.gov/drugsatfda_docs/label/2012/125293s034lbl.pdf; pp. 1-14, (2012).

Flinta, C. et al., "Sequence Determinants of Cytosolic N-Terminal Protein Processing", Eur J Biochem., 154(1):193-6, (1986).

Forrest, A. et al., "A New Approach for Designing Population Sparse Sampling Strategies—Applied to Ciprofloxacin PKS", Abstracts of Papers, 49(2):153, 1991.

Francis, G. et al., "PEGylation of cytokines and other therapeutic proteins and peptides: the importance of biological optimisation of coupling techniques," Int. J. Hematol. 68:1-18, Elsevier Science Ireland Ltd., Ireland (Jul. 1998).

Fridovich, I., "The Competitive Inhibition of Uricase by Oxonate and by Related Derivatives of s-Triazines", The Journal of Biological Chemistry, 240:2491-2494, (1965).

Friedman, T. et al., "The urate oxidase gene of Drosophila pseudoobscura and Drosophila malnogaster: evolutionary changes of sequence and regulation", J Mol. Evol., vol. 34, No. 1, pp. 62-77, (1992). Abstract only.

Fuertges, F. and Abuchowski, A., "The Clinical Efficacy of Poly(Ethylene Glycol)-Modified Proteins," J. Control Release 11:139-148, Elsevier Science, The Netherlands, (1990).

(56) References Cited

OTHER PUBLICATIONS

Fujita, T. et al., "Tissue Distribution of 111 In-Labeled Uricase Conjugated with Charged Dextrans and Polyethylene Glycol," J. Pharmacobio-Dyn. 14:623-629, Pharmaceutical Society of Japan, (1991).
Gaertner, H. and Offord, R., "Site-Specific Attachment of Functionalized Poly(ethylene glycol) to the Amino Terminus of Proteins," Bioconjugate Chem. 7:38-44, American Chemical Society, United States (1996).
Ganson, N. et al., "Antibodies to Polyethylene Glycol (PEG) during Phase I Investigation of PEG-Urate Oxidase (PEG-uricase; Puricase. RTM.) for Refractory Gout", presented at American College of Rheumatology Annual Scientific Meeting on Oct. 16-21, 2004 at San Antonio, TX, Poster 808.
Ganson, N., "Control of Hyperuricemia in Subjects with Refractory Gout, and Induction of Antibody Against Poly(ethylene Glycol)(PEG), in a Phase I Trial of Subcutaneous PEGylated Urate Oxidase", Arthritis Research and Therapy, 8(R12):1-10, (2005).
Garay, R. et al., "Antibodies Against Polyeththelene Glycol in Healthy Subjects and in Patients Treated with PEG-Conjugated Agents", Expert Opinion, vol. 9, No. 11, pp. 1319-1323, (2012).
Giglione, C. et al., "Control of Protein life-span by N-terminal methionine excision", EMBO J. vol. 22 No. 1, pp. 13-23, (2003).
Goeddel et al., "Human leukocyte interferon produced by *E. coli* is biologically active," Nature, vol. 287, p. 411, Oct. 2, 1980.
Goldman, S. et al., "A Randomized Comparison Between Rasburicase and Allopurinol in Children with Lymphoma or Leukemia at High Risk for Tumor Lysis", Blood 2001, 97 (10): 2998-3303.
Greenberg, M. and Herschfield, M., "A Radiochemical-High-Performance Liquid Chromatographic Assay for Urate Oxidase in Human Plasma," Anal. Biochem. 176:290-293, Academic Press, Inc., United States, (1989).
Hamburger, S. et al., "Arthritis Advisory Committee Meeting. Pegloticase (Krystexxa) IV fusion", dated Jun. 16, 2009 pp. 1-155. [retrieved Aug. 4, 2010]. Available on the internet: <URL: http//www.fda.gov/downloads/AdvisoryCommittees/CommitteesMeetingMaterials/DrugsAdvisoryCommittee/UCM167777.pdf>especially pp. 108-115.
Hamburger, S., et al. Transcript of oral presentation entitled: "Pegloticase (Krystexxatm) IV infusion," pp. 28-213 U.S. Food and Drug Administration, Center for Drug Evaluation and Research, Arthritis Advisory Committee meeting, Jun. 16, 2009.
Hande, K. et at., "Severe Allopurinol Toxicity. Description and Guidelines for Prevention in Patients in Renal Insufficiency," Am. J. Med. 76:47-56, Excerpta Medica, United States, (1984).
Harris, J. et al., Effect of Pegylation on Pharmaceuticals, Nat. Rev. Drug Discov. 2003, 2(3):214-221.
Hartmann, G., "Exchange in vitro of subunits between enzymes from different organisms: chimeras of enzymes", Angew Chem Int Ed Engl., 15(4):181-6, (1976), JPN6014045522.
Hascall, V. and Heinegard, D., "Aggregation of Cartilage Proteoglycans", J. Biol. Chem., 249(13):4232-4241, 4242-4249, and 4250-4256, (1973).
Hazen, J., "Adjuvants—Terminology, Classification, and Chemistry", Weed Technology, vol. 14:773-784, (2000).
Hedlund, L. et al., "Magnetic Resonance Microscopy of Toxic Renal Injury by Bromoethylamine in Rats", Fundamental and Applied Toxicology 16:787-797, Academic Press, (1991).
Heftmann, E. et al., "Chromatography: fundamentals and applications of chromatographic and electrophoretic methods. Part A: fundamentals and techniques." (1983) Journal of Chromatography, vol. 22A, pp. A104-A110.
Heinegard, D. et al., "Characterization of Chondroitin Sulfate Isolated from Trypsin-Chymotrypsin Digests of Cartilage Proteoglycans", Arch. Biochem. Biophys. 165:427-441, (1974).
Henney, C. and Ellis, E., "Antibody Production to Aggregated Human gamma.G-Globulin in Acquired Hypogammaglobulinemia," New Engl. J. Med. 278:1144-1146, Massachusetts Medical Society, United States (1968).
Herbst, R. et al., "Folding of firefly (*Photinus pyralis*) luciferase: aggreagation and reactivation of unfolding intermediates," Biochemistry, 37 (18) 6586-97, (1998).
Hershfield, M. et al., "Use of Site-Directed Mutagenesis to Enhance the Epitope-shielding Effect of Covalent Modification of Proteins with Polyethylene Glycol", Proc. Natl. Acad. Sci. USA 88:7185-7189, National Academy of Sciences, United States, (1991).
Hershfield, M., "Biochemistry and Immunology of Poly(ethylene glycol)-Modified Adenosine Deaminase (PEG-ADA)," in: ACS Symposium Series 680. Poly(ethylene glycol). Chemsitry and Biological Applications, Harris, J.M. and Zalipsky, S., eds., American Chemical Society, Washington, DC, pp. 145-154 (first available Apr. 1997).
Hinds, K. et al., "Synthesis and Characterization of poly(ethylene glycol)-insuline conjugates," Bioconjugate Chem. 11:195-201, American Chemical Society, United States (Feb. 2000).
Hirel, P. et al., Extent of N-terminal methionine excision from *Escherichia coli* proteins is governed by the side-chain length of the penultimate amino acid, Proc. Natl. Acad. Sci. U.S.A. 86(21): 8247-8251, (1989).
Hortnagl, H. et al., "Membrane Proteins of Chromaffin Granules, Dopamine-hydroxylase, a Major Constituent", The Biochemical Journal, vol. 129, No. 1, pp. 187-195, (1972).
Huse et al., "Generation of a Large Combinatorial Library of the Immunoglobulin Repertoire in Phage Lambda," Science, vol. 246, p. 1275-1281, Dec. 8, 1989.
Huston et al., "Protein engineering of antibody binding sites: Recovery of specific activity in an anti-digoxin single-chain Fv analogue produced in *Escherichia coli*," Proc. Natl. Acad. Sci. USA, vol. 85, pp. 5879-5883, Aug. 1988.
Inada, Y., et al. "Biomedical and biotechnological applications of PEG- and PM-modified proteins," Trends Biotechnol. 13:86-91, Elsevier Science, Ltd., Netherlands (1995).
Information on EC 1.7.3.3—Urate Oxidase: available via internet at www.brenda-enzymes.org/php/flat.sub.--result.php4?ecno=1.7.3.3 &organisms- ub.--list=&Suchword=, Date Jul. 20, 2009.
International Application No. PCT/US1999/017514; International Search Report, dated Mar. 17, 2000; 7 pages.
International Application No. PCT/US1999/017514International Search Report, dated Mar. 17, 2000.
International Application No. PCT/US1999/017678; International Preliminary Report on Patentability, date of completion Aug. 24, 2000; 5 pages.
International Application No. PCT/US1999/017678; International Search Report, dated Feb. 2, 2000; 4 pages.
International Application No. PCT/US2001/040069; International Preliminary Report on Patentabily, date of completeion May 24, 2002; 2 pages.
International Application No. PCT/US2001/040069; International Search Report, dated Dec. 12, 2001; 4 pages.
International Application No. PCT/US2006/013502; International Preliminary Report on Patentability; date of completion Jul. 16, 2007; 05 pages.
International Application No. PCT/US2006/013502; International Search Report and Written Opinion of the International Searching Authority, dated Dec. 13, 2006; 10 pages.
International Application No. PCT/US2006/013660; International Preliminary Report on Patentability, date of completion Mar. 20, 2012; 5 pages.
International Application No. PCT/US2006/013660; International Search Report and Written Opinion of the International Search Authority, dated Nov. 17, 2006; 11 pages.
International Application No. PCT/US2006/013751; International Preliminary Report on Patentability, date of completion Apr. 11, 2005; 5 pages.
International Application No. PCT/US2006/013751; International Search Report and Written Opinion of the International Searching Authority, dated Sep. 6, 2006.
International Application No. PCT/US2010/040082; International Preliminary Report on Patentability, dated Jan. 4, 2012; 6 pages.
International Application No. PCT/US2010/040082; International Search Authority and Written Opinion of the International Search Authority, dated Aug. 19, 2010; 7 pages.

(56) References Cited

OTHER PUBLICATIONS

International Application No. PCT/US2010/040093; International Search Report and Written Opinion of the International Searching Authority, dated Aug. 19, 2010; 06 pages.
International Application No. PCT/US2017/061126; International Search Report and Written Opinion of the International Search Authority, dated Feb. 20, 2018; 10 pages.
International Preliminary Report on Patentability for PCT/US2010/040082 dated Jan. 4, 2012.
International Search Report for Application No. PCT/US2010/040082 dated Aug. 19, 2010.
Ishino, K. and Kudo, S., "Protein concentration dependence on aggregation behavior and properties of soybean 7S and 11S globulins during alkali-treatment," Agricultural and Biological Chemistry (1980), 44(6), 1259-66.
Ito, M. et al., "Identification of an Amino Acid Residue Involved in the Substrate-binding Site of Rat Liver Uricase by Site-directed Mutagenesis," Biochem. Biophys. Res. Commun. 187:101-107, Academic Press, United States, (1992).
Jaques, L., "The Reaction of Heparin with Proteins and Complex Bases", Biochem. J. 37:189-195, (1943).
Johnson, G. et al., "Reviews of Magnetic Resonance in Medicine", Pergamon, 4:187-219, (1992).
Jones, A., "The Isolation of Bacterial Nucleic Acids using Cetyltrimethylammonium Bromide", Biochim. Biophys. Acta 10:607-612, (1953).
Kabat et al., "Sequences of Proteins of Immunological Interest," US Dept. of Health and Human Services, 1983.
Kahn, K. and Tipton, P., "Kinetic Mechanism and Cofactor Content of Soybean Root Nodule Urate Oxidase," Biochemistry 36:4731-4738, American Chemical Society, United States, (1997).
Kawata, A. et al., "Validation of the Sf-36 and Haq-Di in Patients With Treatment-Failure Gout", Ann Rheum Dis 2007;66(Suppl II):236, Poster 359.
Kelly, S. et al., "Diabetes Insipidus in Uricase-Deficient Mice: A Model for Evaluating Therapy with Poly(Ethylene Glycol)-Modified Unease," J. Am. Soc. Nephrol. 12:1001-1009, Lippincott Williams & Wilkins, United States, (2001).
Kinsella, J.E. et al., "Uricase From Fish Liver: Isolation and Some Properties," Comp. Biochem. Physiol. 82B(4):621-624, American Society of Zoologists, Division of Comparative Physiology, Elsevier, Great Britain (1985).
Kinstler, O. et al., "Characterization and Stability of N-terminally PEGylated rhG-CSF," Pharm. Res. 13:996-1002, Plenum Publishing Corporation, United States (1996).
Kissel P. et al., "Modification of Uricaemia and the Excretion of Uric Acid Nitrogen by an Enzyme of Fungal Origin", Nature 1968, 217: 72-74.
Kito, M. et al., "A Simple and Efficient Method for Preparation of Monomethoxypolyethylene Glycol Activated with p-Nitrophenylchloroformate and its Application to Modification of L-Asparaginase," J. Clin. Biochem. Nutr. 21:101-111, Institute of Applied Biochemistry, Japan (1996).
Kohler et al., "Continuous cultures of fused cells secreting antibody of predefined specificity," Nature, vol. 256, p. 495-497, Aug. 7, 1975.
Kontsek,P. et al., "Forty years of interferon," Acta Virologica 41:349-353, Slovak Academic Press, Slovak Republic, (1997).
Kozbor et al., "The production of monoclonal antibodies from human lymphocytes," Immunology Today, vol. 4, No. 3, p. 72, 1983.
Kozma, E. et al., "An Accumulation of Proteoglycans in Scarred Fascia", Mol. Cell. Biochem. 203:103-12, (2000).
Kral, L. et al, "Cloning a cDNA for *Drosophila melanogaster* urate oxidase," Gene 45:131-137, Elsevier Science Publishers B.V., Netherlands (1986).
Kunitani, M. et al., "Classical light scattering quantitation of protein aggregates: off-line spectroscopy versus HPLC detection," J. Pharm. Biomed. Anal. 16:573-586, Elsevier Science B.V., Netherlands (Dec. 1997).

Kunitani, M. et al., "On-Line Characterization of Polyethylene Glycol-Modified Proteins," Journal of Chromatography 588:125-137, Elsevier Science Ltd. (1991).
Larsen, K. "Purification of Nodule-Specific Uricase from Soybean by Arginine-Sepharose Affinity Chromatography", Prep Biochem. 1990; 20(1):1-9 (Abstract Only).
Laurent, T. et al., "Fractionation of Hyaluronic Acid: The Polydispersity of Hyaluronic Acid from the Bovine Vitreous Body", Biochem. Biophys. Acta 42:476-485, (1960).
Leach, M. et al., "Efficacy of Urate Oxidase (Uricozyme) in Tumor Lysis Induced Urate Nephropathy", Clin Lab Haematol 20:169-172, Blackwell Science Limited (Jun. 1998).
Leaustic M. et al., 1983, Rev. Rhum. Mal. Osteoartic 50:553-554.
Lee, C. et al., "Generation of cDNA Probes Directed by Amino Acid Sequence: Cloning of Urate Oxidase," Science 239:1288-1291, American Association for the Advancement of Science, United States, (1988).
Lee, S., "Studies on Glycosaminoglycans in Tissues", Fukushima J. Med. Sci. 19:33-39, (1973).
Lee, T. et al., "A Novel Secretory Tumor Necrosis Factor-Inducible Protein (TSG-6) is a Member of the Family of Hyaluronate Binding Proteins, Closely Related to the Sdhesion ReceptorCD44", J. Cell Biol., 116(2): 545-557, (1992).
Legoux, R. et al., "Cloning and Expression in *Eschericia coli* of the Gene Encoding Aspergillus flavus Urate Oxidase", J. Biol. Chem. 267:8565-8570, American Society for Biochemistry and Molecular Biology, United States, (1992).
Li-Yu, J. et al., "Mutations at the S1 Sites of methionine Aminopeptidases from *Escherichia coli* and *Homo sapiens* Reveal the residues Critical for Substrate Specificity", J. Biol. Chem. 279(20): 21128-21134, (2004).
Li-Yu, J. et al., "Treatment of Chronic Gout. Can We Determine When Urate Stores Are Depleted Enough to Prevent Attacks of Gout?" J. Rheumatol 2001, 28(3):577-580.
List of Gen Bank Accession Nos. For Uricase Family Member Sequences submitted by Applicants in corresponding South Korean National Phase Application 10-2007-7025066 of International Application PCT/US2006/013751 (2004).
Liu et al., Prednisone in Uric Acid Lowering in Symptomatic Heart Failure Patients With Hyperuricemia (PUSH-PATH) Study. Canadian Journal of Cardiology, Sep. 2013, vol. 29, No. 9, pp. 1048-1054. Especially Abstract.
London, M. et al., "Uricolytic Activity of Purified Uricase in Two Human Beings", Science 1957, 125:937-938.
Macart et al., "An improvement of the Coomassie Blue dye binding method allowing an equal sensitivity to various proteins: application to cerebrospinal fluid," Clinica Chimica Acta, 122 (1982) 93-101, Elsevier Biomedical Press.
Maccari, F. and Volpi, N., "Glycosaminoglycan blotting on nitrocellulose membranes treated with cetylpyridinium chloride after agarose-gel electrophoretic separation", Electrophoresis 23:3270-3277, (2002).
Mahler, H. et al., "Studies of Uricase. 1. Preparation, Purification, and Properties of a Cuproprotein," J. Biol. Chem. 216:625-641, American Society for Biochemistry and Molecular Biology, United States (1955).
Mahmoud, H. et al., "Advances in the Management of Malignancy-Associated Hyperuricaemia", Br. J. Cancer (Supplement 4) 77:18-20, Churchill Livingstone, United Kingdom, (1998).
Malakhova, E. et al., "Kinetic properties of bacterial urate oxidase entrapped in hydrated reversed micelles," (1991), Biologicheskie Membrany 8(5), 453-9 (abstract only).
Matsumura, G. et al., "The Preparation of Hyaluronic Acid from Bovine Synovial Fluid", Biochim. Biophys. Acta 69:574-576, (1963). Microscopy, Duke University Medical Center.
Miura, S. et al., "Urate Oxidase is Imported into Peroxisomes Recognizing the C-terminal SKL Motif of Proteins," Eur. J. Biochem. 223:141-146, Blackwell Science Ltd., United Kingdom, (1994).
Moerschell, R. et al., The Specificities of Yeast Methionine Aminopeptidase and Acetylation of Amino-terminal Methionine in Vivo, J. Biol. Chem. 265: 19638-19643, (1990).

(56) References Cited

OTHER PUBLICATIONS

Monkarsh, S. et al., "Positional isomers of monopegylated interferon alpha-2a: isolation, characterization, and biological activity," Anal. Biochem. 247:434-440, Academic Press, United States, (1997).
Montagnac, R. and Schillinter, F., Letter to Editor, Nephrologie, 11 (4):259, (1990).
Montalbini, P. et al., "Isolation and characterization of uricase from bean leaves and its comparison with uredospore enzymes," Plant Sci. 147:139-147, Elsevier Science Ireland Ltd., Ireland (Sep. 1999).
Montalbini, P. et al., "Uricase from leaves: its purification and characterization from three different higher plants," Planta 202:277-283, Springer-Verlag, Germany (Jul. 1997).
Moolenburgh, J.D. et al, "Rasburicase treatment in severe tophaceous gout: a novel therapeutic option." (2006) Clin. Rheumatol., vol. 25, pp. 749-752.
Moore, W. and Leppert, P., "Role of Aggregated Human Growth Hormone (hGH) in Development of Antibodies to hGH," J. Clin. Endocrinol. Metab. 51:691-697, The Endocrine Society, United States, (1980).
Morrison et al., "Chimeric human antibody molecules: Mouse antigen-binding domains with human constant-region domains," Proc. Natl. Acad. Sci. USA, vol. 81, pp. 6851-6855, Nov. 1984.
Motojima et al., "Cloning and sequence analysis ofcDNA for rat liver uricase," JBC 263(32):16677-81, (1988).
Mourad, G. et al., "Role of Anti-Urate Oxidase Precipitant Antibodies in Urate Oxidase Resistant Hyperuremic", La Presse Medicale, 13 (42):2585, (1984).
Moussy, G. et al., "Inter-species DNA polymerase delta chimeras are functional in *Saccharomyces cerevisiae*", Eur J Biochem., 231(1):45-9, (1995), JPN6014045517.
Nagata et al., "Synthesis in *E. coli* of a polypeptide with human leukocyte interferon activity," Nature, vol. 284, p. 316, Mar. 27, 1980.
Nahm, B.H. and Marzluf, G.A. "Induction and De Novo Synthesis of Uricase, a Nitrogen-Regulated Enzyme in Neurospora crassa," Journal for Bacteriology, 169(5):1943-1948, American Society for Microbiology, United States (1987).
NCBI Entrez Protein (PRF) Database, deposited sequence for rat urate oxidase (NP 446220), Wang, X.D., et al., National Lirary of Medicine, National institutes of Health, Accession No. 20127395, accessed at http://www.ncbi.nlm.nih.gov/protein/20127395, accessed on Dec. 10, 2003.
Neuberger et al., "Recombinant antibodies possessing novel effector functions," Nature, vol. 312, p. 604-608, Dec. 13, 1984.
Ngo, J. et al., "Computational Complexity, Protein Structure Prediction, and the Levinthal Paradox", The Protein Folding Problem and Tertiary Structure Prediction, K. Merc Jr. and S. Le Grand Edition, pp. 491-495, (1994).
Nishida, Y. et al., "Hypouricaemic effect after oral administration in chickens of polyethylene glycol-modified uricase entrapped in liposomes", J. Pharm. Pharmacol. 36:354-355, Pharmaceutical Press, United Kingdom, (1984).
Nishimura, H. et al., "Improved Modification of Yeast Uricase with Polyethylene Glycol: Accompanied with Nonimmunoreactivity Towards Anti-Uricase Serum and High Enzymic Activity", Enzyme 26:49-53, Karger, Switzerland, (1981).
Nishimura, H. et al., "Modification of Yeast Uricase with Polyethylene Glycol: Disappearance of Binding Ability towards Anti-Uricase Serum", Enzyme 24:261-264, Karger, Switzerland, (1979).
Nucci, M. et al., "The Therapeutic Value of Poly(Ethylene Glycol)-Modified Proteins", Adv. Drug Deliv. Rev. 6:133-151, Elsevier Science Publishers, Netherlands, (1991).
Osman, A. et al., "Liver uricase in Camelus dromedarius: purification and properties", Comparative Biochemistry and Physiology. B. Comparative Biochemistry, Pergamon Press, London, GB, (1989), vol. 94B, No. 3, ISSN 0305-0491, pp. 469-474, XP002125210.
Otta, M. and Bertini, F., "Solubilization of Particle-Linked Urate Oxidase by Different Agents", Acta Physiol. Latinoam, 25:451-457, (1975).

Pakula, A.A. and Sauer, R.T., "Genetic Analysis of Protein Stability and Function," Annu. Rev. Genet. 23:289-310, Annual Reviews Inc., United States (1989).
Palleroni, A. et al., "Interferon Immunogenicity: Preclinical Evaluation of Interferon-.alpha.2a," J. Interferon Cyto. Res. 17:S23-S27, Mary Ann Liebert, Inc., United States, (1997).
Patent Abstract of Japan , English language abstract of JP 03-148298, Japanese Patent Office (1980).
Patent Abstract of Japan, English language abstract of JP 55-135590 A, Japanese Patent Office (1980).
Patent Abstract of Japan, English language abstract of JP 57-192435 A, Japanese Patent Office (1982).
Patent Abstract of Japan, English language abstract of JP 62-55079 A (1987).
Patent Abstracts of Japan, (20031205), vol. 2003, No. 12.
Patent Abstracts of Japan, English language abstract of JP 09-154581 (Document FP3), dated 1997.
Patent Abstracts of Japan, Unverified English language abstract for JP 55-099189, published Jul. 28, 1980 (Document FP1).
Patton, J., "Mechanisms of Macromolecule Absorption by the Lungs", Adv. Drug Delivery Rev., 19(1):3-36, (1996).
PCR Technology. Principles and Applications for DNA Amplification, Stockton Press, (1989).
Pearce, R. and Mathieson, J., "Quantitative Isolation of Purified Acidic Glycosaminoglycans from Rat Skin", Can. J. Biochemistry 45:1565-1576, (1967).
Perez-Ruiz, F. et al., "Effect of Urate-Lowering Therapy on the Velocity of Size Reduction of Tophi in Chronic Gout", Arthritis Rheum. 2002, 47(4); 356-360.
Philippovich, Y.B., "The Fundamentals of Biochemistry," AGAR: 29-30, Moscow, Russia (1999) (with unverified, Partial English language translation).
Pitts, O., et al., "Uricase: Subunit Composition and Resistance to Denaturants," Biochem. 13:888-892, American Chemical Society, United States (1974).
Porstmann, B. et al., "Comparison of Chromogens for the Determination of Horseradish Peroxidase as a Marker in Enzyme Immunoassay," J. Clin. Chem. Clin. Biochem. 19:435-439, Walter de Gruyter & Co., Germany, (1981).
Potaux, L. et al., "Uricolytic Therapy Value of Urate Oxidase in the Treatment of Hyperuricemia", Nouv. Presse Med., 1975, 4:1109-1112.
Prevent—definition by Merriam-Webster online dictionary; at the web http://www.merriam-webster.com/dictionary/prevent—pp. 1-3, accessed on Jun. 27, 2013.
Pui, C. et al., "Urate oxidase in prevention and treatment of hyperuricemia associated with lymphoid malignancies," Leukemia 11:1813-1816, Stockon Press, United States, (1997).
R&D Focus Drug News (DataStar File IPNR/IPNA), Accession No. 1998:2984 DRUGNL, "PEG-uricase BioTechnology General, Duke University, Mountain View licensing agreement," (Aug. 24, 1998).
Reinders, Practice research in the field of gout: clinical pharmacology of antihyperuricemic drugs, University of Groningen, Doctoral Thesis, Nov. 28, 2008, pp. 1-152. p. 18, Table 2; p. 131, para 2.
Remington's Pharmaceutical Sciences, Mack Publishing Co., (1990).
Richette, P. et al., "Successful Treatment with Rasburicase of a Tophaceous Gout in a Patient Allergic to Allopurinol", Nature Clinical Practice Rheumatology, 2(6):338-342, (2006).
Rinella, J. et al., "Elutability of Proteins from Aluminum-Containing Vaccine Adjuvants by Treatment with Surfactants", J. Colloid Interface Sci. 1998;197:48-56. (1998).
Rosenberg, A., "Effects of Protein Aggregates: An Immunologic Perspective," The AAPS Journal 8:E501-E507, American Association of Pharmaceutical Scientists, United States (Aug. 2006).
Rozenberg, S. et al., "Urate-Oxidase for the Treatment of Tophaceous Gout in Heart Transplant Recipients", Rev Rhum, vol. 62 (5), Eng. Ed. pp. 392-394, (1995).
Rudinger, J., "Characteristics of the amino acids as components of a peptide hormone sequence," Peptide Hormones, JA Parsons Edition, University Park Press, Jun. 1976, pp. 1-7.

(56) References Cited

OTHER PUBLICATIONS

Saifer, M. et al., "Improved Conjugation of Cytokines Using High Molecular Weight Poly(ethylene glycol): PEG-GM-CSF as a Prototype," Polymer. Prepr. 38:575-577, American Chemical Society, United States, (1997).

Saifer, M. et al., "Plasma clearance and immunologic properties of long-acting superoxide dismutase prepared using 35,000 to 120,000 dalton poly-ethylene glycol," Adv Exp Med Biol (1994) 366: 377-387.

Saito, S., "Coagulation and Peptization of Polyelectrolyte Solution by Detergent Ions. I", Kolloid-Zeitschrift 143(2):66-73, (1955).

Sakane, T. and Pardridge, W., "Carboxyl-directed Pegylation of Brain-derived Neurotrophic Factor Markedly Reduces Systemic Clearance with Minimal Loss of Biologic Activity", Pharm. Res. 14:1085-1091, Plenum Publishing Corporation, United States, (1997).

Sambrook, J. et al., "Molecular Cloning. A Laboratory Manual", Cold Spring Harbor Laboratory Press, (1989).

Sartore, L. et al., "Enzyme Modification by mPEG with an Amino Acid or Peptide as Spacer Arms", Applied Biochemistry and Biotechnology 27: 55-63, (1991).

Savoca, K. et al., "Induction of Tolerance in Mice by Uricase and Monomethoxypolyethylene Glycol-Modified Uricase," Int. Archs. Allergy Appl. Immun. 75:58-67, Karger, (1984).

Scandella et al., "A Membrane-Bound Phospholipase Al Purified from *Escherichia colt*," Biochemistry, vol. 10, No. 24, p. 4447, 1971.

Schiavon, O. et al., "Therapeutic proteins: a comparison of chemical and biological properties of uricase conjugated to linear or branched poly(ethylene glycol) and poly(N-acryloylmorpholine)", Il Farmaco, 55(4):264-9, (2000).

Schinzel, R. et al., "The phosphate recognition site of *Escherichia coli* maltodextrin phosphorylase," FEBS, Jul. 1991, 286(1, 2): 125-128.

Schumacher, H. et al., "Outcome Evaluations in Gout", J Rheumatol., 34(6):1381-5, (2007), XP008158539.

Schumacher, R. et al., "Effects of Febuxostat Versus Allopurinol and Placebo in Reducing Serum Urate in Subjects with Hyperuricemia and Gout: A 28-Week, Phase III, Randomized, Double-Blind, Parallel-Group Trial", Arthritis & Rheumatism (Arthritis Care & Research), vol. 59, No. 11, pp. 1540-1548, (2008).

Scott, J., "Aliphatic Ammonium Salts in the Assay of Acidic Polysaccharides from Tissues", Methods Biochem. Anal. 8:145-197, (1960).

Scott, J., "The Precipitation of Polyanions by Long-Chain Aliphatic Ammonium Salts", Biochem. J. 81:418-424, (1961).

Scott, J., "The Reaction of Long-Chain Quarternary Ammonium Salts with Acidic Polysaccharides", Chem. and Ind., 168-169, (1955).

Scott, J., "The solubility of cetylpyridinium complexes of biological polyanions in solution of salts", Biochim, Biophys. Ada 18:428-429, (1955).

Search Report for Application No. 201102592-1, dated Jul. 6, 2012.

Seng Yue, C. et al., Population Pharmacokinetic and Pharmacodynamic Analysis of PEG-uricase in Subjects With Hyperuricemia and Refractory Gout, presented at the American College of Clinical Pharmacy 2006 Annual Meeting on Oct. 26-29, 2006 at St. Louis, Missouri, Poster.

Serafini-Fracassini, A. et al., "The Protein-Polysaccharide Complex of Bovine Nasal Cartilage", Biochem. J. 105:569-575, (1967).

Sharma, B., "Immunogenicity of therapeutic proteins. Part 3: Impact of manufacturing changes," Biotech. Adv. 25:325-331, Elsevier Inc., Netherlands (Jan. 2007).

Shearwater Polymers Inc., "Functionalized Biocompatible Polymers for Research and Pharmaceuticals," in Shearwater Polymers, Inc., Catalog, pp. 27, 47, and 48, (1997).

Sherman, F. et al., "Methionine or not methionine at the beginning of a protein", Bio Essays, vol. 3, Issue 1, pp. 27-31, (1985).

Sherman, M. et al., "Conjugation of High-Molecular Weight Poly(ethylene glycol) to Cytokines: Granulocyte-Macrophage Colony-Stimulating Factors as Model Substrates", ACS Symposium Series 680. Poly(ethylene glycol). Chemistry and Biological Applications, Harris, J.M. and Zalipsky, S., eds., American Chemical Society, Washington, DC, pp. 155-169, (1997).

Sherman, M. et al., "PEG-Uricase in the Management of Treatment-Resistant Gout and Hyperuricemia", Advanced Drug Delivery Reviews, 60(1):59-68, (2008).

Shoji, A. et al., A Retrospective Study of the Relationship Between Serum Urate Level and Recurrent Attacks of Gouty Arthritis: Evidence for Reduction of Recurrent Gouty Arthritis With Antihyperuricemic Therapy, Arthritis Rheum., 51(3):321-325, (2007).

Sigma Catalog, p. 1008, Product Nos. U 3250, 292-8, U3500, U 9375 or U 3377, (1993).

Singapore Search Report for Application No. 201109356-4, dated Feb. 15, 2013.

Smith, T. et al., "Human Lung Tryptase", J. Biol. Chem., 259(17):11046-11051, (1984).

Somack, R. et al., "Preparation of Long-Acting Superoxide Dismutase Using High Molecular Weight Polyethylene Glycol (41,000-72,000 Daltons)", Free Rad. Res. Comms. 12-13:553-562, Harwood Academic Publishers GmBH, Germany, (1991).

Streuli et al., "Target cell specificity of two species of human interferon-a produced in *Escherichia coli* and of hybrid molecules derived from them," Proc. Natl. Acad. Sci. USA, vol. 85, pp. 5879-5883, Aug. 1988.

Sundy, J. and Hershfield, M., "Uricase and Other Novel Agents for the Management of Patients With Treatment-Failure Gout", Curr Rheumatol Rep. Jun. 2007; 9(3):258-64.

Sundy, J. et al., "Efficacy and Tolerability of Pegloticase for the Treatment of Chronic Gout in Patients Refractory to Conventional Treatment: Two Randomized Controlled Trials", American Medical Association, 306(7):711-20, (2011).

Sundy, J. et al., "A Phase 1 Study of Pegylated-Uricase (Puricase) in Subjects with Gout", Arthritis Rheum. 2004 vol. 50, supplement 9, S337-338.

Sundy, J. et al., "A Phase 2 Study of Multiple Doses of Intravenous Polyethylene Glycol (PEG)-uricase in Patients with Hyperuricemia and Refractory Gout", presented at American College of Rheumatology 2005 Annual Scientific Meeting on Nov. 12-17, 2005 at San Diego, CA, #1836.

Sundy, J. et al., "A Phase 2 Study of Multiple Doses of Intravenous Polyethylene Glycol (PEG)-uricase in Patients with Hyperuricemia and Refractory Gout", presented at the EULAR—Annual European Congress of Rheumatology, on Jun. 21-24, 2006 at Amsterdam, Netherlands, Poster 516.

Sundy, J. et al., "A Phase I Study of Pegylated-Uricase (Puricase. RTM.) in Subjects with Gout", presented at American College of Rheumatology Annual Scientific Meeting on Oct. 16-21, 2004 at San Antonio, TX, Poster 807.

Sundy, J. et al., "Pharmacokinetics and Pharmacodynamics of Intravenous PEGylated Recombinant Mammalian Urate Oxidase in Patients With Refractory Gout." (2007) Arth. Rheum., vol. 56, No. 3, pp. 1021-1028.

Sundy, J. et al., "Quality of Life in Patients With Treatment-Failure Gout", presented at the EULAR—Annual European Congress of Rheumatology, on Jun. 21-24, 2006 at Amsterdam, Netherlands, Poster 517.

Sundy, J. et al., "Reduction of Plasma Urate Levels Following Treatment with Multiple Doses of Pegloticase in Patients with Treatment-Failure Gout" Arthritis & Rheumatism, vol. 58, No. 9, p. 2882-2891, (2008).

Sundy, J. et al., A Multicenter Longitudinal Study of Disease Characteristics in Patients With Treatment-Failure Gout, presented at the EULAR—Annual European Congress of Rheumatology, on Jun. 21-24, 2006 at Amsterdam, Netherlands, Poster 518.

Sundy, S. et al., Arthritis & Rheumatism, vol. 52, No. 9 (Supplement), Sep. 2005, Abstract Supplement, 2005 annual Scientific Meeting, Nov. 12-17, 2005, San Diego, California; Abstract #1836.

Sutterlin et al., "Mixtures of Quaternary Ammonium Compounds and Anionic Organic Compounds in the Aquatic environment: Elimination and Biodegradability in the Closed Bottle Test Monitored by LC-MS/MS", Chemosphere, 72(3), pp. 479-484, Abstract only, (2008).

(56) References Cited

OTHER PUBLICATIONS

Suzuki, H. and Verma, D., "Soybean Nodule-Specific Uricase (Nodulin-35) is Expressed and Assembled into a Functional Tetrameric Holoenzyme in *Escherichia coli*," Plant Physiol. 95:384-389, American Society of Plant Physiologists, United States (1991).
Takeda et al., "Construction of chimaeric processed immunoglobulin genes containing mouse variable and human constant region sequences," Nature, vol. 314, p. 452-454, Apr. 4, 1985.
Terkeltaub, R., "Gout", Clinical practice. N. Engl. J. Med. 2003, 349(17): 1647-1655.
Tla, S., et al., Urate oxidase from pig liver: biochemical and immunological properties, Prikl Biokhim Mikrobiol 14:533-542, Izdatesltvo Nauka, Russia (1978).
Tomanee, P. et al., "Fractionation of Protein, RNA, and Plasmid DNA in Centrifugal Precipitation Chromatography Using Cationic Surfactant CTAB Containing Inorganic Salts NaCl and NH4Cl." (2004) Published online Sep. 9, 2004 in Wiley InterScience. DOI: 10.1002/bit.20203.
Tomohiro, JP 2005-241424 (Sep. 8, 2005) English language mechanical translation provided.
Treuheit, M. et al., "Inverse Relationship of Protein Concentration and Aggregation," Pharm. Res. 19:511-516, Plenum Publishing Corporation, United States (Apr. 2002).
Truscoe, "Effect of Detergents on Extraction and Activity of Ox-Kidney Urate Oxidase", Enzymologia 33:119-32, (1967).
Truscoe, R., et al, "Effect of pH on extraction and activity of ox-kidney urate oxidase," Biochim. Biophys. Acta 89:179-182, Elsevier Publishing Co., Netherlands (1964).
Tsuji, J. and Hirose, K., "Studies on Antigenicity of the Polyethylene Glycol (PEG)-Modified Uriacse," Int. J. Immunopharmacol. 7(5):725-739, Elsevier Science (1985).
Tsunasawa, S. et al., "Amino-terminal Processing of Mutant Forms of Yeast Iso-1-cytochrome c, The Specificities of Methionine Aminopeptidase and Acetyltransferase", The Journal of Biological Chemistry, vol. 260, No. 9, Issue of May 10, pp. 5382-5391, (1985).
U.S. Appl. No. 09/370,084; Notice of Allowability dated Jan. 13, 2003.
U.S. Appl. No. 09/370,084; Office Action dated Mar. 21, 2001.
U.S. Appl. No. 09/370,084; Office Action dated May 29, 2002.
U.S. Appl. No. 09/370,084; Office Action dated Sep. 13, 2002.
U.S. Appl. No. 09/501,730; Advisory Action dated Nov. 17, 2003; 5 pages.
U.S. Appl. No. 09/501,730; Declaration of Merry R. Sherman, Ph.D. Under 37 C.F.R. Section 1.132 dated Sep. 20, 2002; 5 pages.
U.S. Appl. No. 09/501,730; Final Office Action dated May 22, 2002; 8 pages.
U.S. Appl. No. 09/501,730; Final Office Action dated Feb. 10, 2004; 8 pages.
U.S. Appl. No. 09/501,730; Final Office Action dated Jun. 18, 2003; 9 pages.
U.S. Appl. No. 09/501,730; Non-Final Office Action dated Apr. 6, 2001; 12 pages.
U.S. Appl. No. 09/501,730; Non-Final Office Action dated Dec. 3, 2002; 11 pages.
U.S. Appl. No. 09/501,730; Non-Final Office Action dated Dec. 5, 2001; 9 pages.
U.S. Appl. No. 09/501,730; Notice of Allowance dated Feb. 24, 2004; 6 pages.
U.S. Appl. No. 09/501,730; Notice of Allowance dated Jan. 13, 2004; 8 pages.
U.S. Appl. No. 09/501,730; Notice of Appeal dated Sep. 9, 2003; 1 page.
U.S. Appl. No. 09/501,730; Petition Decision dated Jul. 12, 2007.
U.S. Appl. No. 09/501,730; Supplemental Notice of Allowability dated Feb. 24, 2004.
U.S. Appl. No. 09/762,097; Final Office Action dated Aug. 1, 2005; 5 pages.
U.S. Appl. No. 09/762,097, filed Jun. 7, 2007.
U.S. Appl. No. 09/762,097; Non-Final Office Action dated Mar. 16, 2005; 6 pages.
U.S. Appl. No. 09/762,097; Non-Final Office Action dated Oct. 15, 2002; 8 pages.
U.S. Appl. No. 09/762,097; Non-Final Office Action dated Oct. 24, 2003; 6 pages.
U.S. Appl. No. 09/762,097; Notice of Allowance dated Nov. 21, 2005; 5 pages.
U.S. Appl. No. 09/839,946; Advisory Action dated Dec. 5, 2005; 9 pages.
U.S. Appl. No. 09/839,946; BPAI Decision decided on Jul. 18, 2007; 7 pages.
U.S. Appl. No. 09/839,946; Declaration of Merry R, Sherman Under 37 C.F.R. Section 1,132 dated May 26, 2005; 8 pages.
U.S. Appl. No. 09/839,946; Declaration of Merry R, Sherman Under 37 C.F.R. Section 1,132 dated Sep. 18, 2007; 19 pages.
U.S. Appl. No. 09/839,946; Final Office Action dated Jul. 20, 2005; 14 pages.
U.S. Appl. No. 09/839,946; Final Office Action dated Mar. 5, 2004; 9 pages.
U.S. Appl. No. 09/839,946; Final Office Action dated Jan. 2, 2009; 8 pages.
U.S. Appl. No. 09/839,946; Final Office Action dated Oct. 16, 2009; 8 pages.
U.S. Appl. No. 09/839,946; Non-Final Office Action dated Jan. 26, 2005; 12 pages.
U.S. Appl. No. 09/839,946; Non-Final Office Action dated Sep. 11, 2003; 12 pages.
U.S. Appl. No. 09/839,946; Non-Final Office Action dated Aug. 2, 2004; 7 pages.
U.S. Appl. No. 09/839,946; Non-Final Office Action dated Aug. 11, 2008; 6 pages.
U.S. Appl. No. 09/839,946; Non-Final Office Action dated Jul. 23, 2008; 7 pages.
U.S. Appl. No. 09/839,946; Non-Final Office Action dated May 11, 2009; 8 pages.
U.S. Appl. No. 09/839,946; Notice of Allowability dated Dec. 23, 2009; 5 pages.
U.S. Appl. No. 09/839,946; Notice of Appeal dated Dec. 20, 2005; 1 page.
U.S. Appl. No. 09/839,946; Notice of Hearing dated May 15, 2007; 1 page.
U.S. Appl. No. 09/839,946; Sherman et al., filed Apr. 19, 2001.
U.S. Appl. No. 10/928,370; Final Office Action dated Dec. 30, 2011; 10 pages.
U.S. Appl. No. 10/928,370; Final Office Action dated Aug. 5, 2010; 8 pages.
U.S. Appl. No. 10/928,370; Final Office Action dated Jun. 22, 2009;11 pages.
U.S. Appl. No. 10/928,370; Final Office Action dated Nov. 2, 2007; 15 pages.
U.S. Appl. No. 10/928,370; Non-Final Office Action dated Jun. 9, 2011; 14 pages.
U.S. Appl. No. 10/928,370; Non-Final Office Action dated Mar. 18, 2014; 9 pages.
U.S. Appl. No. 10/928,370; Non-Final Office Action dated Apr. 9, 2007; 14 pages.
U.S. Appl. No. 10/928,370; Non-Final Office Action dated Dec. 9, 2009; 11 pages.
U.S. Appl. No. 10/928,370; Non-Final Office Action dated Sep. 30, 2008; 9 pages.
U.S. Appl. No. 10/928,370; Notice of Appeal dated May 1, 2008; 1 page.
U.S. Appl. No. 11/357,028; Advisory Action dated Dec. 20, 2012; 4 pages.
U.S. Appl. No. 11/357,028; Advisory Action dated Jan. 15, 2008; 3 pages.
U.S. Appl. No. 11/357,028; Advisory Action dated Mar. 16, 2010; 3 pages.
U.S. Appl. No. 11/357,028; Advisory Action dated Mar. 18, 2009; 4 pages.
U.S. Appl. No. 11/357,028; Applicant Initiated Interview Summary dated Aug. 13, 2012; 3 pages.
U.S. Appl. No. 11/357,028; Applicant Initiated Interview Summary dated Feb. 12, 2013; 3 pages.

(56) References Cited

OTHER PUBLICATIONS

U.S. Appl. No. 11/357,028; Final Office Action dated Aug. 27, 2007; 11 pages.
U.S. Appl. No. 11/357,028; Final Office Action dated Dec. 31, 2008; 13 pages.
U.S. Appl. No. 11/357,028; Final Office Action dated Jan. 4, 2010; 14 pages.
U.S. Appl. No. 11/357,028; Final Office Action dated Jun. 8, 2012; 14 pages.
U.S. Appl. No. 11/357,028; Final Office Action dated Jun. 13, 2011; 8 pages.
U.S. Appl. No. 11/357,028; Non-Final Office Action dated Dec. 6, 2011; 13 pages.
U.S. Appl. No. 11/357,028; Non-Final Office Action dated Feb. 7, 2007; 9 pages.
U.S. Appl. No. 11/357,028; Non-Final Office Action dated Jul. 5, 2016; 4 pages.
U.S. Appl. No. 11/357,028; Non-Final Office Action dated Jul. 12, 2013; 9 pages.
U.S. Appl. No. 11/357,028; Non-Final Office Action dated Mar. 25, 2008; 10 pages.
U.S. Appl. No. 11/357,028; Non-Final Office Action dated May 29, 2009; 16 pages.
U.S. Appl. No. 11/357,028; Non-Final Office Action dated Oct. 13, 2010; 10 pages.
U.S. Appl. No. 11/357,028; Notice of Appeal dated Apr. 5, 2010; 1 page.
U.S. Appl. No. 11/357,028; Notice of Appeal dated Dec. 10, 2012; 1 page.
U.S. Appl. No. 11/539,475; Final Office Action dated Apr. 28, 2011; 9 pages.
U.S. Appl. No. 11/539,475; Final Office Action dated Oct. 30, 2009; 2 pages.
U.S. Appl. No. 11/539,475; Final Office Action dated Oct. 30, 2009; 6 pages.
U.S. Appl. No. 11/539,475; Non-Final Office Action dated Jun. 25, 2009; 6 pages.
U.S. Appl. No. 11/539,475; Non-Final Office Action dated Sep. 9, 2010; 7 pages.
U.S. Appl. No. 11/539,475; Notice of Allowance dated Oct. 19, 2011; 5 pages.
U.S. Appl. No. 11/833,590; Notice of Allowance dated Dec. 1, 2010; 9 pages.
U.S. Appl. No. 11/833,590; Office Action dated Mar. 22, 2010; 10 pages.
U.S. Appl. No. 11/882,750; Non-Final Office Action dated Mar. 17, 2010; 9 pages.
U.S. Appl. No. 11/882,750; Notice of Allowance dated Dec. 14, 2010; 6 pages.
U.S. Appl. No. 11/899,688; Final Office Action dated Jun. 24, 2010; 7 pages.
U.S. Appl. No. 11/899,688; Final Office Action dated Oct. 24, 2011; 5 pages.
U.S. Appl. No. 11/899,688; Non-Final Office Action dated May 6, 2011; 7 pages.
U.S. Appl. No. 11/899,688; Non-Final Office Action dated Oct. 30, 2009; 10 pages.
U.S. Appl. No. 11/918,292; Advisory Action dated Feb. 8, 2012; 3 pages.
U.S. Appl. No. 11/918,292; Applicant Initiated Interview Summary dated Jun. 13, 2016; 4 pages.
U.S. Appl. No. 11/918,292; Declaration of Meir Fischer Under 37 C.F.R Section 1.132 dated Aug. 17, 2011; 3 pages.
U.S. Appl. No. 11/918,292; Final Office Action dated Feb. 5, 2015; 10 pages.
U.S. Appl. No. 11/918,292; Final Office Action dated Nov. 3, 2011; 10 pages.
U.S. Appl. No. 11/918,292; Non-Final Office Action dated Feb. 17, 2011; 10 pages.
U.S. Appl. No. 11/918,292; Non-Final Office Action dated Feb. 19, 2016; 8 pages.
U.S. Appl. No. 11/918,292; Non-Final Office Action dated Jun. 12, 2014; 12 pages.
U.S. Appl. No. 11/918,292; Notice of Allowance dated Aug. 18, 2016; 7 pages.
U.S. Appl. No. 11/918,296; Notice of Allowance dated Jun. 7, 2010; 7 pages.
U.S. Appl. No. 11/918,297; Examiner Initiated Interview Summary dated Jan. 25, 2012; 1 page.
U.S. Appl. No. 11/918,297; Non-Final Office Action dated Aug. 26, 2011; 26 oages.
U.S. Appl. No. 11/918,297; Notice of Allowance dated Jan. 25, 2012; 10 pages.
U.S. Appl. No. 12/769,570; Non-Final Office Action dated Jan. 26, 2011; 9 pages.
U.S. Appl. No. 12/769,570; Notice of Allowance dated Jul. 18, 2011; 7 pages.
U.S. Appl. No. 12/769,572; Advisory Action dated May 2, 2012; 3 pages.
U.S. Appl. No. 12/769,572; Advisory Action dated May 6, 2015; 18 pages.
U.S. Appl. No. 12/769,572; Final Office Action dated Jan. 6, 2015; 16 pages.
U.S. Appl. No. 12/769,572; Final Office Action dated Dec. 4, 2013; 7 pages.
U.S. Appl. No. 12/769,572; Final Office Action dated Feb. 29, 2012; 6 pages.
U.S. Appl. No. 12/769,572; Final Office Action dated May 4, 2011; 6 pages.
U.S. Appl. No. 12/769,572; Non-Final Office Action dated Dec. 10, 2010; 8 pages.
U.S. Appl. No. 12/769,572; Non-Final Office Action dated Aug. 19, 2014; 9 pages.
U.S. Appl. No. 12/769,572; Non-Final Office Action dated Aug. 28, 2014; 10 pages.
U.S. Appl. No. 12/769,572; Non-Final Office Action dated Oct. 20, 2011; 6 pages.
U.S. Appl. No. 12/769,572; Non-Final Office Action dated May 9, 2013; 6 pages.
U.S. Appl. No. 12/769,572; Notice of Allowance dated Apr. 29, 2014; 7 pages.
U.S. Appl. No. 12/769,572; Office Action dated Apr. 29, 2014.
U.S. Appl. No. 12/879,084; Notice of Allowance dated Feb. 11, 2011; 7 pages.
U.S. Appl. No. 12/879,084; Notice of Allowance dated Feb. 22, 2011; 4 pages.
U.S. Appl. No. 13/083,152; Non-Final Office Action dated Apr. 2, 2013; 10 pages.
U.S. Appl. No. 13/083,152; Notice of Allowance dated Aug. 22, 2013; 8 pages.
U.S. Appl. No. 13/085,793; Final Office Action dated Oct. 10, 2012; 8 pages.
U.S. Appl. No. 13/085,793; Non-Final Office Action dated Jan. 3, 2014; 13 pages.
U.S. Appl. No. 13/085,793; Non-Final Office Action dated Mar. 14, 2012; 9 pages.
U.S. Appl. No. 13/085,793; Non-Final Office Action dated Oct. 3, 2011; 6 pages.
U.S. Appl. No. 13/085,793; Notice of Allowance dated Aug. 21, 2014; 7 pages.
U.S. Appl. No. 13/107,498; Notice of Allowance dated Jun. 14, 2011; 8 pages.
U.S. Appl. No. 13/226,891; Notice of Allowance dated Jan. 9, 2012; 7 pages.
U.S. Appl. No. 13/306,336; Final Office Action dated Apr. 22, 2015; 11 pages.
U.S. Appl. No. 13/306,336; Final Office Action dated Feb. 26, 2014; 11 pages.
U.S. Appl. No. 13/306,336; Non-Final Office Action dated Jun. 23, 2014; 9 pages.
U.S. Appl. No. 13/306,336; Non-Final Office Action dated Nov. 14, 2014; 11 pages.

(56) References Cited

OTHER PUBLICATIONS

U.S. Appl. No. 13/306,336; Non-Final Office Action dated Jul. 23, 2013; 9 pages.
U.S. Appl. No. 13/379,704; Applicant Initiated Interview Summary dated Jun. 23, 2015; 4 pages.
U.S. Appl. No. 13/379,704; Declaration of Theresa Rosario-Jansen and David Erick Wright Under 37 C.F.R. Section 1.132 dated Jul. 24, 2014; 4 pages.
U.S. Appl. No. 13/379,704; Examiner Initiated Interview Summary dated Jul. 5, 2013; 1 page.
U.S. Appl. No. 13/379,704; Examiner Initiated Interview Summary dated May 6, 2016; 1 page.
U.S. Appl. No. 13/379,704; Final Office Action dated Oct. 10, 2014; 16 pages.
U.S. Appl. No. 13/379,704; Final Office Action dated Oct. 20, 2015; 20 pages.
U.S. Appl. No. 13/379,704; Non-Final Office Action dated Feb. 11, 2015; 21 pages.
U.S. Appl. No. 13/379,704; Non-Final Office Action dated Feb. 25, 2014; 11 pages.
U.S. Appl. No. 13/379,704; Non-Final Office Action dated Jul. 5, 2013; 9 pages.
U.S. Appl. No. 13/379,704; Notice of Allowance dated May 6, 2016; 10 pages.
U.S. Appl. No. 13/452,151; Examiner Initiated Interview Summary dated Jun. 19, 2012; 1 page.
U.S. Appl. No. 13/452,151; Notice of Allowance dated Jun. 19, 2012; 7 pages.
U.S. Appl. No. 13/461,170; Non-Final Office Action dated Feb. 4, 2013; 10 pages.
U.S. Appl. No. 13/461,170; Notice of Allowance dated May 17, 2013; 8 pages.
U.S. Appl. No. 13/623,512; Examiner Initiated Interview Summary dated Feb. 19, 2013; 1 page.
U.S. Appl. No. 13/623,512; Notice of Allowance dated Feb. 19, 2013; 7 pages.
U.S. Appl. No. 13/972,167; Non-Final Office Action dated Aug. 4, 2014; 10 pages.
U.S. Appl. No. 13/972,167; Notice of Allowance dated Dec. 26, 2014; 9 pages.
U.S. Appl. No. 14/462,368; Applicant Initiated Interview Summary dated Jun. 2, 2016; 3 pages.
U.S. Appl. No. 14/462,368; Final Office Action dated Apr. 20, 2017; 40 pages.
U.S. Appl. No. 14/462,368; Non-Final Office Action dated Sep. 2, 2016; 19 pages.
U.S. Appl. No. 14/671,246; Non-Final Office Action dated Apr. 6, 2016; 10 pages.
U.S. Appl. No. 14/671,246; Notice of Allowance dated Jan. 19, 2017; 8 pages.
U.S. Appl. No. 14/671,246; Notice of Allowance dated Nov. 8, 2016; 9 pages.
U.S. Appl. No. 14/806,494; Notice of Allowance dated Jun. 13, 2017; 8 pages.
U.S. Appl. No. 14/806,494; Notice of Allowance dated Sep. 27, 2017; 7 pages.
U.S. Appl. No. 15/356,046; Non-Final Office Action dated Aug. 9, 2018; 68 pages.
U.S. Appl. No. 15/356,046; Non-Final Office Action dated Dec. 27, 2018; 37 pages.
U.S. Appl. No. 15/649,398; Applicant Initiated Interview Summary dated Nov. 2, 2017; 3 pages.
U.S. Appl. No. 15/649,398; Non-Final Office Action dated Aug. 16, 2017; 11 pages.
U.S. Appl. No. 15/649,462; Non-Final Office Action dated Oct. 13, 2017; 10 pages.
U.S. Appl. No. 15/649,462; Notice of Allowance dated Jan. 29, 2018; 9 pages.
U.S. Appl. No. 15/649,478; Final Office Action dated Feb. 1, 2018; 8 pages.
U.S. Appl. No. 15/649,478; Non-Final Office Action dated Oct. 16, 2017; 10 pages.
U.S. Appl. No. 15/649,478; Notice of Allowance dated May 10, 2018.
U.S. Appl. No. 15/649,478; Notice of Allowance dated May 10, 2018; 8 pages.
U.S. Appl. No. 15/649,478; Notice of Allowance dated Sep. 11, 2018; 28 pages.
U.S. Appl. No. 15/649,488; Applicant Initiated Interview Summary dated Nov. 2, 2017; 3 pages.
U.S. Appl. No. 15/649,488; Examiner Initiated Interview Summary dated Jan. 19, 2018; 2 pages.
U.S. Appl. No. 15/649,488; Non-Final Office Action dated Sep. 11, 2017; 11 pages.
U.S. Appl. No. 15/649,488; Notice of Allowance dated Jan. 19, 2018; 10 pages.
U.S. Appl. No. 15/906,839; Examiner Initiated Interview Summary dated May 14, 2018; 02 pages.
U.S. Appl. No. 15/906,839; Notice of Allowance dated May 14, 2018; 09 pages.
U.S. Appl. No. 16/195,446; Application as filed dated Nov. 19, 2018; 31 pages.
U.S. Trademark Registration No. 2,246,623, entitled "Puricase," filed Jul. 15, 1997, 1 page.
Varelas, J. et al., "Expression and Characterization of a Single Recombinant Proteoglycan Tandem Repeat Domain of Link Protein That Binds Zinc and Hyaluronate", Arch. Biochem. Biophys. 321 (1):21-30, (1995).
Venkataseshan, V. et al., "Acute Hyperuricemic Nephropathy and Rental Failure after Transplantation", Nephron 56:317-321, Karger AG, Switzerland, (1990).
Veronese, F. et al., "Introduction and Overview of Peptide and Protein Pegylation", Advanced Drug Delivery Reviews 2002, 54(4):453-456.
Veronese, F. et al., "New Synthetic Polymers for Enzyme and Liposome Modification", in: ACS Symposium Series 580, Poly(Ethylene Glycol) Chemistry and Biological Applications, Harris, J.M., and Zalipsky, S., eds., American Chemical Society, Washington, D.C., pp. 182-192, (1997).
Veronese, F. et al., "Surface Modification of Proteins. Activation of Monomethoxy-Polyethylene Glycols by Phenylchloroformates and Modification of Ribonuclease and Superoxide Dismutase," Appl. Biochem. Biotechnol. 11:141-152, The Humana Press, Inc., United States, (1985).
Veronese, F., "Branched and Linear Poly(Ethylene) Glycol: Influence of the Polymer Structure on Ezymological, Pharmacokinetic, and Immunological Properties of Protein Conjugates," Journal of Bioactive and Compatible Polymers 12:196-207, Tectonic Publishing Co., Inc., United States (1997).
Voet et al., Biochemistry, Second Edition, John Wiley & Sons, Inc., 1995, pp. 235-241.
Wallrath, L. et al., "Molecular Characterization of the *Drosophila melanogaster* rate Oxidase Gene, an Ecdysone-Repressible Gene Expressed Only in the Malpighian Tubules", Mol. Cell. Biol. 10:5114-5127, American Society for Microbiology, United States, (1990).
Waltrip, R. et al., "Pharmacokinetics and Pharmacodynamics of Peg-Uricase in Patients With Hyperuricemia and Treatment Failure Gout", presented at the EULAR—Annual European Congress of Rheumatology, on Jun. 13-16, 2007 at Barcelona, Spain, Poster 358.
Waltrip, R. et al., "Weekly Flare Burden Index: A New Metric for Evaluating Gout Treatment", Ann Rheum Dis 2007; 66 (Suppl II):624, Abstract 748.
Wang, L., and G. Marzluf, "Purification and Characterization of Uricase, a Nitrogen-Regulated Enzyme, from Neurospora crassa," Archs. Biochem. Biophys. 201:185-193, Academic Press, Inc., United States (1980).
Wang, X. et al., "Rat urate oxidase: cloning and structural analysis of the gene and 5'-flanking region", Gene 97:223-229, Elsevier Science Publishers B.V., The Netherlands, (1991).
Ward et al., "Building activities of a repertoire of single immunoglobulin variable domains secreted from *Escherichia coli*," Nature, vol. 341, p. 544-546, Oct. 12, 1989.

(56) References Cited

OTHER PUBLICATIONS

Watanabe, T., and Suga, T., "A Simple Purification Method for Rat Liver Urate Oxidase," Analytical Biochemistry 89(2):343-347, Academic Press, Inc., United States (1978).

Wortmann, R. et al., "Gout and Hyperuricemia", Kelley's Textbook of Rheumatology. Edited by Ruddy, S., Harris, E., Sledge, C., 6th edn. St. Louis: W.B. Saunders: 2001: 1339-1371.

Written Opinion on Application No. 201102592-1 dated Nov. 21, 2013.

Wu, X. et al., "Hyperuricemia and urate nephropathy in urate oxidase-deficient mice," Proc. Nat. Acad. Sci. USA 91:742-746, National Academy of Sciences, United States (1994).

Wu, X. et al., "Two Independent Mutational Events in the Loss of Urate Oxidase during Hominoid Evolution," J. Mol. Evol. 34:78-84, Springer-Verlag, Germany (1992).

Wu, X. et al., "Urate oxidase: primary structure and evolutionary implications," PNAS, USA, 86(23):9412-6, (1989).

Yamamoto, K., et al., "Nucleotide Sequence of the Uricase Gene from *Bacillus* sp. TB-90," J. Biochem. 119:80-84, Oxford University Press, England (1996).

Yamanaka, H. et al., "Optimal Range of Serum Urate Concentrations to Minimize Risk of Gouty Attacks during Anti-Hyperuricemic Treatment", Adv. Exp. Med. Biol. 1998, 431:13-18.

Yasuda, Y. et al., "Biochemical and Biopharmaceutical Properties of Macromolecular Conjugates of Uricase with Dextran Polyethylene Glycol," Chem. Pharm. Bull. 38(7):2053-2056, Pharmaceutical Society of Japan (1990).

Yeldandi, A. et al., "Human Urate Oxidase Gene: Cloning and Partial Sequence Analysis Reveal a Stop Codon within the Fifth Exon," Biochem. Biophys. Res. Commun. 171:641-646, Academic Press, United States (1990).

Yelverton et al., "Bacterial synthesis of a novel human leukocyte interferon," Nucleic Acids Research, vol. 9, No. 3, p. 731, 1981.

Yokoyama et al., "Rapid Extraction of Uricase from Candida Utilis Cells by Use of Reducing Agent Plus Surfactant", Enzyme Microb Technol, vol. 10, pp. 52-22, (1988).

Zhang, T. et al., "Affinity Extraction of BSA with Reversed Micellar System Composed of Unbound Cibacron Blue", Biotechnology Progress, vol. 15, issue 6, pp. 1078-1082, (1999).

Zhang, W. et al., "Forward and backward extraction of BSA using mixed reverse micellar system of CTAB and alkyl halides." (2002) Biochemical Engineering Journal 12 (2002) 1-5.

Richette, P. et al., "Rasburicase for Tophaceous Gout not Treatable with Allopurinol: An Exploratory Study", Rheurnatol., 34(10):2093-8, (2007).

U.S. Appl. No. 16/195,446; Non-Final Office Action, dated Oct. 2, 2019; 53 pages.

```
1    ATG--------------ACTTACAAAAAGAATGATGAGGTAGAGTTTGTCCGAACTGGC
1    M  -  -  -  -  -  -  T  Y  K  N  D  E  V  E  F  V  R  T  G

63   TATGGGAAGGATATGATAAAAGTTCTCCATATTCAGCGAGATGGAAAATATCACAGCATT
21   Y  G  K  D  M  I  K  V  L  H  I  Q  R  D  G  K  Y  H  S  I

121  AAAGAGGTGGCAACTACAGTGCAACTGACTTTGAGCTCCAAAAAAGATTACCTGCATGGA
41   K  E  V  A  T  T  V  Q  L  T  L  S  S  K  D  Y  L  H  G

181  GACAATTCAGATGTCATCCCTACAGACACCATCAAGAACACAGTTAATGTCCTGGCGAAG
61   D  N  S  D  V  I  P  T  D  T  I  K  N  T  V  N  V  L  A  K

241  TTCAAAGGCATCAAAAGCATAGAAACTTTTGCTGTGACTATCTGTGAGCATTTCCTTTCT
81   F  K  G  I  K  S  I  E  T  F  A  V  T  I  C  E  H  F  L  S

301  TCCTTCAAGCATGTCATCAGAGCTCAAGTCTATGTGGAAGAAGTTCCTTGGAAGCGTTTT
101  S  F  K  H  V  I  R  A  Q  V  Y  V  E  E  V  P  W  K  R  F

361  GAAAAGAATGGAGTTAAGCATGTCCATGCATTTATTTATACTCCTACTGGAACGCACTTC
121  E  K  N  G  V  K  H  V  H  A  F  I  Y  T  P  T  G  T  H  F

421  TGTGAGGTTGAACAGATAAGGAATGGACCTCCAGTCATTCATTCTGGAATCAAAGACCTA
141  C  E  V  E  Q  I  R  N  G  P  P  V  I  H  S  G  I  K  D  L

481  AAAGTCTTGAAAACAACCCAGTCTGGCTTTGAAGGATTCATCAAGGACCAGTTCACCACC
161  K  V  L  K  T  T  Q  S  G  F  E  G  F  I  K  D  Q  F  T  T

541  CTCCCTGAGGTGAAGGACCGGTGCTTTGCCACCCAAGTGTACTGCAAATGGCGCTACCAC
181  L  P  E  V  K  D  R  C  F  A  T  Q  V  Y  C  K  W  R  Y  H

601  CAGGGCAGAGATGTGGACTTTGAGGCCACCTGGGACACTGTTAGGAGCATTGTCCTGCAG
201  Q  G  R  D  V  D  F  E  A  T  W  D  T  V  R  S  I  V  L  Q
                    ApaI
                      |
661  AAATTTGCTGGGCCCTATGACAAAGGCGAGTACTCGCCCTCTGTCCAGAAGACACTCTAT
221  K  F  A  G  P  Y  D  K  G  E  Y  S  P  S  V  Q  K  T  L  Y

721  GACATCCAGGTGCTCACCCTGGGCCAGGTTCCTGAGATAGAAGATATGGAAATCAGCCTG
241  D  I  Q  V  L  T  L  G  Q  V  P  E  I  E  D  M  E  I  S  L

781  CCAAATATTCACTACTTAAACATAGACATGTCCAAAATGGGACTGATCAACAAGGAAGAG
261  P  N  I  H  Y  L  N  I  D  M  S  K  M  G  L  I  N  K  E  E
                           NdeI
                             |
841  GTCTTGCTACCTTTAGACAATCCATATGGAAAAATTACTGGTACAGTCAAGAGGAAGTTG
281  V  L  L  P  L  D  N  P  Y  G  K  I  T  G  T  V  K  R  K  L
                 EcoRI                    SpeI BamHI
                   |                        |    |
901  TCTTCAAGACTGTGAaagccgaattccagcacactggcggccgttactagtggatcc
301  S  S  R  L  *
```

Fig. 2

```
                        20                   40                   60
Pig       MAHYRNDYKKNDEVEFVRTGYGKDMIKVLHIQRDGKYHSIKEVATSVQLTLSSKKDYLHG
PBC-ΔNC   M------TYKKNDEVEFVRTGYGKDMIKVLHIQRDGKYHSIKEVATTVQLTLSSKKDYLHG
Pig-KS-ΔN M------TYKKNDEVEFVRTGYGKDMIKVLHIQRDGKYHSIKEVATTVQLTLSSKKDYLHG
                 *                                    *

80                   100                  120
Pig       DNSDVIPTDTIKNTVNVLAKFKGIKSIETFAVTICEHFLSSFKHVIRAQVYVEEVPWKRF
PBC-ΔNC   DNSDVIPTDTIKNTVNVLAKFKGIKSIETFAVTICEHFLSSFKHVIRAQVYVEEVPWKRF
Pig-KS-ΔN DNSDVIPTDTIKNTVNVLAKFKGIKSIETFAVTICEHFLSSFKHVIRAQVYVEEVPWKRF 140                  160                  180
Pig       EKNGVKHVHAFIYTPTGTHPCEVEQIRNGPPVIHSGIKDLKVLKTTQSGFEGFIKDQFTT
PBC-ΔNC   EKNGVKHVHAFIYTPTGTHPCEVEQIRNGPPVIHSGIKDLKVLKTTQSGFEGFIKDQFTT
Pig-KS-ΔN EKNGVKHVHAFIYTPTGTHPCEVEQIRNGPPVIHSGIKDLKVLKTTQSGFEGFIKDQFTT 200                  220                  240
Pig       LPEVKDRCFATQVYCKNRYHQGRDVDFEATNDTVRSIVLQKFAGPYDKGEYSPSVQKTLY
PBC-ΔNC   LPEVKDRCFATQVYCKNRYHQGRDVDFEATNDTVRSIVLQKFAGPYDKGEYSPSVQKTLY
Pig-KS-ΔN LPEVKDRCFATQVYCKNRYHQGRDVDFEATNDTVRSIVLQKFAGPYDKGEYSPSVQKTLY 260                  280                  300
Pig       DIQVLTLGQVPEIEDMEISLPNIHYLNIDMSKMGLINKEEVLLPLDNPYGRITGTVKRKL
PBC-ΔNC   DIQVLSLSRVPEIEDMEISLPNIHYFNIDMSKMGLINKEEVLLPLDNPYGKITGTVKRKL
Pig-KS-ΔN DIQVLTLGQVPEIEDMEISLPNIHYLNIDMSKMGLINKEEVLLPLDNPYGKITGTVKRKL
               * **                *                         *

Pig       TSRL
PBC-ΔNC   S---
Pig-KS-ΔN SSRL
          *
```

Fig. 3

SEQUENCE LISTING

<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      Pig Liver Uricase (sense) oligonucleotide

<400> SEQUENCE: 1
gcgcgaattc catggctcat taccgtaatg actaca                                    36

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      Pig Liver Uricase (antisense) oligonucleotide

<400> SEQUENCE: 2
gcgctctaga agcttccatg gtcacagcct tgaagtcagc                                40

```
<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      Baboon (D3H) Liver Uricase (sense) oligonucleotide

<400> SEQUENCE: 3
gcgcgaattc catggcccac taccataaca actat                              35

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      Baboon (D3H) Liver Uricase (antisense) oligonucleotide

<400> SEQUENCE: 4
gcgcccatgg tctagatcac agtcttgaag acaacttcct                         40

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      PBC-DeltaNC Uricase (sense) oligonucleotide

<400> SEQUENCE: 5
gcgcatatga cttacaaaaa gaatgatgag gtagag                             36

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      PBC-DeltaNC Uricase (antisense) oligonucleotide

<400> SEQUENCE: 6
ccgtctagat taagacaact tcctcttgac tgtaccagta attttccgt atgg           54

<210> SEQ ID NO 7
<211> LENGTH: 299
<212> TYPE: PRT
<213> ORGANISM: Artificial Sequence
<220> FEATURE:
<223> OTHER INFORMATION: Description of Artificial Sequence: Synthetic
      Pig-KS-DeltaN polypeptide

<400> SEQUENCE: 7

Met Thr Tyr Lys Lys Asn Asp Glu Val Glu Phe Val Arg Thr Gly Tyr
1               5                   10                  15

Gly Lys Asp Met Ile Lys Val Leu His Ile Gln Arg Asp Gly Lys Tyr
            20                  25                  30

His Ser Ile Lys Glu Val Ala Thr Thr Val Gln Leu Thr Leu Ser Ser
        35                  40                  45

Lys Lys Asp Tyr Leu His Gly Asp Asn Ser Asp Val Ile Pro Thr Asp
    50                  55                  60

Thr Ile Lys Asn Thr Val Asn Val Leu Ala Lys Phe Lys Gly Ile Lys
65                  70                  75                  80

Ser Ile Glu Thr Phe Ala Val Thr Ile Cys Glu His Phe Leu Ser Ser
                85                  90                  95
```

```
Phe Lys His Val Ile Arg Ala Gln Val Tyr Val Glu Val Pro Trp
            100                 105                 110

Lys Arg Phe Glu Lys Asn Gly Val Lys His Val His Ala Phe Ile Tyr
        115                 120                 125

Thr Pro Thr Gly Thr His Phe Cys Glu Val Glu Gln Ile Arg Asn Gly
    130                 135                 140

Pro Pro Val Ile His Ser Gly Ile Lys Asp Leu Lys Val Leu Lys Thr
145                 150                 155                 160

Thr Gln Ser Gly Phe Glu Gly Phe Ile Lys Asp Gln Phe Thr Thr Leu
                165                 170                 175

Pro Glu Val Lys Asp Arg Cys Phe Ala Thr Gln Val Tyr Cys Lys Trp
            180                 185                 190

Arg Tyr His Gln Gly Arg Asp Val Asp Phe Glu Ala Thr Trp Asp Thr
        195                 200                 205

Val Arg Ser Ile Val Leu Gln Lys Phe Ala Gly Pro Tyr Asp Lys Gly
    210                 215                 220

Glu Tyr Ser Pro Ser Val Gln Lys Thr Leu Tyr Asp Ile Gln Val Leu
225                 230                 235                 240

Thr Leu Gly Gln Val Pro Glu Ile Glu Asp Met Glu Ile Ser Leu Pro
                245                 250                 255

Asn Ile His Tyr Leu Asn Ile Asp Met Ser Lys Met Gly Leu Ile Asn
            260                 265                 270

Lys Glu Glu Val Leu Leu Pro Leu Asp Asn Pro Tyr Gly Lys Ile Thr
        275                 280                 285

Gly Thr Val Lys Arg Lys Leu Ser Ser Arg Leu
    290                 295

<210> SEQ ID NO 8
<211> LENGTH: 298
<212> TYPE: PRT
<213> ORGANISM: Artificial Sequence
<220> FEATURE:
<223> OTHER INFORMATION: Description of Artificial Sequence: Synthetic
      Pig-KS-DeltaN without starting Met polypeptide

<400> SEQUENCE: 8

Thr Tyr Lys Lys Asn Asp Glu Val Glu Phe Val Arg Thr Gly Tyr Gly
1               5                   10                  15

Lys Asp Met Ile Lys Val Leu His Ile Gln Arg Asp Gly Lys Tyr His
            20                  25                  30

Ser Ile Lys Glu Val Ala Thr Thr Val Gln Leu Thr Leu Ser Ser Lys
        35                  40                  45

Lys Asp Tyr Leu His Gly Asp Asn Ser Asp Val Ile Pro Thr Asp Thr
    50                  55                  60

Ile Lys Asn Thr Val Asn Val Leu Ala Lys Phe Lys Gly Ile Lys Ser
65                  70                  75                  80

Ile Glu Thr Phe Ala Val Thr Ile Cys Glu His Phe Leu Ser Ser Phe
                85                  90                  95

Lys His Val Ile Arg Ala Gln Val Tyr Val Glu Val Pro Trp Lys
            100                 105                 110

Arg Phe Glu Lys Asn Gly Val Lys His Val His Ala Phe Ile Tyr Thr
        115                 120                 125

Pro Thr Gly Thr His Phe Cys Glu Val Glu Gln Ile Arg Asn Gly Pro
    130                 135                 140

Pro Val Ile His Ser Gly Ile Lys Asp Leu Lys Val Leu Lys Thr Thr
```

Gln Ser Gly Phe Glu Gly Phe Ile Lys Asp Gln Phe Thr Thr Leu Pro
145                 150                 155                 160

Glu Val Lys Asp Arg Cys Phe Ala Thr Gln Val Tyr Cys Lys Trp Arg
            165                 170                 175

Tyr His Gln Gly Arg Asp Val Asp Phe Glu Ala Thr Trp Asp Thr Val
        180                 185                 190

Arg Ser Ile Val Leu Gln Lys Phe Ala Gly Pro Tyr Asp Lys Gly Glu
    195                 200                 205

Tyr Ser Pro Ser Val Gln Lys Thr Leu Tyr Asp Ile Gln Val Leu Thr
210                 215                 220

Leu Gly Gln Val Pro Glu Ile Glu Asp Met Glu Ile Ser Leu Pro Asn
225                 230                 235                 240

Ile His Tyr Leu Asn Ile Asp Met Ser Lys Met Gly Leu Ile Asn Lys
            245                 250                 255

Glu Glu Val Leu Leu Pro Leu Asp Asn Pro Tyr Gly Lys Ile Thr Gly
        260                 265                 270

Thr Val Lys Arg Lys Leu Ser Ser Arg Leu
    275                 280                 285

290                 295

<210> SEQ ID NO 9
<211> LENGTH: 897
<212> TYPE: DNA
<213> ORGANISM: Artificial Sequence
<220> FEATURE:
<223> OTHER INFORMATION: Description of Artificial Sequence: Synthetic
      Pig-KS-DeltaNA polynucleotide

<400> SEQUENCE: 9
atgacttaca aaaagaatga tgaggtagag tttgtccgaa ctggctatgg gaaggatatg      60
ataaaagttc tccatattca gcgagatgga aaatatcaca gcattaaaga ggtggcaact     120
acagtgcaac tgactttgag ctccaaaaaa gattacctgc atggagacaa ttcagatgtc     180
atccctacag acaccatcaa gaacacagtt aatgtcctgg cgaagttcaa aggcatcaaa     240
agcatagaaa cttttgctgt gactatctgt gagcatttcc tttcttcctt caagcatgtc     300
atcagagctc aagtctatgt ggaagaagtt ccttggaagc gttttgaaaa gaatggagtt     360
aagcatgtcc atgcatttat ttatactcct actggaacgc acttctgtga ggttgaacag     420
ataaggaatg gacctccagt cattcattct ggaatcaaag acctaaaagt cttgaaaaca     480
acccagtctg gctttgaagg attcatcaag gaccagttca ccaccctccc tgaggtgaag     540
gaccggtgct ttgccaccca agtgtactgc aaatggcgct accaccaggg cagagatgtg     600
gactttgagg ccacctggga cactgttagg agcattgtcc tgcagaaatt tgctgggccc     660
tatgacaaag gcgagtactc gccctctgtc cagaagacac tctatgacat ccaggtgctc     720
accctgggcc aggttcctga gatagaagat atggaaatca gcctgccaaa tattcactac     780
ttaaacatag acatgtccaa aatgggactg atcaacaagg aagaggtctt gctaccctta     840
gacaatccat atggaaaaat tactggtaca gtcaagagga gttgtcttc aagactg       897

<210> SEQ ID NO 10
<211> LENGTH: 894
<212> TYPE: DNA
<213> ORGANISM: Artificial Sequence
<220> FEATURE:
<223> OTHER INFORMATION: Description of Artificial Sequence: Synthetic
      Pig-KS-DeltaN without starting ATG polynucleotide

<400> SEQUENCE: 10

```
acttacaaaa agaatgatga ggtagagttt gtccgaactg ctatgggaa ggatatgata      60
aaagttctcc atattcagcg agatggaaaa tatcacagca ttaaagaggt ggcaactaca    120
gtgcaactga ctttgagctc caaaaaagat tacctgcatg gagacaattc agatgtcatc    180
cctacagaca ccatcaagaa cacagttaat gtcctggcga agttcaaagg catcaaaagc    240
atagaaactt ttgctgtgac tatctgtgag catttccttt cttccttcaa gcatgtcatc    300
agagctcaag tctatgtgga agaagttcct tggaagcgtt ttgaaaagaa tggagttaag    360
catgtccatg catttattta tactcctact ggaacgcact tctgtgaggt tgaacagata    420
aggaatggac ctccagtcat tcattctgga atcaaagacc taaagtctt gaaaacaacc     480
cagtctggct ttgaaggatt catcaaggac cagttcacca ccctccctga ggtgaaggac    540
cggtgctttg ccacccaagt gtactgcaaa tggcgctacc accagggcag agatgtggac    600
tttgaggcca cctgggacac tgttaggagc attgtcctgc agaaatttgc tgggccctat    660
gacaaaggcg agtactcgcc ctctgtccag aagacactct atgacatcca ggtgctcacc    720
ctgggccagg ttcctgagat agaagatatg gaaatcagcc tgccaaatat tcactactta    780
aacatagaca tgtccaaaat gggactgatc aacaaggaag aggtcttgct accttagac    840
aatccatatg gaaaaattac tggtacagtc aagaggaagt tgtcttcaag actg          894
```

<210> SEQ ID NO 11
<211> LENGTH: 304
<212> TYPE: PRT
<213> ORGANISM: Sus scrofa

<400> SEQUENCE: 11

```
Met Ala His Tyr Arg Asn Asp Tyr Lys Lys Asn Asp Glu Val Glu Phe
 1               5                  10                  15

Val Arg Thr Gly Tyr Gly Lys Asp Met Ile Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
        50                  55                  60

Val Ile Pro Thr Asp Thr Ile Lys Asn Thr Val Asn Val Leu Ala Lys
    65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
               100                 105                 110

Glu Glu Val Pro Trp Lys Arg Phe Glu Lys Asn Gly Val Lys His Val
           115                 120                 125

His Ala Phe Ile Tyr Thr Pro Thr Gly Thr His Phe Cys Glu Val Glu
       130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
               165                 170                 175

Gln Phe Thr Thr Leu Pro Glu Val Lys Asp Arg Cys Phe Ala Thr Gln
           180                 185                 190

Val Tyr Cys Lys Trp Arg Tyr His Gln Gly Arg Asp Val Asp Phe Glu
       195                 200                 205
```

```
Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
                260                 265                 270

Met Gly Leu Ile Asn Lys Glu Val Leu Leu Pro Leu Asp Asn Pro
            275                 280                 285

Tyr Gly Arg Ile Thr Gly Thr Val Lys Arg Lys Leu Thr Ser Arg Leu
    290                 295                 300

<210> SEQ ID NO 12
<211> LENGTH: 296
<212> TYPE: PRT
<213> ORGANISM: Artificial Sequence
<220> FEATURE:
<223> OTHER INFORMATION: Description of Artificial Sequence: Synthetic
      PBC-DeltaNC polypeptide

<400> SEQUENCE: 12

Met Thr Tyr Lys Lys Asn Asp Glu Val Glu Phe Val Arg Thr Gly Tyr
1               5                   10                  15

Gly Lys Asp Met Ile Lys Val Leu His Ile Gln Arg Asp Gly Lys Tyr
                20                  25                  30

His Ser Ile Lys Glu Val Ala Thr Thr Val Gln Leu Thr Leu Ser Ser
            35                  40                  45

Lys Lys Asp Tyr Leu His Gly Asp Asn Ser Asp Val Ile Pro Thr Asp
50                  55                  60

Thr Ile Lys Asn Thr Val Asn Val Leu Ala Lys Phe Lys Gly Ile Lys
65                  70                  75                  80

Ser Ile Glu Thr Phe Ala Val Thr Ile Cys Glu His Phe Leu Ser Ser
                85                  90                  95

Phe Lys His Val Ile Arg Ala Gln Val Tyr Val Glu Glu Val Pro Trp
                100                 105                 110

Lys Arg Phe Glu Lys Asn Gly Val Lys His Val His Ala Phe Ile Tyr
            115                 120                 125

Thr Pro Thr Gly Thr His Phe Cys Glu Val Gln Ile Arg Asn Gly
        130                 135                 140

Pro Pro Val Ile His Ser Gly Ile Lys Asp Leu Lys Val Leu Lys Thr
145                 150                 155                 160

Thr Gln Ser Gly Phe Glu Gly Phe Ile Lys Asp Gln Phe Thr Thr Leu
                165                 170                 175

Pro Glu Val Lys Asp Arg Cys Phe Ala Thr Gln Val Tyr Cys Lys Trp
                180                 185                 190

Arg Tyr His Gln Gly Arg Asp Val Asp Phe Glu Ala Thr Trp Asp Thr
            195                 200                 205

Val Arg Ser Ile Val Leu Gln Lys Phe Ala Gly Pro Tyr Asp Lys Gly
    210                 215                 220

Glu Tyr Ser Pro Ser Val Gln Lys Thr Leu Tyr Asp Ile Gln Val Leu
225                 230                 235                 240

Ser Leu Ser Arg Val Pro Glu Ile Glu Asp Met Glu Ile Ser Leu Pro
                245                 250                 255

Asn Ile His Tyr Phe Asn Ile Asp Met Ser Lys Met Gly Leu Ile Asn
                260                 265                 270
```

Lys Glu Glu Val Leu Leu Pro Leu Asp Asn Pro Tyr Gly Lys Ile Thr
            275                 280                 285

Gly Thr Val Lys Arg Lys Leu Ser
        290                 295

<210> SEQ ID NO 13
<211> LENGTH: 295
<212> TYPE: PRT
<213> ORGANISM: Artificial Sequence
<220> FEATURE:
<223> OTHER INFORMATION: Description of Artificial Sequence: Synthetic
      PBC-DeltaNC without starting Met polypeptide

<400> SEQUENCE: 13

Thr Tyr Lys Lys Asn Asp Glu Val Glu Phe Val Arg Thr Gly Tyr Gly
1               5                   10                  15

Lys Asp Met Ile Lys Val Leu His Ile Gln Arg Asp Gly Lys Tyr His
            20                  25                  30

Ser Ile Lys Glu Val Ala Thr Thr Val Gln Leu Thr Leu Ser Ser Lys
        35                  40                  45

Lys Asp Tyr Leu His Gly Asp Asn Ser Asp Val Ile Pro Thr Asp Thr
    50                  55                  60

Ile Lys Asn Thr Val Asn Val Leu Ala Lys Phe Lys Gly Ile Lys Ser
65                  70                  75                  80

Ile Glu Thr Phe Ala Val Thr Ile Cys Glu His Phe Leu Ser Ser Phe
                85                  90                  95

Lys His Val Ile Arg Ala Gln Val Tyr Val Glu Glu Val Pro Trp Lys
            100                 105                 110

Arg Phe Glu Lys Asn Gly Val Lys His Val His Ala Phe Ile Tyr Thr
        115                 120                 125

Pro Thr Gly Thr His Phe Cys Glu Val Glu Gln Ile Arg Asn Gly Pro
    130                 135                 140

Pro Val Ile His Ser Gly Ile Lys Asp Leu Lys Val Leu Lys Thr Thr
145                 150                 155                 160

Gln Ser Gly Phe Glu Gly Phe Ile Lys Asp Gln Phe Thr Thr Leu Pro
                165                 170                 175

Glu Val Lys Asp Arg Cys Phe Ala Thr Gln Val Tyr Cys Lys Trp Arg
            180                 185                 190

Tyr His Gln Gly Arg Asp Val Asp Phe Glu Ala Thr Trp Asp Thr Val
        195                 200                 205

Arg Ser Ile Val Leu Gln Lys Phe Ala Gly Pro Tyr Asp Lys Gly Glu
    210                 215                 220

Tyr Ser Pro Ser Val Gln Lys Thr Leu Tyr Asp Ile Gln Val Leu Ser
225                 230                 235                 240

Leu Ser Arg Val Pro Glu Ile Glu Asp Met Glu Ile Ser Leu Pro Asn
                245                 250                 255

Ile His Tyr Phe Asn Ile Asp Met Ser Lys Met Gly Leu Ile Asn Lys
            260                 265                 270

Glu Glu Val Leu Leu Pro Leu Asp Asn Pro Tyr Gly Lys Ile Thr Gly
        275                 280                 285

Thr Val Lys Arg Lys Leu Ser
    290                 295

<210> SEQ ID NO 14
<211> LENGTH: 13
<212> TYPE: PRT

<213> ORGANISM: Artificial Sequence
<220> FEATURE:
<223> OTHER INFORMATION: Description of Artificial Sequence: Synthetic
      PBC-DeltaNC (Fragment 44-56 of PBC-DeltaNC) peptide

<400> SEQUENCE: 14

Ala Thr Thr Val Gln Leu Thr Leu Ser Ser Lys Lys Asp
1               5                   10

<210> SEQ ID NO 15
<211> LENGTH: 936
<212> TYPE: DNA
<213> ORGANISM: Papio hamadryas

<400> SEQUENCE: 15

```
ccagaagaaa atggccgact accataacaa ctataaaaag aatgatgaat tggagtttgt      60
ccgaactggc tatgggaagg atatggtaaa agttctccat attcagcgag atggaaaata    120
tcacagcatt aaagaggtgg caacttcagt gcaacttact ctgagttcca aaaaagatta    180
cctgcatgga gataattcag atatcatccc tacagacacc atcaagaaca cagttcatgt    240
cttggcaaag tttaagggaa tcaaaagcat agaagccttt ggtgtgaata tttgtgagta    300
ttttcttttct tctttttaacc atgtaatccg agctcaagtc tacgtggaag aaatcccttg    360
gaagcgtctt gaaagaatg gagttaagca tgtccatgca tttattcaca ctcccactgg    420
aacacacttc tgtgaagttg aacaactgag aagtggaccc ccgtcatta cttctggaat    480
caaagacctc aaggtcttga aaacaacaca gtctggattt gaaggtttca tcaaggacca    540
gttcaccacc ctccctgagg tgaaggaccg atgctttgcc acccaagtgt actgcaagtg    600
gcgctaccac cagtgcaggg atgtggactt cgaggctacc tggggcacca ttcgggacct    660
tgtcctggag aaatttgctg ggccctatga caaaggcgag tactcaccct ctgtgcagaa    720
gaccctctat gatatccagg tgctctccct gagccgagtt cctgagatag aagatatgga    780
aatcagcctg ccaaacattc actacttcaa tatagacatg tccaaaatgg gtctgatcaa    840
caaggaagag gtcttgctgc cattagacaa tccatatgga aaaattactg gtacagtcaa    900
gaggaagttg tcttcaagac tgtgacattg tggcca                              936
```

<210> SEQ ID NO 16
<211> LENGTH: 304
<212> TYPE: PRT
<213> ORGANISM: Papio hamadryas

<400> SEQUENCE: 16

Met Ala Asp Tyr His Asn Asn Tyr Lys Lys Asn Asp Glu Leu Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu
                85                  90                  95

Tyr Phe Leu Ser Ser Phe Asn His Val Ile Arg Ala Gln Val Tyr Val
            100                 105                 110

```
Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile Thr Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Gly Thr Ile Arg Asp Leu Val Leu Glu Lys Phe Ala Gly
        210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
        290                 295                 300
```

VARIANT FORMS OF URATE OXIDASE AND USE THEREOF

CROSS REFERENCE TO RELATED APPLICATIONS

The present application is a continuation of U.S. application Ser. No. 15/649,478, filed on Jul. 13, 2017, now U.S. Pat. No. 10,160,958, which is a divisional application of U.S. application Ser. No. 15/490,736, filed on Apr. 18, 2017, which is a continuation of U.S. application Ser. No. 14/671, 246, filed on Mar. 27, 2015, now U.S. Pat. No. 9,670,467, which is a continuation of U.S. application Ser. No. 13/972, 167, filed on Aug. 21, 2013, now U.S. Pat. No. 9,017,980, which is a continuation of U.S. application Ser. No. 13/461, 170, filed May 1, 2012, now U.S. Pat. No. 8,541,205, which is a divisional application of U.S. application Ser. No. 11/918,297 filed Dec. 11, 2008, now U.S. Pat. No. 8,188, 224, which is a national stage filing of corresponding international application number PCT/US2006/013660, filed on Apr. 11, 2006, which claims priority to and benefit of U.S. provisional application Ser. No. 60/670,573, filed on Apr. 11, 2005, the disclosures of which are hereby incorporated by reference as if written herein in their entireties.

FIELD OF INVENTION

The present invention relates to genetically modified proteins with uricolytic activity. More specifically, the invention relates to proteins comprising truncated urate oxidases and methods for producing them.

BACKGROUND OF THE INVENTION

The terms urate oxidase and uricase are used herein interchangeably. Urate oxidases (uricases; E.C. 1.7.3.3) are enzymes which catalyze the oxidation of uric acid to a more soluble product, allantoin, a purine metabolite that is more readily excreted. Humans do not produce enzymatically active uricase, as a result of several mutations in the gene for uricase acquired during the evolution of higher primates. Wu, X, et al., (1992) *J Mol Evol* 34:78-84, incorporated herein by reference in its entirety. As a consequence, in susceptible individuals, excessive concentrations of uric acid in the blood (hyperuricemia) can lead to painful arthritis (gout), disfiguring urate deposits (tophi) and renal failure. In some affected individuals, available drugs such as allopurinol (an inhibitor of uric acid synthesis) produce treatment-limiting adverse effects or do not relieve these conditions adequately. Hande, K R, et al., (1984) *Am J Med* 76:47-56; Fam, A G, (1990) *Bailliere's Clin Rheumatol* 4:177-192, each incorporated herein by reference in its entirety. Injections of uricase can decrease hyperuricemia and hyperuricosuria, at least transiently. Since uricase is a foreign protein in humans, even the first injection of the unmodified protein from *Aspergillus flavus* has induced anaphylactic reactions in several percent of treated patients (Pui, C-H, et al., (1997) *Leukemia* 11:1813-1816, incorporated herein by reference in its entirety), and immunologic responses limit its utility for chronic or intermittent treatment. Donadio, D, et al., (1981) *Nouv Presse Med* 10:711-712; Leaustic, M, et al., (1983) *Rev Rhum Mal Osteoartic* 50:553-554, each incorporated herein by reference in its entirety.

The sub-optimal performance of available treatments for hyperuricemia has been recognized for several decades. Kissel, P, et al., (1968) *Nature* 217:72-74, incorporated herein by reference in its entirety. Similarly, the possibility that certain groups of patients with severe gout might benefit from a safe and effective form of injectable uricase has been recognized for many years. Davis, F F, et al., (1978) in G B Broun, et al., (Eds.) *Enzyme Engineering*, Vol. 4 (pp. 169-173) New York, Plenum Press; Nishimura, H, et al., (1979) *Enzyme* 24:261-264; Nishimura, H, et al., (1981) *Enzyme* 26:49-53; Davis, S, et al., (1981) *Lancet* 2(8241):281-283; Abuchowski, A, et al., (1981) *J Pharmacol Exp Ther* 219: 352-354; Chen, R H-L, et al., (1981) *Biochim Biophys Acta* 660:293-298; Chua, C C, et al., (1988) *Ann Int Med* 109: 114-117; Greenberg, M L, et al., (1989) *Anal Biochem* 176:290-293, each incorporated herein by reference in its entirety. Uricases derived from animal organs are nearly insoluble in solvents that are compatible with safe administration by injection. U.S. Pat. No. 3,616,231, incorporated herein by reference in its entirety. Certain uricases derived from plants or from microorganisms are more soluble in medically acceptable solvents. However, injection of the microbial enzymes quickly induces immunological responses that can lead to life-threatening allergic reactions or to inactivation and/or accelerated clearance of the uricase from the circulation. Donadio, et al., (1981); Leaustic, et al., (1983). Enzymes based on the deduced amino acid sequences of uricases from mammals, including pig and baboon, or from insects, such as, for example, *Drosophila melanogaster* or *Drosophila pseudoobscura* (Wallrath, L L, et al., (1990) *Mol Cell Biol* 10:5114-5127, incorporated herein by reference in its entirety), have not been suitable candidates for clinical use, due to problems of immunogenicity and insolubility at physiological pH.

Previously, investigators have used injected uricase to catalyze the conversion of uric acid to allantoin in vivo. See Pui, et al., (1997). This is the basis for the use in France and Italy of uricase from the fungus *Aspergillus flavus* (URICO-ZYME®) to prevent or temporarily correct the hyperuricemia associated with cytotoxic therapy for hematologic malignancies and to transiently reduce severe hyperuricemia in patients with gout. Potaux, L, et al., (1975) *Nouv Presse Med* 4:1109-1112; Legoux, R, et al., (1992) *J Biol Chem* 267:8565-8570; U.S. Pat. Nos. 5,382,518 and 5,541,098, each incorporated herein by reference in its entirety. Because of its short circulating lifetime, URICOZYME® requires daily injections. Furthermore, it is not well suited for long-term therapy because of its immunogenicity.

Certain uricases are useful for preparing conjugates with poly(ethylene glycol) or poly(ethylene oxide) (both referred to as PEG) to produce therapeutically efficacious forms of uricase having increased protein half-life and reduced immunogenicity. U.S. Pat. Nos. 4,179,337, 4,766,106, 4,847,325, and 6,576,235; U.S. Patent Application Publication US2003/0082786A1, each incorporated herein by reference in its entirety. Conjugates of uricase with polymers other than PEG have also been described. U.S. Pat. No. 4,460,683, incorporated herein by reference in its entirety.

In nearly all of the reported attempts to PEGylate uricase (i.e. to covalently couple PEG to uricase), the PEG is attached primarily to amino groups, including the amino-terminal residue and the available lysine residues. In the uricases commonly used, the total number of lysines in each of the four identical subunits is between 25 (*Aspergillus flavus* (U.S. Pat. No. 5,382,518, incorporated herein by reference in its entirety)) and 29 (pig (Wu, X, et al., (1989) *Proc Natl Acad Sci USA* 86:9412-9416, incorporated herein by reference in its entirety)). Some of the lysines are unavailable for PEGylation in the native conformation of the enzyme. The most common approach to reducing the immunogenicity of uricase has been to couple large numbers of strands of low molecular weight PEG. This has invariably resulted in large decreases in the enzymatic activity of the resultant conjugates.

A single intravenous injection of a preparation of *Candida utilis* uricase coupled to 5 kDa PEG reduced serum urate to undetectable levels in five human subjects whose average pre-injection serum urate concentration is 6.2 mg/dl, which is within the normal range. Davis, et al., (1981). The subjects were given an additional injection four weeks later, but their responses were not reported. No antibodies to uricase were detected following the second (and last) injection, using a relatively insensitive gel diffusion assay. This reference reported no results from chronic or subchronic treatments of human patients or experimental animals.

A preparation of uricase from *Arthrobacter protoformiae* coupled to 5 kDa PEG was used to temporarily control hyperuricemia in a single patient with lymphoma whose pre-injection serum urate concentration is 15 mg/dL. Chua, et al., (1988). Because of the critical condition of the patient and the short duration of treatment (four injections during 14 days), it is not possible to evaluate the long-term efficacy or safety of the conjugate.

Improved protection from immune recognition is enabled by modifying each uricase subunit with 2-10 strands of high molecular weight PEG (>5 kD-120 kD) Saifer, et al. (U.S. Pat. No. 6,576,235; (1994) Adv Exp Med Biol 366:377-387, each incorporated herein by reference in its entirety). This strategy enabled retention of >75% enzymatic activity of uricase from various species, following PEGylation, enhanced the circulating life of uricase, and enabled repeated injection of the enzyme without eliciting antibodies in mice and rabbits.

Hershfield and Kelly (International Patent Publication WO 00/08196; U.S. Application No. 60/095,489, incorporated herein by reference in its entirety) developed means for providing recombinant uricase proteins of mammalian species with optimal numbers of PEGylation sites. They used PCR techniques to increase the number of available lysine residues at selected points on the enzyme which is designed to enable reduced recognition by the immune system, after subsequent PEGylation, while substantially retaining the enzyme's uricolytic activity. Some of their uricase proteins are truncated at the carboxy and/or amino termini. They do not provide for directing other specific genetically-induced alterations in the protein.

In this application, the term "immunogenicity" refers to the induction of an immune response by an injected preparation of PEG-modified or unmodified uricase (the antigen), while "antigenicity" refers to the reaction of an antigen with preexisting antibodies. Collectively, antigenicity and immunogenicity are referred to as "immunoreactivity." In previous studies of PEG-uricase, immunoreactivity is assessed by a variety of methods, including: 1) the reaction in vitro of PEG-uricase with preformed antibodies; 2) measurements of induced antibody synthesis; and 3) accelerated clearance rates after repeated injections.

Previous attempts to eliminate the immunogenicity of uricases from several sources by coupling various numbers of strands of PEG through various linkers have met with limited success. PEG-uricases were first disclosed by F F Davis and by Y Inada and their colleagues. Davis, et al., (1978); U.S. Pat. No. 4,179,337; Nishimura, et al., (1979); Japanese Patents 55-99189 and 62-55079, each incorporated herein by reference in its entirety. The conjugate disclosed in U.S. Pat. No. 4,179,337 is synthesized by reacting uricase of unspecified origin with a 2,000-fold molar excess of 750 dalton PEG, indicating that a large number of polymer molecules is likely to have been attached to each uricase subunit. U.S. Pat. No. 4,179,337 discloses the coupling of either PEG or poly(propylene glycol) with molecular weights of 500 to 20,000 daltons, preferably about 500 to 5,000 daltons, to provide active, water-soluble, non-immunogenic conjugates of various polypeptide hormones and enzymes including oxidoreductases, of which uricase is one of three examples. In addition, U.S. Pat. No. 4,179,337 emphasizes the coupling of 10 to 100 polymer strands per molecule of enzyme, and the retention of at least 40% of enzymatic activity. No test results were reported for the extent of coupling of PEG to the available amino groups of uricase, the residual specific uricolytic activity, or the immunoreactivity of the conjugate.

In previous publications, significant decreases in uricolytic activity measured in vitro were caused by coupling various numbers of strands of PEG to uricase from *Candida utilis*. Coupling a large number of strands of 5 kDa PEG to porcine liver uricase gave similar results, as described in both the Chen publication and a symposium report by the same group. Chen, et al., (1981); Davis, et al., (1978).

In seven previous studies, the immunoreactivity of uricase is reported to be decreased by PEGylation and was eliminated in five other studies. In three of the latter five studies, the elimination of immunoreactivity is associated with profound decreases in uricolytic activity—to at most 15%, 28%, or 45% of the initial activity. Nishimura, et al., (1979) (15% activity); Chen, et al., (1981) (28% activity); Nishimura, et al., (1981) (45% activity). In the fourth report, PEG is reported to be coupled to 61% of the available lysine residues, but the residual specific activity is not stated. Abuchowski, et al., (1981). However, a research team that included two of the same scientists and used the same methods reported elsewhere that this extent of coupling left residual activity of only 23-28%. Chen, et al., (1981). The 1981 publications of Abuchowski et al., and Chen et al., indicate that to reduce the immunogenicity of uricase substantially, PEG must be coupled to approximately 60% of the available lysine residues. The fifth publication in which the immunoreactivity of uricase is reported to have been eliminated does not disclose the extent of PEG coupling, the residual uricolytic activity, or the nature of the PEG-protein linkage. Veronese, F M, et al., (1997) in J M Harris, et al., (Eds.), Poly(ethylene glycol) Chemistry and Biological Applications. ACS Symposium Series 680 (pp. 182-192) Washington, D.C.: American Chemical Society, incorporated herein by reference in its entirety.

Conjugation of PEG to a smaller fraction of the lysine residues in uricase reduced but did not eliminate its immunoreactivity in experimental animals. Tsuji, J, et al., (1985) *Int J Immunopharmacol* 7:725-730, incorporated herein by reference in its entirety (28-45% of the amino groups coupled); Yasuda, Y, et al., (1990) *Chem Pharm Bull* 38:2053-2056, incorporated herein by reference in its entirety (38% of the amino groups coupled). The residual uricolytic activities of the corresponding adducts ranged from <33% (Tsuji, et al.) to 60% (Yasuda, et al.) of their initial values. Tsuji, et al., synthesized PEG-uricase conjugates with 7.5 kDa and 10 kDa PEGs, in addition to 5 kDa PEG. All of the resultant conjugates are somewhat immunogenic and antigenic, while displaying markedly reduced enzymatic activities.

A PEGylated preparation of uricase from *Candida utilis* that is safely administered twice to each of five humans is reported to have retained only 11% of its initial activity. Davis, et al., (1981). Several years later, PEG-modified uricase from *Arthrobacter protoformiae* was administered four times to one patient with advanced lymphoma and severe hyperuricemia. Chua, et al., (1988). While the residual activity of that enzyme preparation was not measured, Chua, et al., demonstrated the absence of anti-uricase antibodies in the patient's serum 26 days after the first PEG-uricase injection, using an enzyme-linked immunosorbent assay (ELISA).

Previous studies of PEGylated uricase show that catalytic activity is markedly depressed by coupling a sufficient number of strands of PEG to decrease its immunoreactivity substantially. Furthermore, most previous preparations of PEG-uricase are synthesized using PEG activated with cyanuric chloride, a triazine derivative (2,4,6-trichloro-1,3,5-triazine) that has been shown to introduce new antigenic determinants and to induce the formation of antibodies in rabbits. Tsuji, et al., (1985).

Japanese Patent No. 3-148298 to A Sano, et al., incorporated herein by reference in its entirety, discloses modified proteins, including uricase, derivatized with PEG having a molecular weight of 1-12 kDa that show reduced antigenicity and "improved prolonged" action, and methods of making such derivatized peptides. However, there are no disclosures regarding strand counts, enzyme assays, biological tests or the meaning of "improved prolonged." Japanese Patents 55-99189 and 62-55079, each incorporated herein by reference in its entirety, both to Y Inada, disclose uricase conjugates prepared with PEG-triazine or bis-PEG-triazine (denoted as $PEG_2$), respectively. See Nishimura, et al., (1979 and 1981). In the first type of conjugate, the molecular weights of the PEGs are 2 kDa and 5 kDa, while in the second, only 5 kDa PEG is used. Nishimura, et al., (1979) reported the recovery of 15% of the uricolytic activity after modification of 43% of the available lysines with linear 5 kDa PEG, while Nishimura, et al., (1981) reported the recovery of 31% or 45% of the uricolytic activity after modification of 46% or 36% of the lysines, respectively, with $PEG_2$.

Previously studied uricase proteins were either natural or recombinant proteins. However, studies using SDS-PAGE and/or Western techniques revealed the presence of unexpected low molecular weight peptides which appear to be degradation products and increase in frequency over time. The present invention is related to mutant recombinant uricase proteins having truncations and enhanced structural stability.

SUMMARY OF THE INVENTION

The present invention provides novel recombinant uricase proteins. In one embodiment, the proteins of the invention contemplated are truncated and have mutated amino acids relative to naturally occurring uricase proteins. In particular embodiments, the mutations are at or around the areas of amino acids 7, 46, 291, and 301. Conservative mutations anywhere in the peptide are also contemplated as a part of the invention.

The subject invention provides a mutant recombinant uricase, wherein the uricase has been truncated by 1-20 amino acids and retains the uricolytic activity of the naturally occurring uricase. The truncations are at or around the sequence termini such that the protein may contain the ultimate amino acids. These mutations and truncations may enhance stability of the protein comprising such mutations.

In another embodiment, the present invention to provides a means for metabolizing uric acid comprising a novel recombinant uricase protein having uricolytic activity. Uricolytic activity is used herein to refer to the enzymatic conversion of uric acid to allantoin.

The subject invention further provides a host cell with the capacity for producing a uricase that has been truncated by 1-20 amino acids, and has mutated amino acids and retains uricolytic activity.

In an embodiment, an isolated truncated mammalian uricase is provided comprising a mammalian uricase amino acid sequence truncated at the amino terminus or the carboxy terminus or both the amino and carboxy termini by about 1-13 amino acids and further comprising an amino acid substitution at about position 46. In particular embodiments, the uricase comprises an amino terminal amino acid, wherein the amino terminal amino acid is alanine, glycine, proline, serine, or threonine. Also provided is a uricase wherein there is a substitution at about position 46 with threonine or alanine. In an embodiment, the uricase comprises the amino acid sequence of SEQ ID NO. 8. In an embodiment, the uricase is conjugated with a polymer to form, for example, a polyethylene glycol-uricase conjugate. In particular embodiments, polyethylene glycol-uricase conjugates comprise 2 to 12 polyethylene glycol molecules on each uricase subunit, preferably 3 to 10 polyethylene glycol molecules per uricase subunit. In particular embodiments, each polyethylene glycol molecule of the polyethylene glycol-uricase conjugate has a molecular weight between about 1 kD and 100 kD; about 1 kD and 50 kD; about 5 kD and 20 kD; or about 10 kD. Also provided are pharmaceutical compositions comprising the uricase of the invention, including the polyethylene glycol-uricase conjugate. In an embodiment, the pharmaceutical composition is suitable for repeated administration.

Also provided is a method of reducing uric acid levels in a biological fluid of a subject in need thereof, comprising administering the pharmaceutical composition comprising the uricase of the invention. In a particular embodiment, the biological fluid is blood.

In an embodiment, the uricase comprises a peptide having the sequence of position 44 to position 56 of Pig-KS-ΔN (SEQ ID NO. 14).

In an embodiment, the uricase protein comprises an N-terminal methionine. In a particular embodiment, the uricase comprises the amino acid sequence of SEQ ID NO. 7.

Also provided are isolated nucleic acids comprising a nucleic acid sequence which encodes a uricase of the invention, for example, uricases having or comprising the amino acid sequences of SEQ ID NO. 7, SEQ ID NO. 8, SEQ ID NO. 12 or SEQ ID NO. 13. In an embodiment, the isolated nucleic acid is operatively linked to a heterologous promoter, for example, the osmB promoter. Also provided are vectors comprising uricase encoding nucleic acids, and host cells comprising such vectors. In an embodiment, the nucleic acid has the sequence of SEQ ID NO. 7. Also provided is a method for producing a uricase comprising the steps of culturing such a host cell under conditions such that uricase is expressed by the host cell and isolating the expressed uricase.

BRIEF DESCRIPTION OF THE DRAWINGS

FIG. 2 depicts the DNA and the deduced amino acid sequences of Pig-KS-ΔN uricase (SEQ ID NO. 9 and SEQ ID NO. 7, respectively). The amino acid numbering in FIG. 2 is relative to the complete pig uricase sequence. Following the initiator methionine residue, a threonine replaces aspartic acid 7 of the pig uricase sequence. The restriction sites that are used for the various steps of subcloning are indicated. The 3' untranslated sequence is shown in lowercase letters. The translation stop codon is indicated by an asterisk.

FIG. 3 shows relative alignment of the deduced amino acid sequences of the various recombinant pig (SEQ ID NO. 11), PBC-ΔNC (SEQ ID NO. 12), and Pig-KS-ΔN (SEQ ID NO. 7) uricase sequences. The asterisks indicate the positions in which there are differences in amino acids in the Pig-KS-ΔN as compared to the published pig uricase sequence; the circles indicate positions in which there are differences in amino acids in Pig-KS-ΔN as compared to PBC-ΔN. Dashed lines indicate deletion of amino acids.

DETAILED DESCRIPTION OF THE INVENTION

Figure 1:
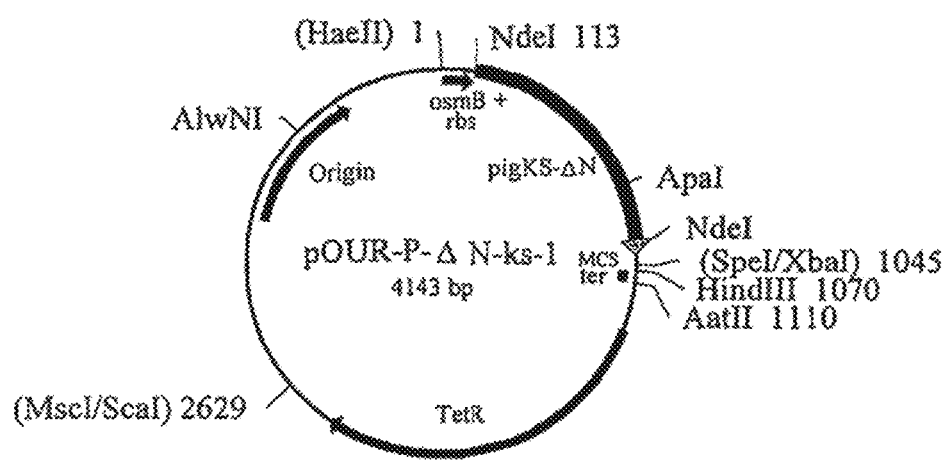
FIG. 1 illustrates the structure of plasmid pOUR-P-ΔN-ks-1. Numbers next to restriction sites indicate nucleotide position, relative to HaeII site, designated as 1. Restriction sites which are lost during cloning are marked in parenthesis.

Previous studies teach that when a significant reduction in the immunogenicity and/or antigenicity of uricase is achieved by PEGylation, it is invariably associated with a substantial loss of uricolytic activity. The safety, convenience and cost-effectiveness of biopharmaceuticals are all adversely impacted by decreases in their potencies and the resultant need to increase the administered dose. Thus, there is a need for a safe and effective alternative means for lowering elevated levels of uric acid in body fluids, including blood. The present invention provides a mutant recombinant uricase, wherein the uricase has been truncated by 1-20 amino acids at either the amino terminus or the carboxy terminus, or both, and substantially retains uricolytic activity of the naturally occurring uricase.

Uricase, as used herein, includes individual subunits, as well as the tetramer, unless otherwise indicated.

Mutated uricase, as used herein, refers to uricase molecules having amino acids exchanged with other amino acids.

A conservative mutation, as used herein, is a mutation of one or more amino acids, at or around a position, that does not substantially alter the protein's behavior. In a preferred embodiment, the uricase comprising at least one conservative mutation has the same uricase activity as does uricase without such mutation. In alternate embodiments, the uricase comprising at least one conservative mutation has substantially the same uricase activity, within 5% of the activity, within 10% of the activity, or within 30% of the activity of uricase without such mutation.

Conservative amino acid substitution is defined as a change in the amino acid composition by way of changing amino acids of a peptide, polypeptide or protein, or fragment thereof. In particular embodiments, the uricase has one, two, three or four conservative mutations. The substitution is of amino acids with generally similar properties (e.g., acidic, basic, aromatic, size, positively or negatively charged, polar, non-polar) such that the substitutions do not substantially alter peptide, polypeptide or protein characteristics (e.g., charge, IEF, affinity, avidity, conformation, solubility) or activity.

Typical substitutions that may be performed for such conservative amino acid substitution may be among the groups of amino acids as follows:
  glycine (G), alanine (A), valine (V), leucine (L) and isoleucine (I)
  aspartic acid (D) and glutamic acid (E)
  alanine (A), serine (S) and threonine (T)
  histidine (H), lysine (K) and arginine (R)
  asparagine (N) and glutamine (Q)
  phenylalanine (F), tyrosine (Y) and tryptophan (W)

The protein having one or more conservative substitutions retains its structural stability and can catalyze a reaction even though its DNA sequence is not the same as that of the original protein.

Truncated uricase, as used herein, refers to uricase molecules having shortened primary amino acid sequences. Amongst the possible truncations are truncations at or around the amino and/or carboxy termini. Specific truncations of this type may be such that the ultimate amino acids (those of the amino and/or carboxy terminus) of the naturally occurring protein are present in the truncated protein. Amino terminal truncations may begin at position 1, 2, 3, 4, 5 or 6. Preferably, the amino terminal truncations begin at position 2, thereby leaving the amino terminal methionine. This methionine may be removed by post-translational modification. In particular embodiments, the amino terminal methionine is removed after the uricase is produced. In a particular embodiment, the methionine is removed by endogenous bacterial aminopeptidase.

A truncated uricase, with respect to the full length sequence, has one or more amino acid sequences excluded. A protein comprising a truncated uricase may include any amino acid sequence in addition to the truncated uricase sequence, but does not include a protein comprising a uricase sequence containing any additional sequential wild type amino acid sequence. In other words, a protein comprising a truncated uricase wherein the truncation begins at position 6 (i.e., the truncated uricase begins at position 7) does not have, immediately upstream from the truncated uricase, whatever amino acid that the wild type uricase has at position 6.

Unless otherwise indicated by specific reference to another sequence or a particular SEQ ID NO., reference to the numbered positions of the amino acids of the uricases described herein is made with respect to the numbering of the amino acids of the pig uricase sequence. The amino acid sequence of pig uricase and the numbered positions of the amino acids comprising that sequence may be found in FIG. 3. As used herein, reference to amino acids or nucleic acids "from position X to position Y" means the contiguous sequence beginning at position X and ending at position Y, including the amino acids or nucleic acids at both positions X and Y.

Uricase genes and proteins have been identified in several mammalian species, for example, pig, baboon, rat, rabbit, mouse, and rhesus monkey. The sequences of various uricase proteins are described herein by reference to their public data base accession numbers, as follows: gi|50403728|sp|P25689; gi|20513634|dbj|BAB91555.1; gi|176610|AAA35395.1; gi|20513654|dbj|BAB91557.1; gi|47523606|ref|NP_999435.1; gi|6678509|ref|NP_033500.1; gi|57463|emb|CAA31490.1; gi|20127395|ref|NP_446220.1; gi|137107|sp|P11645; gi|51458661|ref|XP_497688.1; gi|207619|gb|AAA42318.1; gi|26340770|dbj|BAC34047.1; and gi|57459|emb|CAA30378.1. Each of these sequences and their annotations in the public databases accessible through the National Center for Biotechnology Information (NCBI) is incorporated by reference in its entirety.

In an embodiment of the invention, the uricase is truncated by 4-13 amino acids at its amino terminus. In an embodiment of the invention, the uricase is truncated by 4-13 amino acids at its carboxy terminus. In an embodiment of the invention, the uricase is truncated by 4-13 amino acids at both its carboxy and amino termini.

In an embodiment of the invention, the uricase is truncated by 6 amino acids at its amino terminus. In an embodiment of the invention, the uricase is truncated by 6 amino acids at its carboxy terminus. In an embodiment of the invention, the uricase is truncated by 6 amino acids at both its carboxy and amino termini.

In a particular embodiment, the uricase protein comprises the amino acid sequence from position 13 to position 292 of the amino acid sequence of pig uricase (SEQ ID NO. 11). In a particular embodiment, the uricase protein comprises the amino acid sequence from position 8 to position 287 of the amino acid sequence of PBC-ΔNC (SEQ ID NO. 12). In a particular embodiment, the uricase protein comprises the amino acid sequence from position 8 to position 287 of the amino acid sequence of Pig-KS-ΔN (SEQ ID NO. 7).

In another embodiment, the uricase protein comprises the amino acid sequence from position 44 to position 56 of Pig-KS-ΔN (SEQ ID NO. 14). This region of uricase has homology to sequences within the tunneling fold (T-fold) domain of uricase, and has within it a mutation at position 46 with respect to the native pig uricase sequence. This mutation surprisingly does not significantly alter the uricase activity of the protein.

In an embodiment of the invention, amino acids at or around any of amino acids 7, 46, and 291, and 301 are mutated. In a preferred embodiment of the invention, amino acids 7, 46, and 291, and 301, themselves, are mutated.

In particular embodiments, the protein is encoded by a nucleic acid that encodes an N-terminal methionine. Preferably, the N-terminal methionine is followed by a codon that allows for removal of this N-terminal methionine by bacterial methionine aminopeptidase (MAP). (Ben-Bassat and Bauer (1987) Nature 326:315, incorporated herein by reference in its entirety). Amino acids allowing the most complete removal of the N-terminal methionine are alanine, glycine, proline, serine, and threonine.

In an embodiment of the invention, the amino acids at or around positions 7 and/or 46 are substituted by threonine. Surprisingly, the enzymatic activity of truncated uricases prepared with these mutations is similar to that of the non-truncated enzyme. In a further embodiment of the invention, the amino acid mutations comprise threonine, threonine, lysine, and serine, at positions 7, 46, 291, and 301, respectively.

The truncated mammalian uricases disclosed herein may further comprise a methionine at the amino terminus. The penultimate amino acid may one that allows removal of the N-terminal methionine by bacterial methionine aminopeptidase (MAP). Amino acids allowing the most complete removal of the N-terminal methionine are alanine, glycine, proline, serine, and threonine. In a particular embodiment, the uricase comprises two amino terminal amino acids, wherein the two amino terminal amino acids are a methionine followed by an amino acid selected from the group consisting of alanine, glycine, proline, serine, and threonine.

In another embodiment of the invention, the substituted amino acids have been replaced by threonine.

In an embodiment of the invention, the uricase is a mammalian uricase.

In an embodiment of the invention, the mammalian uricase comprises the sequence of porcine, bovine, ovine or baboon liver uricase.

In an embodiment of the invention, the uricase is a chimeric uricase of two or more mammalian uricases.

In an embodiment of the invention, the mammalian uricases are selected from porcine, bovine, ovine, or baboon liver uricase.

In an embodiment of the invention, the uricase comprises the sequence of SEQ ID NO. 8.

In another embodiment of the invention, the uricase comprises the sequence of SEQ ID NO. 13.

The subject invention provides uricase encoding nucleic acids comprising the sequence of SEQ ID NO. 10.

In an embodiment of the invention, the uricase comprises fungal or microbial uricase.

In an embodiment of the invention, the fungal or microbial uricase is *Aspergillus flavus, Arthrobacter globiformis* or *Candida utilis* uricase.

In an embodiment of the invention, the uricase comprises an invertebrate uricase.

In an embodiment of the invention, the invertebrate uricase *Drosophila melanogaster* or *Drosophila pseudoobscura* uricase.

In an embodiment of the invention, the uricase comprises plant uricase.

In an embodiment of the invention, the plant uricase is *Glycine max* uricase of root nodules.

The subject invention provides a nucleic acid sequence encoding the uricase.

The subject invention provides a vector comprising the nucleic acid sequence.

In a particular embodiment, the uricase is isolated. In a particular embodiment, the uricase is purified. In particular embodiments, the uricase is isolated and purified.

The subject invention provides a host cell comprising a vector.

The subject invention provides a method for producing the nucleic acid sequence, comprising modification by PCR (polymerase chain reaction) techniques of a nucleic acid sequence encoding a nontruncated uricase. One skilled in the art knows that a desired nucleic acid sequence is prepared by PCR via synthetic oligonucleotide primers, which are complementary to regions of the target DNA (one for each strand) to be amplified. The primers are added to the target DNA (that need not be pure), in the presence of excess deoxynucleotides and Taq polymerase, a heat stable DNA polymerase. In a series (typically 30) of temperature cycles, the target DNA is repeatedly denatured (around 90° C.), annealed to the primers (typically at 50-60° C.) and a daughter strand extended from the primers (72° C.). As the daughter strands themselves act as templates for subsequent cycles, DNA fragments matching both primers are amplified exponentially, rather than linearly.

The subject invention provides a method for producing a mutant recombinant uricase comprising transfecting a host cell with the vector, wherein the host cell expresses the uricase, isolating the mutant recombinant uricase from the host cell, isolating the purified mutant recombinant uricase using, for example, chromatographic techniques, and purifying the mutant recombinant uricase. For example, the uricase can be made according to the methods described in International Patent Publication No. WO 00/08196, incorporated herein by reference in its entirety.

The uricase may be isolated and/or purified by any method known to those of skill in the art. Expressed polypeptides of this invention are generally isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography. The uricase is preferably isolated using a cationic surfactant, for example, cetyl pyridinium chloride (CPC) according to the method described in copending United States patent application filed on Apr. 11, 2005 having application No. 60/670,520, entitled Purification Of Proteins With Cationic Surfactant, incorporated herein by reference in its entirety.

In a preferred embodiment, the host cell is treated so as to cause the expression of the mutant recombinant uricase. One skilled in the art knows that transfection of cells with a vector is usually accomplished using DNA precipitated with calcium ions, though a variety of other methods can be used (e.g. electroporation).

In an embodiment of the invention, the vector is under the control of an osmotic pressure sensitive promoter. A promoter is a region of DNA to which RNA polymerase binds before initiating the transcription of DNA into RNA. An osmotic pressure sensitive promoter initiates transcription as a result of increased osmotic pressure as sensed by the cell.

In an embodiment of the invention, the promoter is a modified osmB promoter.

In particular embodiments, the uricase of the invention is a uricase conjugated with a polymer.

In an embodiment of the invention, a pharmaceutical composition comprising the uricase is provided. In one embodiment, the composition is a solution of uricase. In a preferred embodiment, the solution is sterile and suitable for injection. In one embodiment, such composition comprises uricase as a solution in phosphate buffered saline. In one embodiment, the composition is provided in a vial, optionally having a rubber injection stopper. In particular embodiments, the composition comprises uricase in solution at a concentration of from 2 to 16 milligrams of uricase per milliliter of solution, from 4 to 12 milligrams per milliliter or from 6 to 10 milligrams per milliliter. In a preferred embodiment, the composition comprises uricase at a concentration of 8 milligrams per milliliter. Preferably, the mass of uricase is measured with respect to the protein mass.

Effective administration regimens of the compositions of the invention may be determined by one of skill in the art. Suitable indicators for assessing effectiveness of a given regimen are known to those of skill in the art. Examples of such indicators include normalization or lowering of plasma uric acid levels (PUA) and lowering or maintenance of PUA to 6.8 mg/dL or less, preferably 6 mg/dL or less. In a preferred embodiment, the subject being treated with the composition of the invention has a PUA of 6 mg/ml or less for at least 70%, at least 80%, or at least 90% of the total treatment period. For example, for a 24 week treatment period, the subject preferably has a PUA of 6 mg/ml or less for at least 80% of the 24 week treatment period, i.e., for at least a time equal to the amount of time in 134.4 days (24 weeks×7 days/week×0.8=134.4 days).

In particular embodiments, 0.5 to 24 mg of uricase in solution is administered once every 2 to 4 weeks. The uricase may be administered in any appropriate way known to one of skill in the art, for example, intravenously, intramuscularly or subcutaneously. Preferably, when the administration is intravenous, 0.5 mg to 12 mg of uricase is administered. Preferably, when the administration is subcutaneous, 4 to 24 mg of uricase is administered. In a preferred embodiment, the uricase is administered by intravenous infusion over a 30 to 240 minute period. In one embodiment, 8 mg of uricase is administered once every two weeks. In particular embodiments, the infusion can be performed using 100 to 500 mL of saline solution. In a preferred embodiment, 8 mg of uricase in solution is administered over a 120 minute period once every 2 weeks or once every 4 weeks; preferably the uricase is dissolved in 250 mL of saline solution for infusion. In particular embodiments, the uricase administrations take place over a treatment period of 3 months, 6 months, 8 months or 12 months. In other embodiments, the treatment period is 12 weeks, 24 weeks, 36 weeks or 48 weeks. In a particular embodiment, the treatment period is for an extended period of time, e.g., 2 years or longer, for up to the life of subject being treated. In addition, multiple treatment periods may be utilized interspersed with times of no treatment, e.g., 6 months of treatment followed by 3 months without treatment, followed by 6 additional months of treatment, etc.

In certain embodiments, anti-inflammatory compounds may be prophylactically administered to eliminate or reduce the occurrence of infusion reactions due to the administration of uricase. In one embodiment, at least one corticosteroid, at least one antihistamine, at least one NSAID, or combinations thereof are so administered. Useful corticosteroids include betamethasone, budesonide, cortisone, dexamethasone, hydrocortisone, methylprednisolone, prednisolone, prednisone and triamcinolone. Useful NSAIDs include ibuprofen, indomethacin, naproxen, aspirin, acetominophen, celecoxib and valdecoxib. Useful antihistamines include azatadine, brompheniramine, cetirizine, chlorpheniramine, clemastine, cyproheptadine, desloratadine, dexchlorpheniramine, dimenhydrinate, diphenhydramine, doxylamine, fexofenadine, hydroxyzine, loratadine and phenindamine.

In a preferred embodiment, the antihistamine is fexofenadine, the NSAID is acetaminophen and the corticosteroid is hydrocortisone and/or prednisone. Preferably, a combination of all three (not necessarily concomitantly) are administered prior to infusion of the uricase solution. In a preferred embodiment, the NSAID and antihistamine are administered orally 1 to 4 hours prior to uricase infusion. A suitable dose of fexofenadine includes about 30 to about 180 mg, about 40 to about 150 mg, about 50 to about 120 mg, about 60 to about 90 mg, about 60 mg, preferably 60 mg. A suitable dose of acetaminophen includes about 500 to about 1500 mg, about 700 to about 1200 mg, about 800 to about 1100 mg, about 1000 mg, preferably 1000 mg. A suitable dose of hydrocortisone includes about 100 to about 500 mg, about 150 to about 300 mg, about 200 mg, preferably 200 mg. In one embodiment, the antihistamine is not diphenhydramine. In another embodiment, the NSAID is not acetaminophen. In a preferred embodiment, 60 mg fexofenadine is administered orally the night before uricase infusion; 60 mg fexofenadine and 1000 mg of acetaminophen are administered orally the next morning, and finally, 200 mg hydrocortisone is administered just prior to the infusion of the uricase solution. In one embodiment, prednisone is administered the day, preferably in the evening, prior to uricase administration. An appropriate dosage of prednisone includes 5 to 50 mg, preferably 20 mg. In certain embodiments, these prophylactic treatments to eliminate or reduce the occurrence of infusion reactions are utilized for subjects receiving or about to receive uricase, including PEGylated uricase and non-PEGylated uricase. In particular embodiments, these prophylactic treatments are utilized for subjects receiving or about to receive therapeutic peptides other than uricase, wherein the other therapeutic peptides are PEGylated or non-PEGylated.

In an embodiment of the invention, the pharmaceutical composition comprises a uricase that has been modified by conjugation with a polymer, and the modified uricase retains uricolytic activity. In a particular embodiment, polymer-uricase conjugates are prepared as described in International Patent Publication No. WO 01/59078 and U.S. application Ser. No. 09/501,730, incorporated herein by reference in their entireties.

In an embodiment of the invention, the polymer is selected from the group comprising polyethylene glycol, dextran, polypropylene glycol, hydroxypropylmethyl cellulose, carboxymethylcellulose, polyvinyl pyrrolidone, and polyvinyl alcohol.

In an embodiment of the invention, the composition comprises 2-12 polymer molecules on each uricase subunit, preferably 3 to 10 polymer molecules per uricase subunit.

In an embodiment of the invention, each polymer molecule has a molecular weight between about 1 kD and about 100 kD.

In another embodiment of the invention, each polymer molecule has a molecular weight between about 1 kD and about 50 kD. In a preferred embodiment of the invention, each polymer molecule has a molecular weight of between about 5 kD and about 20 kD, about 8 kD and about 15 kD, about 10 kD and 12 kD, preferably about 10 kD. In a preferred embodiment, each polymer molecule has a molecular weight of about 5 kD or about 20 kD. In an especially preferred embodiment of the invention, each polymer molecule has a molecular weight of 10 kD. Mixtures of different weight molecules are also contemplated. In an embodiment of the invention, the composition is suitable for repeated administration of the composition.

In a particular embodiment, conjugation of the uricase to the polymer comprises linkages selected from the group consisting of urethane linkages, secondary amine linkages, and amide linkages.

The subject invention provides a cell with the capacity for producing a uricase having an amino acid sequence of recombinant uricase, wherein the uricase has been truncated by 1-20 amino acids, and has mutated amino acids and uricolytic activity.

The subject invention provides a means for metabolizing uric acid using the uricase.

The subject invention provides a use of a composition of uricase for reducing uric acid levels in a biological fluid.

In an embodiment of the invention, the composition of uricase is used for reducing uric acid in a biological fluid comprising blood.

Also provided are novel nucleic acid molecules encoding uricase polypeptides.

The manipulations which result in their production are well known to the one of skill in the art. For example, uricase nucleic acid sequences can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a uricase, care should be taken to ensure that the modified gene remains within the appropriate translational reading frame, uninterrupted by translational stop signals. Additionally, the uricase-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, *J. Biol. Chem* 253:6551), use of TAB® linkers (Pharmacia) (as described in U.S. Pat. No. 4,719, 179), etc.

The nucleotide sequence coding for a uricase protein can be inserted into an appropriate expression vector, i.e., a vector which contains the necessary elements for the transcription and translation of the inserted protein-coding sequence. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities.

Depending on the host-vector system utilized, any one of a number of suitable transcription and translation elements may be used.

Any of the methods known for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding uricase protein may be regulated by a second nucleic acid sequence so that uricase protein is expressed in a host transformed with the recombinant DNA molecule. For example, expression of uricase may be controlled by any promoter/enhancer element known in the art. Promoters which may be used to control uricase expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); prokaryotic expression vectors such as the 3-lactamase promoter (Villa-Kamaroff, et al., 1978, Proc. Natl. Acad. Sci. U.S.A. 75:3727-3731), the tac promoter (DeBoer, et al., 1983, Proc. Natl. Acad. Sci. U.S.A. 80:21-25), and the osmB promoter. In particular embodiments, the nucleic acid comprises a nucleic acid sequence encoding the uricase operatively linked to a heterologous promoter.

Once a particular recombinant DNA molecule comprising a nucleic acid sequence encoding is prepared and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered uricase protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. Different vector/host expression systems may effect processing reactions such as proteolytic cleavages to different extents.

In particular embodiments of the invention, expression of uricase in E. coli is preferably performed using vectors which comprise the osmB promoter.

EXAMPLES

Example 1

Construction of Gene and Expression Plasmid for Uricase Expression

Recombinant porcine uricase (urate oxidase), Pig-KS-ΔN (amino terminus truncated pig uricase protein replacing amino acids 291 and 301 with lysine and serine, respectively) was expressed in E. coli K-12 strain W3 110 F–. A series of plasmids was constructed culminating in pOUR-P-ΔN-ks-1, which upon transformation of the E. coli host cells was capable of directing efficient expression of uricase. Isolation and Subcloning of Uricase cDNA from Pig and Baboon Liver Uricase cDNAs were prepared from pig and baboon livers by isolation and subcloning of the relevant RNA. Total cellular RNA was extracted from pig and baboon livers (Erlich, H. A. (1989). PCR Technology; Principles and Application for DNA Amplification; Sambrook, J., et al. (1989). Molecular Cloning: A Laboratory Manual, 2nd edition; Ausubel, F. M. et al. (1998). Current protocols in molecular Biology), then reverse-transcribed using the First-Strand cDNA Synthesis Kit (Pharmacia Biotech). PCR amplification was performed using Taq DNA polymerase (Gibco BRL, Life Technologies).

The synthetic oligonucleotide primers used for PCR amplification of pig and baboon urate oxidases (uricase) are shown in Table 1.

TABLE 1

Primers For PCR Amplification Of Uricase cDNA

Pig liver uricase:
sense
(SEQ ID NO. 1)
5' gcgcgaattccATGGCTCATTACCGTAATGACTACA 3' anti-sense
(SEQ ID NO. 2)
5' gcgctctagaagctcatggTCACAGCCTTGAAGTCAGC 3'

Baboon (D3H) liver uricase:
sense
(SEQ ID NO. 3)
5' gcgcgaattccATGGCCCACTACCATAACAACTAT 3' anti-sense
(SEQ ID NO. 4)
5' gcgcccatggtctagaTCACAGTCTTGAAGACAACTTCCT 3'

Restriction enzyme sequences, introduced at the ends of the primers and shown in lowercase in Table 1, were sense EcoRI and NcoI (pig and baboon) and anti-sense NcoI, HindIII and XbaI (pig), XbaI and NcoI (baboon). In the baboon sense primer, the third codon GAC (aspartic acid) present in baboon uricase was replaced with CAC (histidine), the codon that is present at this position in the coding sequence of the human urate oxidase pseudogene. The recombinant baboon uricase construct generated using these primers is named D3H Baboon Uricase.

The pig uricase PCR product was digested with EcoRI and HindIII and cloned into pUC18 to create pUC18-Pig Uricase. The D3H Baboon Uricase PCR product was cloned directly into PCR®II vector (TA Cloning Vector pCRThII), using TA Cloning biochemical laboratory kits for cloning of amplified nucleic acids (Invitrogen, Carlsbad, Calif.), creating PCR®II-D3H Baboon Uricase.

Ligated cDNAs were used to transform E. coli strain XL 1-Blue (Stratagene, La Jolla, Calif.). Plasmid DNA containing cloned uricase cDNA was prepared, and clones which possess the published uricase DNA coding sequences (except for the D3H substitution in baboon uricase, shown in Table 1) were selected and isolated. In the PCR®II-D3H Baboon Uricase clone chosen, the PCR®II sequences were next to the uricase stop codon, resulting from deletion of sequences introduced by PCR. As a consequence, the XbaI and NcoI restriction sites from the 3' untranslated region were eliminated, thus allowing directional cloning using NcoI at the 5' end of the PCR product and BamHI which is derived from the PCR®II vector.

Subcloning of Uricase cDNA Into pET Expression Vectors
Baboon Uricase Subcloning The D3H baboon cDNA containing full length uricase coding sequence was introduced into pET-3d expression vector (Novagen, Madison, Wis.). The PCR®II-D3H Baboon Uricase was digested with NcoI and BamHI, and the 960 bp fragment was isolated. The expression plasmid pET-3d was digested with NcoI and BamHI, and the 4600 bp fragment was isolated. The two fragments were ligated to create pET-3d-D3H-Baboon.

Pig-Baboon Chimera Uricase Subcloning

Pig-baboon chimera (PBC) uricase was constructed in order to gain higher expression, stability, and activity of the recombinant gene. PBC was constructed by isolating the 4936 bp NcoI-ApaI fragment from pET-3d-D3H-Baboon clone and ligating the isolated fragment with the 624 bp NcoI-ApaI fragment isolated from pUC18-Pig Uricase, resulting in the formation of pET-3d-PBC. The PBC uricase cDNA consists of the pig uricase codons 1-225 joined in-frame to codons 226-304 of baboon uricase.

Pig-KS Uricase Subcloning

Pig-KS uricase was constructed in order to add one lysine residue, which may provide an additional PEGylation site. KS refers to the amino acid insert of lysine into pig uricase, at position 291, in place of arginine (R291K). In addition, the threonine at position 301 was replaced with serine (T301 S). The PigKS uricase plasmid was constructed by isolating the 4696 bp NcoI-NdeI fragment of pET-3d-D3H-Baboon, and then it was ligated with the 864 bp NcoI-NdeI fragment isolated from pUC18-Pig Uricase, resulting in the formation of pET-3d-PigKS. The resulting PigKS uricase sequence consists of the pig uricase codons 1-288 joined in-frame to codons 289-304 of baboon uricase.

Subcloning of Uricase Sequence Under the Regulation of the osmB Promoter

The uricase gene was subcloned into an expression vector containing the osmB promoter (following the teaching of U.S. Pat. No. 5,795,776, incorporated herein by reference in its entirety). This vector enabled induction of protein expression in response to high osmotic pressure or culture aging. The expression plasmid pMFOA-18 contained the osmB promoter, a ribosomal binding site sequence (rbs) and a transcription terminator sequence (ter). It confers ampicillin resistance (AmpR) and expresses the recombinant human acetylcholine esterase (AChE).

Subcloning of D3H-Baboon Uricase

The plasmid pMFOA-18 was digested with NcoI and BamHI, and the large fragment was isolated. The construct pET-3d-D3H-Baboon was digested with NcoI and BamHI and the 960 bp fragment, which included the D3H Baboon Uricase gene is isolated. These two fragments were ligated to create pMFOU18.

The expression plasmid pMFXT133 contained the osmB promoter, a rbs (E. coli deo operon), ter (E. coli TrypA), the recombinant factor Xa inhibitor polypeptide (FxaI), and it 2 5 conferred the tetracycline resistance gene (TetR). The baboon uricase gene was inserted into this plasmid in order to exchange the antibiotic resistance genes. The plasmid pMFOU18 was digested with NcoI, filled-in, then it was digested with XhoI, and a 1030 bp fragment was isolated. The plasmid pMFXT133 was digested with NdeI, filled-in, then it was digested with XhoI, and the large fragment was isolated. The two fragments were ligated to create the baboon uricase expression vector, pURBA16.

Subcloning of the Pig Baboon Chimera Uricase

The plasmid pURBA16 was digested with ApaI and AlwNI, and the 2320 bp fragment was isolated. The plasmid pMFXT133 was digested with NdeI, filled-in, then it was digested with AlwNI, and the 620 bp fragment was isolated. The construct pET-3d-PBC was digested with XbaI, filled-in, then it was digested with ApaI, and the 710 bp fragment was isolated. The three fragments were ligated to create pUR-PB, a plasmid that expressed PBC uricase under the control of osmB promoter and rbs as well as the T7 rbs, which was derived from the pET-3d vector.

The T7 rbs was excised in an additional step. pUR-PB was digested with NcoI, filled-in, then digested with AlwNI, and the 3000 bp fragment was isolated. The plasmid pMFXT133 was digested with NdeI, filled in and then digested with AlwNI, and the 620 bp fragment was isolated. The two fragments were ligated to form pDUR-PB, which expresses PBC under the control of the osmB promoter.

Construction of pOUR-PB-ΔNC

Several changes were introduced into the uricase cDNA, which resulted in a substantial increase in the recombinant enzyme stability. Plasmid pOUR-PBC-ΔNC was constructed, in which the N-terminal six-residue maturation peptide and the tri-peptide at the C-terminus, which function in vivo as peroxysomal targeting signal, were both removed. This was carried out by utilizing PBC sequence in plasmid pDUR-PB and the specific oligonucleotide primers listed in Table 2, using PCR amplification.

TABLE 2

Primers for PCR Amplification of PBC-ΔNC Uricase

PBC-ΔNC Uricase:
Sense
(SEQ ID NO. 5)
5' gcgcatATGACTTACAAAAAGAATGATGAGGTAGAG 3'

Anti-sense
(SEQ ID NO. 6)
5' ccgtctagaTTAAGACAACTTCCTCTTGACTGTACCAGTAATTTT TCCGTATGG 3'

The restriction enzyme sequences introduced at the ends of the primers shown in bold and the non-coding regions are shown in lowercase in Table 2. NdeI is sense and XbaI is anti-sense. The anti-sense primer was also used to eliminate an internal NdeI restriction site by introducing a point mutation (underlined) which did not affect the amino acid sequence, and thus, facilitated subcloning by using NdeI.

The 900 base-pair fragment generated by PCR amplification of pDUR-PB was cleaved with NdeI and XbaI and isolated. The obtained fragment was then inserted into a deo expression plasmid pDBAST-RAT-N, which harbors the deo-P1P2 promoter and rbs derived from *E. coli* and constitutively expresses human recombinant insulin precursor. The plasmid was digested with NdeI and XbaI and the 4035 bp fragment was isolated and ligated to the PBC-uricase PCR product. The resulting construct, pDUR-PB-ANC, was used to transform *E. coli* K-12 Sφ733 (F-cytR strA) that expressed a high level of active truncated uricase.

The doubly truncated PBC-ΔNC sequence was also expressed under the control of osmB promoter. The plasmid pDUR-PB-ANC was digested with AlwNI-NdeI, and the 3459 bp fragment was isolated. The plasmid pMFXT133, described above, was digested with NdeI-AlwNI, and the 660 bp fragment was isolated. The fragments were then ligated to create pOUR-PB-ANC, which was introduced into *E. coli* K-12 strain W3110 F and expressed high level of active truncated uricase.

Construction of the Uricase Expression Plasmid pOUR-P-ΔN-Ks-1

This plasmid was constructed in order to improve the activity and stability of the recombinant enzyme. Pig-KS-ΔN uricase was truncated at the N-terminus only (ΔN), where the six-residue N-terminal maturation peptide was removed, and contained the mutations S46T, R291K and T301S. At position 46, there was a threonine residue instead of serine due to a conservative mutation that occurred during PCR amplification and cloning. At position 291, lysine replaced arginine, and at position 301, serine was inserted instead of threonine. Both were derived from the baboon uricase sequence. The modifications of R291K and T301S are designated KS, and discussed above. The extra lysine residue provided an additional potential PEGylation site.

Figure 4:
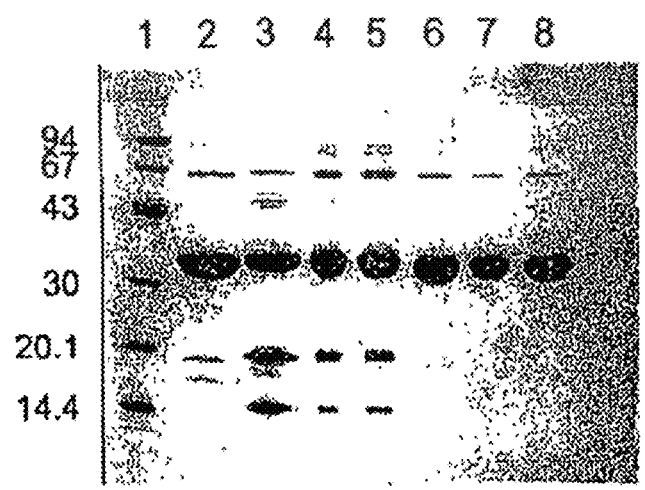
FIG. 4 depicts SDS-PAGE of pig uricase and the highly purified uricase variants produced according to Examples 1-3. The production date (month/year) and the relevant lane number for each sample is indicated in the key below. The Y axis is labeled with the weights of molecular weight markers, and the top of the figure is labeled with the lane numbers. The lanes are as follows: Lane 1—Molecular weight markers; Lane 2—Pig KS-ΔN (7/98); Lane 3—Pig (9/98); Lane 4—Pig KS (6/99); Lane 5—Pig KS (6/99); Lane 6—Pig-Δ (6/99); Lane 7—Pig KS-ΔN (7/99); Lane 8—Pig KS-ΔN (8/99).

To construct pOUR-P-ΔN-ks-1 (FIG. 1), the plasmid pOUR-PB-ANC was digested with ApaI-XbaI, and the 3873 bp fragment was isolated. The plasmid pET-3d-PKS (construction shown in FIG. 4) was digested with ApaI-SpeI, and the 270 bp fragment was isolated. SpeI cleavage left a 5' CTAG extension that was efficiently ligated to DNA fragments generated by XbaI. The two fragments were ligated to create pOUR-P-ΔN-ks-1. After ligation, the SpeI and XbaI recognition sites were lost (their site is shown in parenthesis in FIG. 9). The construct pOUR-P-ΔN-ks-1 was introduced into *E. coli* K-12 strain W3110 F, prototrophic, ATCC #27325. The resulting Pig-KS-ΔN uricase, expressed under the control of osmB promoter, yielded high levels of recombinant enzyme having superior activity and stability.

FIG. 1 illustrates the structure of plasmid pOUR-P-ΔN-ks-1. Numbers next to restriction sites indicate nucleotide position, relative to HaeII site, designated as 1; restriction sites that were lost during cloning are marked in parenthesis. Plasmid pOUR-P-ΔN-ks-1, encoding Pig-KS-ΔN uricase is 4143 base pairs (bp) long and comprised the following elements:

1. A DNA fragment, 113 bp long, spanning from nucleotide number 1 to NdeI site (at position 113), which includes the osmB promoter and ribosome binding site (rbs).
2. A DNA fragment, 932 bp long, spanning from NdeI (at position 113) to SpeI/XbaI junction (at position 1045), which includes: 900 bp of Pig-KS-ΔN (nucleic acid sequence of amino terminus truncated pig uricase protein in which amino acids 291 and 301 with lysine and serine, respectively, are replaced) coding region and 32 bp flanking sequence derived from pCR™II, from the TA cloning site upstream to the SpeI/XbaI restriction site.
3. A 25 bp multiple cloning sites sequence (MCS) from SpeI/XbaI junction (at position 1045) to HindIII (at position 1070).
4. A synthetic 40 bp oligonucleotide containing the TrpA transcription terminator (ter) with HindIII (at position 1070) and AatII (at position 1110) ends.
5. A DNA fragment, 1519 bp long, spanning from AatII (at position 1110) to MscI/ScaI (at position 2629) sites on pBR322 that includes the tetracycline resistance gene (TetR).
6. A DNA fragment, 1514 bp long, spanning from ScaI (at position 2629) to HaeII (at position 4143) sites on pBR322 that includes the origin of DNA replication.

FIG. 2 shows the DNA and the deduced amino acid sequences of Pig-KS-ΔN uricase. In this figure, the amino acid numbering is according to the complete pig uricase sequence. Following the initiator methionine residue, a threonine was inserted in place of the aspartic acid of the pig uricase sequence. This threonine residue enabled the removal of methionine by bacterial aminopeptidase. The gap in the amino acid sequence illustrates the deleted N-terminal maturation peptide. The restriction sites that were used for the various steps of subcloning of the different uricase sequences (ApaI, NdeI, BamHI, EcoRI and SpeI) are indicated. The 3' untranslated sequence, shown in lowercase letters, was derived from PCR®II sequence. The translation stop codon is indicated by an asterisk.

FIG. 3 shows alignment of the amino acid sequences of the various recombinant uricase sequences. The upper line represents the pig uricase, which included the full amino acid sequence. The second line is the sequence of the doubly truncated pig-baboon chimera uricase (PBC-ΔNC). The third line shows the sequence of Pig-KS-ΔN uricase, that is only truncated at the N-terminus and contained the mutations S46T and the amino acid changes R291K and T301S, both reflecting the baboon origin of the carboxy terminus of the uricase coding sequence. The asterisks indicate the positions in which there are differences in amino acids in the Pig-KS-ΔN as compared to the published pig uricase sequence; the circles indicate positions in which there are differences in amino acids in Pig-KS-ΔN compared to PBC-ΔN, the pig-baboon chimera; and dashed lines indicate deletion of amino acids.

cDNA for native baboon, pig, and rabbit uricase with the Y97H mutation, and the pig/baboon chimera (PBC) were constructed for cloning into *E. coli*. Clones expressing high levels of the uricase variants were constructed and selected such that all are W3110 F *E. coli*, and expression is regulated by osmB. Plasmid DNAs were isolated, verified by DNA sequencing and restriction enzyme analysis, and cells were cultured.

Construction of the truncated uricases, including pig-ΔN and Pig-KS-ΔN was done by cross-ligation between PBC-ΔNC and Pig-KS, following cleavage with restriction endonucleases ApaI and XbaI, and ApaI plus SpeI, respectively. It is reasonable that these truncated mutants would retain activity, since the N-terminal six residues, the "maturation peptide" (1-2), and the C-terminal tri-peptide, "peroxisomal targeting signal" (3-5), do not have functions which significantly affect enzymatic activity, and it is possible that these sequences may be immunogenic. Clones expressing very high levels of the uricase variants were selected.

Example 2

Transformation of the Expression Plasmid into a Bacterial Host Cell

The expression plasmid, pOUR-P-ΔN-ks-1, was introduced into *E. coli* K-12 strain W3110 F Bacterial cells were prepared for transformation involved growth to mid log phase in Luria broth (LB), then cells were harvested by centrifugation, washed in cold water, and suspended in 10% glycerol, in water, at a concentration of about $3 \times 10^{10}$ cells per ml. The cells were stored in aliquots, at −70° C. Plasmid DNA was precipitated in ethanol and dissolved in water.

Bacterial cells and plasmid DNA were mixed, and transformation was done by the high voltage electroporation method using Gene Pulser II from BIO-RAD (Trevors et al (1992). Electrotransformation of bacteria by plasmid DNA, in Guide to Electroporation and Electrofusion (D. C. Chang, B. M. Chassy, J. A. Saunders and A. E. Sowers, eds.), pp. 265-290, Academic Press Inc., San Diego, Hanahan et al (1991) Meth. Enzymol., 204, 63-113). Transformed cells were suspended in SOC medium (2% tryptone, 0.5% yeast extract, 10 mM NaCl, 2.5 mM KCl, 10 mM $MgCl_2$, 10 mM $MgSO_4$, 20 mM glucose), incubated, at 37° C., for 1 hour and selected for tetracycline resistance. A high expresser clone was selected.

Example 3

Recombinant Uricase Preparation

Bacteria such as those transformed (see above) were cultured in medium containing glucose; pH was maintained at 7.2±0.2, at approximately 37° C.

Towards the last 5-6 hours of cultivation, the medium was supplemented with KCl to a final concentration of 0.3M. Cultivation was continued to allow uricase accumulation.

Recombinant uricase accumulated within bacterial cells as an insoluble precipitate similar to inclusion bodies (IBs). The cell suspension was washed by centrifugation and suspended in 50 mM Tris buffer, pH 8.0 and 10 mM EDTA and brought to a final volume of approximately 40 times the dry cell weight.

Recombinant uricase-containing IBs, were isolated by centrifugation following disruption of bacterial cells using lysozyme and high pressure. Treatment with lysozyme (2000-3000 units/ml) was done for 16-20 hours at pH 8.0 and 7±3° C., while mixing. The pellet was washed with water and stored at −20° C. until use.

The enriched IBs were further processed after suspending in 50 mM $NaHCO_3$ buffer, pH 10.3±0.1. The suspension was incubated overnight, at room temperature, to allow solubilization of the IB-derived uricase, and subsequently clarified by centrifugation.

Uricase was further purified by several chromatography steps. Initially, chromatography was done on a Q-Sepharose FF column. The loaded column was washed with bicarbonate buffer containing 150 mM NaCl, and uricase was eluted with bicarbonate buffer, containing 250 mM NaCl. Then, Xanthine-agarose resin (Sigma) was used to remove minor impurities from the uricase preparation. The Q-Sepharose FF eluate was diluted with 50 mM glycine buffer, pH 10.3±0.1, to a protein concentration of approximately 0.25 mg/ml and loaded. The column was washed with bicarbonate buffer, pH 10.3±0.1, containing 100 mM NaCl, and uricase was eluted with the same buffer supplemented with 60 μM xanthine. At this stage, the uricase was repurified by Q-Sepharose chromatography to remove aggregated forms.

The purity of each uricase preparation is greater than 95%, as determined by size exclusion chromatography. Less than 0.5% aggregated forms are detected in each preparation using a Superdex 200 column.

Table 3 summarizes purification of Pig-KSΔN uricase from IBs derived from 25 L fermentation broth.

TABLE 3

Purification Of Pig-KSΔN Uricase

| Purification step | | Protein (mg) | Activity (U) | Specific Activity (U/mg) |
|---|---|---|---|---|
| IB dissolution | | 12,748 | 47,226 | 3.7 |
| Clarified solution | | 11,045 | 44,858 | 4.1 |
| Q-Sepharose I - | main pool | 7,590 | 32,316 | 4.3 |
| Xanthine Agarose - | main pool | 4,860 | 26,361 | 5.4 |
| Q-Sepharose II - | main pool | 4,438 | 22,982 | 5.2 |
| 30 kD UF retentate | | 4,262 | 27,556 | 6.5 |

Example 4

Characteristics of Recombinant Uricases

SDS-PAGE

SDS-PAGE analysis of the highly purified uricase variants (FIG. 4) revealed a rather distinctive pattern. The samples were stored at 4° C., in carbonate buffer, pH 10.3, for up to several months. The full-length variants, Pig, Pig-KS, and PBC, show accumulation of two major degradation products having molecular weights of about 20 and 15 kD. This observation suggests that at least a single nick split the uricase subunit molecule. A different degradation pattern is detected in the amino terminal shortened clones and also in the rabbit uricase, but at a lower proportion. The amino terminus of the rabbit resembles that of the shortened clones. The amino terminal sequences of the uricase fragments generated during purification and storage were determined.

Peptide Sequencing

N-terminal sequencing of bulk uricase preparations was done using the Edman degradation method. Ten cycles were performed. Recombinant Pig uricase (full length clone) generated a greater abundance of degradation fragments compared to Pig-KS-ΔN. The deduced sites of cleavage leading to the degradation fragments are as follows:

1) Major site at position 168 having the sequence:
-QSG↓iFEGFI-
2) Minor site at position 142 having the sequence:
-IRN↓GPPVI- The above sequences do not suggest any known proteolytic cleavage.

Nevertheless, cleavage could arise from either proteolysis or some chemical reaction. The amino-truncated uricases are surprisingly more stable than the non-amino truncated uricases. PBCΔNC also had stability similar to the other AN molecules and less than non-amino-truncated PBC.

Potency

Activity of uricase was measured by a UV method. Enzymatic reaction rate was determined by measuring the decrease in absorbance at 292 nm resulting from the oxidation of uric acid to allantoin. One activity unit is defined as the quantity of uricase required to oxidize one mole of uric acid per minute, at 25° C., at the specified conditions. Uricase potency is expressed in activity units per mg protein (U/mg).

The extinction coefficient of 1 mM uric acid at 292 nm is 12.2 mM$^{-1}$ cm$^{-1}$. Therefore, oxidation of 1 μmole of uric acid per ml reaction mixture resulted in a decrease in absorbance of 12.2 mA$_{292}$. The absorbance change with time (ΔA$_{292}$ per minute) was derived from the linear portion of the curve.

Protein concentration was determined using a modified Bradford method (Macart and Gerbaut (1982) *Clin Chim Acta* 122:93-101). The specific activity (potency) of uricase was calculated by dividing the activity in U/ml with protein concentration in mg/ml. The enzymatic activity results of the various recombinant uricases are summarized in Table 4. The results of commercial preparations are included in this table as reference values. It is apparent from these results that truncation of uricase proteins has no significant effect on their enzymatic activity.

TABLE 4

Summary of Kinetic Parameters of Recombinant and Native Uricases

| Uricases | Concentration[1] of Stock (mg/ml) | Specific Activity (U/mg)[2] | Km[4] (μM Uric Acid) | Kcat[5] (1/min) |
|---|---|---|---|---|
| Recombinant | | | | |
| Pig | 0.49 | 7.41 | 4.39 | 905 |
| Pig-ΔN | 0.54 | 7.68 | 4.04 | 822 |
| Pig-KS | 0.33 | 7.16 | 5.27 | 1085 |
| Pig-KS-ΔN | 1.14 | 6.20 | 3.98 | 972 |
| PBC | 0.76 | 3.86 | 4.87 | 662 |
| PBC-ΔNC | 0.55 | 3.85 | 4.3 | 580 |
| Rabbit | 0.44 | 3.07 | 4.14 | 522 |
| Native | | | | |
| Pig (Sigma) | 2.70 | 3.26[3] | 5.85 | 901 |
| *A. flavus* (Merck) | 1.95 | 0.97[3] | 23.54 | 671 |

Table 4 Notes:
[1]Protein concentration was determined by absorbance measured at 278 nm, using an Extinction coefficient of 11.3 for a 10 mg/ml uricase solution (Mahler, 1963).
[2]1 unit of uricase activity is defined as the amount of enzyme that oxidizes 1 μmole of uric acid to allantoin per minute, at 25° C.
[3]Specific activity values were derived from the Lineweaver-Burk plots, at a concentration of substrate equivalent to 60 μM.
[4]Reaction Mixtures were composed of various combinations of the following stock solutions 100 mM sodium borate buffer, pH 9.2 300 μM Uric acid in 50 mM sodium borate buffer, pH 9.2 1 mg/ml BSA in 50 mM sodium borate buffer, pH 9.2
[5]K$_{cat}$ was calculated by dividing the Vmax (calculated from the respective Lineweaver-Burk plots) by the concentration of uricase in reaction mixture (expressed in mol equivalents, based on the tetrameric molecular weights of the uricases).

Example 5

Conjugation of Uricase with m-PEG (PEGylation)

Pig-KS-ΔN Uricase was conjugated using m-PEG-NPC (monomethoxy-poly(ethylene glycol)-nitrophenyl carbonate). Conditions resulting in 2-12 strands of 5, 10, or 20 kD PEG per uricase subunit were established. m-PEG-NPC was gradually added to the protein solution. After PEG addition was concluded, the uricase/m-PEG-NPC reaction mixture was then incubated at 2-8° C. for 16-18 hours, until maximal unbound m-PEG strands were conjugated to uricase.

The number of PEG strands per PEG-uricase monomer was determined by Superose 6 size exclusion chromatography (SEC), using PEG and uricase standards. The number of bound PEG strands per subunit was determined by the following equation:

$$PEG\ strands/subunit = \frac{3.42 \times Amount\ of\ PEG\ in\ injected\ sample\ (\mu g)}{Amount\ of\ protein\ in\ injected\ sample\ (\mu g)}$$

The concentration of PEG and protein moieties in the PEG-uricase sample was determined by size exclusion chromatography (SEC) using ultraviolet (UV) and refractive index (RI) detectors arranged in series (as developed by Kunitani, et al., 1991). Three calibration curves are generated: a protein curve (absorption measured at 220 nm); a protein curve (measured by RI); and PEG curve (measured by RI). Then, the PEG-uricase samples were analyzed using the same system. The resulting UV and RI peak area values of the experimental samples were used to calculate the concentrations of the PEG and protein relative to the calibration curves. The index of 3.42 is the ratio between the molecular weight of uricase monomer (34,192 Daltons) to that of the 10 kD PEG.

Attached PEG improved the solubility of uricase in solutions having physiological pH values. Table 5 provides an indication of the variability between batches of PEGylated Pig-KS-ΔN uricase product. In general, there is an inverse relation between the number of PEG strands attached and retained specific activity (SA) of the enzyme.

TABLE 5

Enzymatic Activity Of PEGylated Pig-KS-ΔN Uricase Conjugates

| Conjugate Batches | PEG MW (kD) | PEG Strands per Uricase Subunit | Uricase SA (U/mg) | SA Percent of Control |
|---|---|---|---|---|
| ΔN-Pig-KS-1-17 # | — | — | 8.2 | 100 |
| LP-17 | 5 | 9.7 | 5.8 | 70.4 |
| 1-15 # | 10 | 2.3 | 7.8 | 94.6 |
| 13 # | 10 | 5.1 | 6.4 | 77.9 |
| 14 # | 10 | 6.4 | 6.3 | 76.9 |
| 5-15 # | 10 | 6.5 | 6.4 | 77.5 |
| 5-17 # | 10 | 8.8 | 5.4 | 65.3 |
| 4-17 # | 10 | 11.3 | 4.5 | 55.3 |
| 1-18 # | 10 | 11.8 | 4.4 | 53.9 |
| | 20 | 11.5 | 4.5 | 54.4 |

Example 6

PEGylation of Uricase with 1000 D and 100,000 D PEG

Pig-KS-ΔN Uricase was conjugated using 1000 D and 100,000 D m-PEG-NPC as described in Example 5. Conditions resulting in 2-11 strands of PEG per uricase subunit were used. After PEG addition was concluded, the uricase/m-PEG-NPC reaction mixture was then incubated at 2-8° C. for 16-18 hours, until maximal unbound m-PEG strands were conjugated to uricase.

The number of PEG strands per PEG-uricase monomer was determined as described above.

Attached PEG improved the solubility of uricase in solutions having physiological pH values.

Example 7

Pharmacokinetics of Pig-KS-ΔN Uricase Conjugated with PEG

Biological experiments were undertaken in order to determine the optimal extent and size of PEGylation needed to provide therapeutic benefit.

Pharmacokinetic studies in rats, using i.v. injections of 0.4 mg (2 U) per kg body weight of unmodified uricase, administered at day 1 and day 8, yielded a circulating half life of about 10 minutes. However, studies of the clearance rate in rats with 2-11×10 kD PEG-Pig-KS-ΔN uricase, after as many as 9 weekly injections, indicated that clearance did not depend on the number of PEG strands (within this range) and remained relatively constant throughout the study period (see Table 6; with a half-life of about 30 hours). The week-to-week differences are within experimental error. This same pattern is apparent after nine injections of the 10×5 kD PEG, and 10×20 kD PEG-uricase conjugates. The results indicated that regardless of the extent of uricase PEGylation, in this range, similar biological effects were observed in the rat model.

TABLE 6

Half Lives of PEGylated Pig-KS-ΔN Uricase Preparations in Rats

Extent of Modification (PEG Strands per Uricase Subunit)

| Week | 5 kD PEG 10x | 10 kD PEG 2x | 10 kD PEG 5x | 10 kD PEG 7x | 10 kD PEG 9x | 10 kD PEG 11x | 20 kD PEG 10x |
|---|---|---|---|---|---|---|---|
| 1 | 25.7 ± 1.7 (5) | 29.4 ± 3.4 (5) | 37.7 ± 3.1 (5) | 37.6 ± 3.9 (5) | 36.9 ± 4.3 (5) | 31.4 ± 4.3 (5) | 21.6 ± 1.5 (5) |
| 2 | — | — | — | 26.7 ± 3.0 (5) | 28.4 ± 1.6 (5) | — | — |
| 3 | 27.5 ± 3.8 (5) | 29.0 ± 2.6 (5) | 29.9 ± 11.7 (5) | 32.7 ± 11.1 (5) | 26.3 ± 4.7 (5) | 11.8 ± 3.3 (5) | 14.5 ± 2.7 (5) |
| 4 | — | — | 27.1 ± 5.3 (5) | 18.4 ± 2.2 (4) | 19.7 ± 5.6 (4) | — | — |
| 5 | 28.6 ± 1.7 (5) | 22.5 ± 2.7 (5) | 34.3 ± 3.9 (4) | 37.3 ± 3.0 (5) | 30.4 ± 3.6 (5) | 30.5 ± 1.3 (5) | 19.3 ± 2.5 (5) |
| 6 | — | — | 35.4 ± 3.1 (14) | 27.1 ± 3.6 (13) | 30.7 ± 2.9 (13) | — | — |
| 7 | 16.5 ± 4.9 (5) | 32.5 ± 4.3 (5) | — | — | — | 16.12 ± 2.7 (5) | 25.8 ± 2.5 (5) |
| 8 | — | — | — | — | — | — | — |
| 9 | 36.8 ± 4.0 (15) | 28.7 ± 2.7 (15) | 34.0 ± 2.4 (13) | 24.2 ± 3.4 (13) | 31.0 ± 2.6 (13) | 29.3 ± 1.4 (15) | 26.7 ± 0.5 (15) |

Table 6 notes:
Results are indicated in hours ± standard error of the mean.
Numbers in parenthesis indicate the number of animals tested.

Rats received weekly i.v. injections of 0.4 mg per kilogram body weight of Pig-KS-ΔN uricase modified as indicated in the table. Each group initially comprised 15 rats, which were alternately bled in subgroups of 5. Several rats died during the study due to the anesthesia. Half-lives were determined by measuring uricase activity (calorimetric assay) in plasma samples collected at 5 minutes, and 6, 24 and 48 hours post injection.

Table 5 describes the batches of PEGylated uricase used in the study.

Bioavailability studies with 6×5 kD PEG-Pig-KS-ΔN uricase in rabbits indicate that, after the first injection, the circulation half-life is 98.2±1.8 hours (i.v.), and the bioavailability after i.m. and subcutaneous (s.c.) injections was 71% and 52%, respectively. However, significant anti-uricase antibody titers were detected, after the second i.m. and s.c. injections, in all of the rabbits, and clearance was accelerated following subsequent injections. Injections of rats with the same conjugate resulted in a half-life of 26±1.6 hours (i.v.), and the bioavailability after i.m. and s.c. injections was 33% and 22%, respectively.

Figure 5:
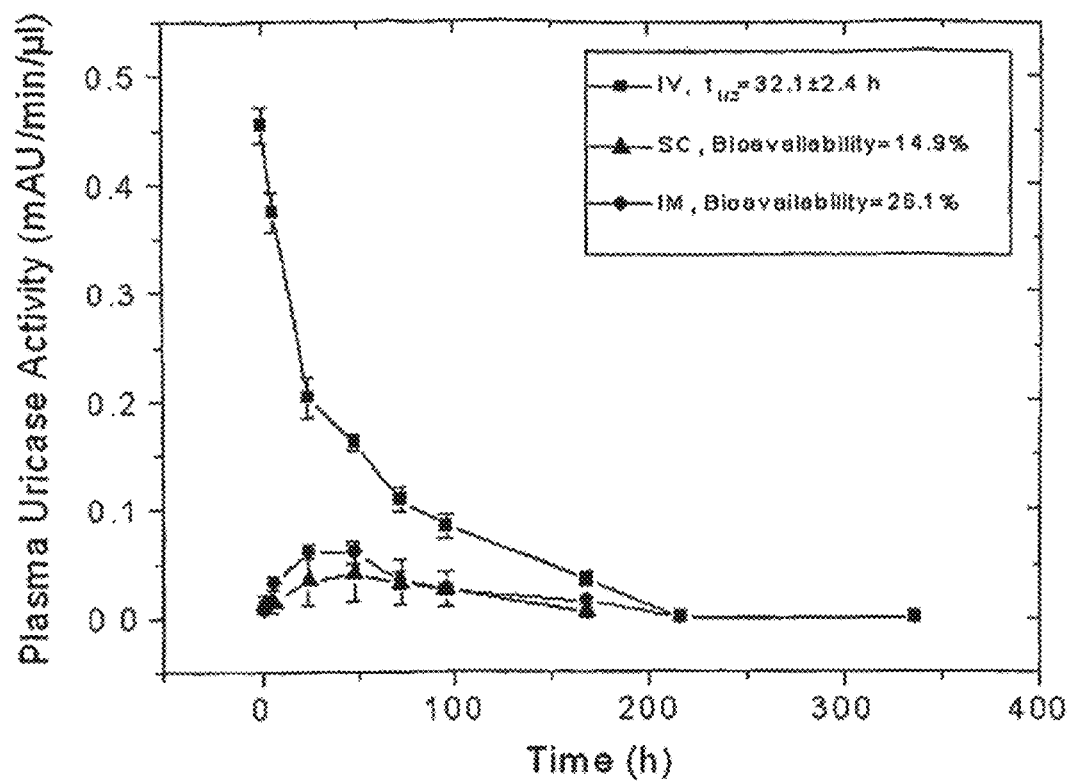
FIG. 5 depicts the pharmacokinetic profiles of PEGylated (9×10 kD) Pig-KS-ΔN uricase in rats following IM (intramuscular), SC (subcutaneous), and IV (intravenous) injections, as determined by monitoring enzymatic activity in blood samples. Uricase activity in plasma samples, which are collected at the indicated time points, is determined using the colorimetric assay. Activity values (mAU=milli-absorbance units) represent the rate of enzymatic reaction per 1 µl of plasma sample. The bioavailability (amount of drug reaching the circulation relative to an IV injection) of uricase injected was calculated from the area under the curve of the graph.

Studies in rats, with 9×10 kD PEG-Pig-KS-ΔN uricase indicate that the circulation half-life after the first injection is 42.4 hours (i.v.), and the bioavailability, after i.m. and s.c. injections, was 28.9% and 14.5%, respectively (see FIG. 5 and Table 7). After the fourth injection, the circulation half-life was 32.1±2.4 hours and the bioavailability, after the i.m. and s.c. injections was 26.1% and 14.9%, respectively.

Figure 6:
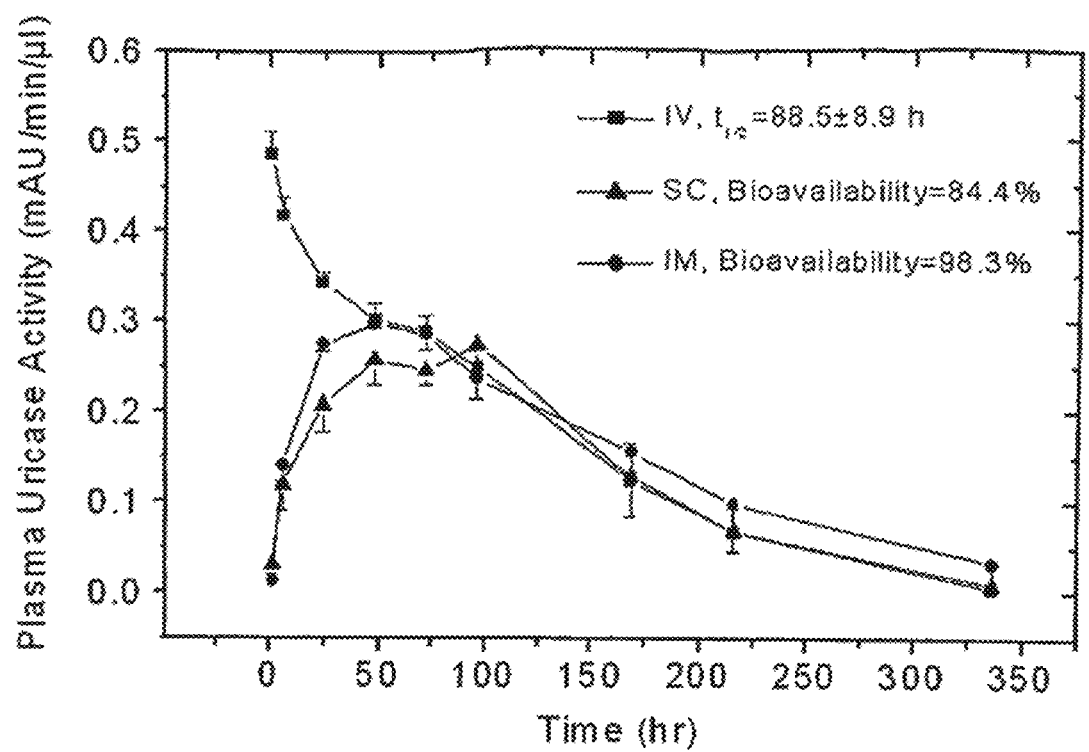
FIG. 6 depicts the pharmacokinetic profiles of PEGylated (9×10 kD) Pig-KS-ΔN uricase in rabbits following IM (intramuscular), SC (subcutaneous), and IV (intravenous) injections, as determined by monitoring enzymatic activity in blood samples. Uricase activity in plasma samples collected at the indicated time points is determined using a colorimetric assay. Activity values (mAU=milli-absorbance units) represent the rate of enzymatic reaction per 1 µl of plasma sample. The bioavailability (amount of drug reaching the circulation relative to an IV injection) of uricase injected was calculated from the area under the curve of the graph.

Similar pharmacokinetic studies, in rabbits, with 9×10 kD PEG-Pig-KS-ΔN uricase indicate that no accelerated clearance was observed following injection of this conjugate (4 biweekly injections were administered). In these animals, the circulation half-life after the first injection was 88.5 hours (i.v.), and the bioavailability, after i.m. and s.c. injections, was 98.3% and 84.4%, respectively (see FIG. 6 and Table 7). After the fourth injection the circulation half-life was 141.1±15.4 hours and the bioavailability, after the i.m. and s.c. injections was 85% and 83%, respectively.

Figure 7:
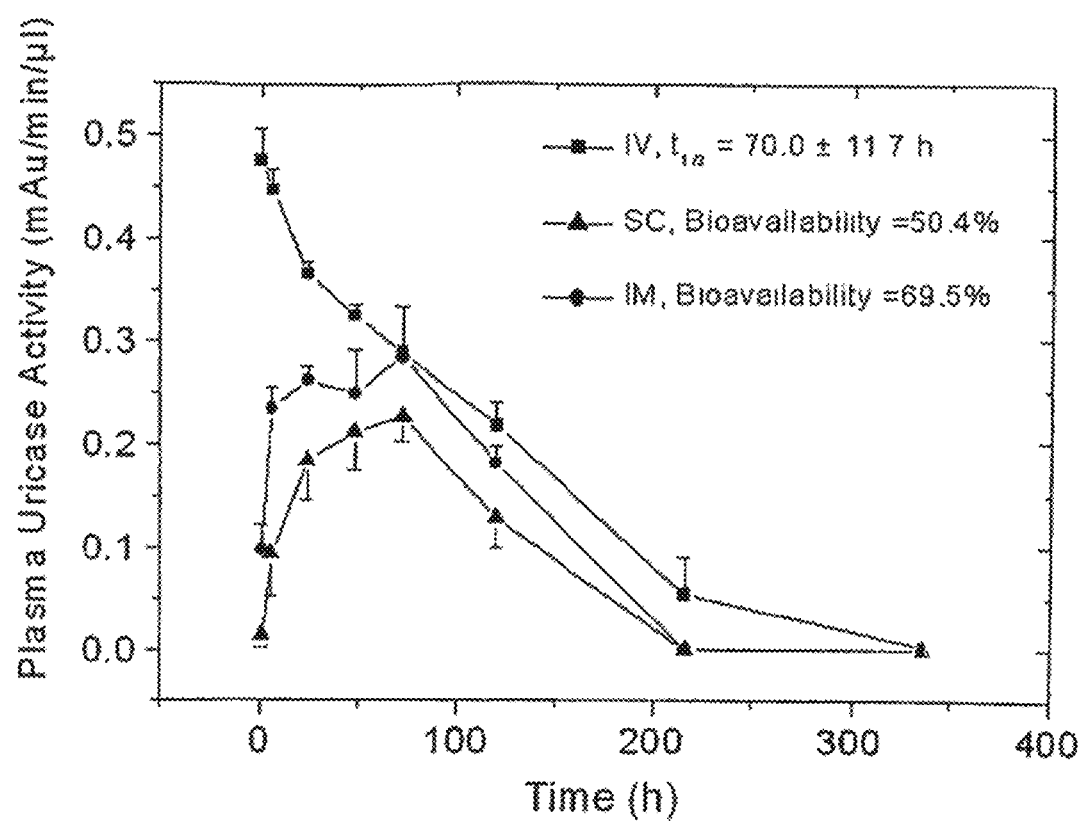
FIG. 7 depicts the pharmacokinetic profiles of PEGylated (9×10 kD) Pig-KS-ΔN uricase in dogs following IM (intramuscular), SC (subcutaneous), and IV (intravenous) injections, as determined by monitoring enzymatic activity in blood samples. Uricase activity in plasma samples, which are collected at the indicated time points, is determined using the calorimetric assay. Activity values (mAU=milli-absorbance units) represent the rate of enzymatic reaction per 1 µl of plasma sample. The bioavailability (amount of drug reaching the circulation relative to an IV injection) of uricase injected was calculated from the area under the curve of the graph.

Similar studies with 9×10 kD PEG-Pig-KS-ΔN were done to assess the bioavailability in beagles (2 males and 2 females in each group). A circulation half-life of 7±11.7 hours was recorded after the first i.v. injection, and the bioavailability, after the i.m. and s.c. injections was 69.5% and 50.4%, respectively (see FIG. 7 and Table 7).

Figure 8:
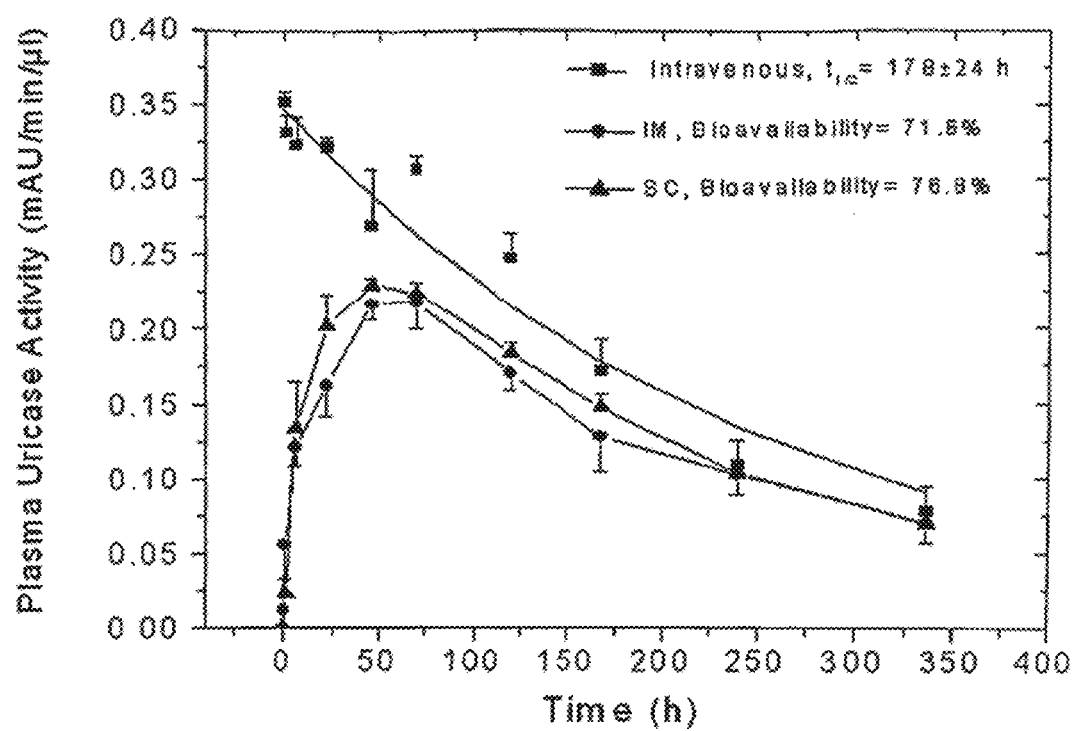
FIG. 8 depicts the pharmacokinetic profiles of PEGylated (9×10 kD) Pig-KS-ΔN uricase in pigs following IM (intramuscular), SC (subcutaneous), and IV (intravenous) injections, as determined by monitoring enzymatic activity in blood samples. Uricase activity in plasma samples, which are collected at the indicated time points, is determined using the colorimetric assay. Activity values (mAU=milli-absorbance units) represent the rate of enzymatic reaction per 1 µl of plasma sample. The bioavailability (amount of drug reaching the circulation relative to an IV injection) of uricase injected was calculated from the area under the curve of the graph.

Studies with 9×10 kD PEG-Pig-KS-ΔN preparations were done using pigs. Three animals per group were used for administration via the i.v., s.c. and i.m. routes. A circulation half-life of 178±24 hours was recorded after the first i.v. injection, and the bioavailability, after the i.m. and s.c. injections was 71.6% and 76.8%, respectively (see FIG. 8 and Table 7).

TABLE 7

Pharmacokinetic Studies with 9 × 10 kD PEG-Pig-KS-ΔN Uricase

| Injection # | Half-life (hours) i.v. | Bioavailability i.m. | Bioavailability s.c. |
|---|---|---|---|
| Rats | | | |
| 1 | 42.4 ± 4.3 | 28.9% | 14.5% |
| 2 | 24.1 ± 5.0 | 28.9% | 14.5% |
| 4 | 32.1 ± 2.4 | 26.1% | 14.9% |
| Rabbits | | | |
| 1 | 88.5 ± 8.9 | 98.3% | 84.4% |
| 2 | 45.7 ± 40.6 | 100% | 100% |
| 4 | 141.1 ± 15.4 | 85% | 83% |
| Dogs | | | |
| 1 | 70.0 ± 11.7 | 69.5% | 50.4% |
| Pigs | | | |
| 1 | 178 ± 24 | 71.6% | 76.8% |

Absorption, distribution, metabolism, and excretion (ADME) studies were done after iodination of 9×10 kD PEG-Pig-KS-ΔN uricase by the Bolton & Hunter method with $^{125}$I. The labeled conjugate was injected into 7 groups of 4 rats each (2 males and 2 females). Distribution of radioactivity was analyzed after 1 hour and every 24 hours for 7 days (except day 5). Each group, in its turn, was sacrificed and the different organs were excised and analyzed. The seventh group was kept in a metabolic cage, from which the urine and feces were collected. The distribution of the material throughout the animal's body was evaluated by measuring the total radioactivity in each organ, and the fraction of counts (kidney, liver, lung, and spleen) that were available for precipitation with TCA (i.e. protein bound, normalized to the organ size). Of the organs that were excised, none had a higher specific radioactivity than the others, thus no significant accumulation was seen for instance in the liver or kidney. 70% of the radioactivity was excreted by day 7.

Example 8

Clinical Trial Results

A randomized, open-label, multicenter, parallel group study was performed to assess the urate response, and pharmacokinetic and safety profiles of PEG-uricase (Puricase®, Savient Pharmaceuticals) in human patients with hyperuricemia and severe gout who were unresponsive to or intolerant of conventional therapy. The mean duration of disease was 14 years and 70 percent of the study population had one or more tophi.

In the study, 41 patients (mean age of 58.1 years) were randomized to 12 weeks of treatment with intravenous PEG-uricase at one of four dose regimens: 4 mg every two weeks (7 patients); 8 mg every two weeks (8 patients); 8 mg every four weeks (13 patients); or 12 mg every four weeks (13 patients). Plasma uricase activity and urate levels were measured at defined intervals. Pharmacokinetic parameters, mean plasma urate concentration and the percentage of time that plasma urate was less than or equal to 6 mg/dL were derived from analyses of the uricase activities and urate levels.

Patients who received 8 mg of PEG-uricase every two weeks had the greatest reduction in PUA with levels below 6 mg/dL 92 percent of the treatment time (pre-treatment plasma urate of 9.1 mg/dL vs. mean plasma urate of 1.4 mg/dL over 12 weeks).

Substantial and sustained lower plasma urate levels were also observed in the other PEG-uricase treatment dosing groups: PUA below 6 mg/ml 86 percent of the treatment time in the 8 mg every four weeks group (pre-treatment plasma urate of 9.1 mg/dL vs. mean plasma urate of 2.6 mg/dL over 12 weeks); PUA below 6 mg/ml 84 percent of the treatment time in the 12 mg every four weeks group (pre-treatment plasma urate of 8.5 mg/dL vs. mean plasma urate of 2.6 mg/dL over 12 weeks); and PUA below 6 mg/ml 73 percent of the treatment time in the 4 mg every two weeks group (pre-treatment plasma urate of 7.6 mg/dL vs. mean plasma urate of 4.2 mg/dL over 12 weeks).

The maximum percent decrease in plasma uric acid from baseline within the first 24 hours of PEG-uricase dosing was 72% for subjects receiving 4 mg/2 weeks (p equals 0.0002); 94% for subjects receiving 8 mg/2 weeks (p less than 0.0001); 87% for subjects receiving 8 mg/4 weeks (p less than 0.0001); and 93% for subjects receiving 12 mg/4 weeks (p less than 0.0001).

The percent decrease in plasma uric acid from baseline over the 12-week treatment period was 38% for subjects receiving 4 mg/2 weeks (p equals 0.0002); 86% for subjects receiving 8 mg/2 weeks (p less than 0.0001); 58% for subjects receiving 8 mg/4 weeks (p equals 0.0003); and 67% for subjects receiving 12 mg/4 weeks (p less than 0.0001).

Surprisingly, some subjects receiving PEG-uricase experienced an infusion related adverse event, i.e., an infusion reaction. These reactions occurred in 14% of the total infusions.

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

We claim:

1. A method of reducing elevated uric acid levels in a subject in need thereof, comprising intravenously administering a pharmaceutical composition comprising:
   a conjugate comprising a tetrameric uricase and polyethylene glycol (PEG), wherein the uricase comprises the amino acid sequence of SEQ ID NO: 8; and
   phosphate buffered saline (PBS).

2. The method of claim 1, wherein the PEG is monomethoxyPEG (mPEG).

3. The method of claim 2, wherein the mPEG has a molecular weight between 5 kDa and 20 kDa.

4. The method of claim 3, wherein the mPEG has a molecular weight of about 10 kDa.

5. The method of claim 4, wherein the mPEG is covalently attached to a lysine residue of the uricase.

6. The method of claim 4, wherein the conjugate comprises about 2-12 mPEG molecules per uricase monomer.

7. The method of claim 6, wherein the pharmaceutical composition comprises 8 mg of the uricase.

8. The method of claim 1, wherein the pharmaceutical composition comprises 8 mg of the uricase per mL of solution.

9. The method of claim 8, wherein the pharmaceutical composition is diluted into 250 mL of saline solution for administration.

10. The method of claim 1, wherein the pharmaceutical composition is administered at a dosage of 8 mg of the uricase.

11. The method of claim 1, wherein the pharmaceutical composition is administered at a dosage of 8 mg of the uricase every two weeks.

12. The method of claim 1, wherein the pharmaceutical composition is administered over a 120-minute period.

13. The method of claim 12, wherein the uric acid level is reduced in the plasma of the subject.

14. The method of claim 13, wherein the plasma uric acid level is lowered to 6.0 mg/dl or less.

15. The method of claim 13, wherein the subject has a plasma uric acid level of 6.0 mg/dl or less for at least 80% of a treatment period.

16. The method of claim 11, wherein the subject receives an antihistamine or a corticosteroid prior to the administration of the conjugate.

17. The method of claim 11, wherein the subject receives acetaminophen prior to the administration of the conjugate.

18. The method of claim 11, wherein the subject receives a nonsteroidal anti-inflammatory drug (NSAID) prior to the administration of the conjugate.

19. The method of claim 11, wherein the subject is an adult subject.

20. The method of claim 11, wherein the subject is suffering from gout.

21. The method of claim 11, wherein the subject is suffering from gout that is refractory to conventional therapy.

* * * * *